US012624385B2

(12) United States Patent
Soenksen Martinez et al.

(10) Patent No.: US 12,624,385 B2
(45) Date of Patent: May 12, 2026

(54) RIBOREGULATORS AND METHODS OF USE THEREOF

(71) Applicants: President and Fellows of Harvard College, Cambridge, MA (US); Massachusetts Institute of Technology, Cambridge, MA (US)

(72) Inventors: Luis Ruben Soenksen Martinez, Boston, MA (US); Nicolaas Angenent-Mari, Somerville, MA (US); Alexander S. Garruss, Cambridge, MA (US); James J. Collins, Newton, MA (US); George M. Church, Cambridge, MA (US); Katherine Collins, Cambridge, MA (US); Diogo M. Camacho, Cambridge, MA (US)

(73) Assignees: President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 902 days.

(21) Appl. No.: 17/784,899

(22) PCT Filed: Dec. 11, 2020

(86) PCT No.: PCT/US2020/064695
§ 371 (c)(1),
(2) Date: Jun. 13, 2022

(87) PCT Pub. No.: WO2021/194580
PCT Pub. Date: Sep. 30, 2021

(65) Prior Publication Data
US 2023/0022775 A1    Jan. 26, 2023

Related U.S. Application Data

(60) Provisional application No. 62/948,175, filed on Dec. 13, 2019.

(51) Int. Cl.
*C12Q 1/6816* (2018.01)
*C12N 15/10* (2006.01)
(Continued)

(52) U.S. Cl.
CPC ....... *C12Q 1/6816* (2013.01); *C12N 15/1089* (2013.01); *C12N 15/11* (2013.01);
(Continued)

(58) Field of Classification Search
None
See application file for complete search history.

(56) References Cited

U.S. PATENT DOCUMENTS 9,550,987 B2    1/2017   Green et al.
9,593,338 B2    3/2017   Liu et al.
(Continued)

FOREIGN PATENT DOCUMENTS

EP         2 221 371 A1    8/2010
WO    WO 2004/046321 A2    6/2004
(Continued)

OTHER PUBLICATIONS

ZNF175 [online]. GTEX Portal; 2025 [retrieved on Jul. 16, 2025]. Retrieved from the Internet: https://gtexportal.org/home/gene/ZNF17 (Year: 2025).*
(Continued)

*Primary Examiner* — Anne M. Gussow
*Assistant Examiner* — Emma R Hoppe
(74) *Attorney, Agent, or Firm* — Wolf, Greenfield & Sacks, P.C.

(57) ABSTRACT

This disclosure provides riboregulators specific for particular viruses or for particular human transcription factors. The viral-specific riboregulators may be used to detect the presence of the particular virus, and this may enable diagnosis of an infection. The transcription factor specific riboregulators
(Continued)

Synthetic biology RNA tool (e.g. Toehold Switch)

may be used to detect the presence and/or measure the level of the particular transcription factor, and this may enable diagnosis or prognosis of a particular condition such as cancer.

23 Claims, 39 Drawing Sheets

Specification includes a Sequence Listing.

(51) Int. Cl.

| | |
|---|---|
| *C12N 15/11* | (2006.01) |
| *C12Q 1/6886* | (2018.01) |
| *C12Q 1/6897* | (2018.01) |
| *C12Q 1/70* | (2006.01) |
| *C12Q 1/6806* | (2018.01) |

(52) U.S. Cl.
CPC ........... *C12Q 1/6886* (2013.01); *C12Q 1/701* (2013.01); *C12Q 1/6806* (2013.01); *C12Q 1/6897* (2013.01); *C12Q 2600/158* (2013.01)

(56) References Cited

U.S. PATENT DOCUMENTS

| | | | |
|---|---|---|---|
| 11,124,846 | B2 | 9/2021 | Green et al. |
| 11,788,156 | B2 | 10/2023 | Green et al. |
| 2007/0072215 | A1 | 3/2007 | Seelig et al. |
| 2008/0268452 | A1 | 10/2008 | Kaplan et al. |
| 2014/0154744 | A1 | 6/2014 | Soll et al. |
| 2015/0275203 | A1 | 10/2015 | Green et al. |
| 2016/0244846 | A1 | 8/2016 | Weller et al. |
| 2017/0175111 | A1 | 6/2017 | Green et al. |
| 2017/0204477 | A1 | 7/2017 | Green et al. |
| 2022/0170116 | A1 | 6/2022 | Green et al. |

FOREIGN PATENT DOCUMENTS

| | | | | |
|---|---|---|---|---|
| WO | WO 2006/088165 | A1 | 8/2006 | |
| WO | WO 2009/066758 | A1 | 5/2009 | |
| WO | WO 2014/074648 | A2 | 5/2014 | |
| WO | WO 2016/011089 | A1 | 1/2016 | |
| WO | WO-2017205668 | A1 * | 11/2017 | ........... C12Q 1/6816 |
| WO | WO 2019/166816 | A1 | 9/2019 | |

OTHER PUBLICATIONS

Rakhra G and Rakhra G. Zinc finger proteins: insights into the transcriptional and post transcriptional regulation of immune response. Mol Biol Rep. Jul. 2021;48(7):5735-5743. Epub Jul. 24, 2021 (Year: 2021).*

Expression of ZNF175 in cancer [online]. Human Protein Atlas; 2025 [retrieved Jul. 17, 2025]. Retrieved from the Internet: https://www.proteinatlas.org/ENSG00000105497-ZNF175/cancer (Year: 2025).*

Goodman et al., Causes and effects of N-terminal codon bias in bacterial genes. Science. Oct. 25, 2013;342(6157):475-9. doi: 10.1126/science.1241934. Epub Sep. 26, 2013.

Meyer, The role of mRNA structure in bacterial translational regulation. Wiley Interdiscip Rev RNA. Jan. 2017;8(1). doi: 10.1002/wrna.1370. Epub Jun. 14, 2016.

Sauerwine et al., Kinetic Monte Carlo method applied to nucleic acid hairpin folding. Phys Rev E Stat Nonlin Soft Matter Phys. Dec. 2011;84(6 Pt 1):061912. doi: 10.1103/PhysRevE.84.061912. Epub Dec. 19, 2011.

Zuallaert et al., Interpretable convolutional neural networks for effective translation initiation site prediction. 2017 IEEE International Conference on Bioinformatics and Biomedicine (BIBM). 2017:1233-1237. doi: 10.1109/BIBM.2017.8217833.

Invitation to Pay Additional Fees mailed Aug. 27, 2021 for Application No. PCT/US2020/064695.

International Search Report and Written Opinion mailed Nov. 22, 2021 for Application No. PCT/US2020/064695.

International Preliminary Report on Patentability mailed Jun. 23, 2022 for Application No. PCT/US2020/064695.

Alley et al., Unified rational protein engineering with sequence-only deep representation learning. bioRxiv. Mar. 26, 2019. doi: 10.1101/589333. 52 pages.

Angenent-Mari et al., A deep learning approach to programmable RNA switches. Nat Commun. Oct. 7, 2020;11(1):5057. doi: 10.1038/s41467-020-18677-1.

Angermueller et al., Deep learning for computational biology. Mol Syst Biol. Jul. 29, 2016;12(7):878. doi: 10.15252/msb.20156651.

Aoki et al., Convolutional neural networks for classification of alignments of non-coding RNA sequences. Bioinformatics. Jul. 1, 2018;34(13):i237-i244. doi: 10.1093/bioinformatics/bty228.

Ausländer et al., Programmable single-cell mammalian biocomputers. Nature. Jul. 5, 2012;487(7405):123-7. doi: 10.1038/nature11149. Abstract only.

Babendure et al., Control of mammalian translation by mRNA structure near caps. RNA. May 2006;12(5):851-61. Epub Mar. 15, 2006.

Badelt et al., Thermodynamic and kinetic folding of riboswitches. Methods Enzymol. 2015;553:193-213. doi: 10.1016/bs.mie.2014.10.060. Epub Feb. 12, 2015.

Baek et al., LncRNAnet: long non-coding RNA identification using deep learning. Bioinformatics. Nov. 15, 2018;34(22):3889-3897. doi: 10.1093/bioinformatics/bty418.

Bailey et al., Dreme: motif discovery in transcription factor ChIP-seq data. Bioinformatics. Jun. 15, 2011;27(12):1653-9. doi: 10.1093/bioinformatics/btr261. Epub May 4, 2011.

Barrick et al., Quantitative analysis of ribosome binding sites in *E.coli*. Nucleic Acids Res. Apr. 11, 1994;22(7):1287-95.

Bashor et al., Using engineered scaffold interactions to reshape Map kinase pathway signaling dynamics. Science. Mar. 14, 2008;319(5869):1539-43. doi: 10.1126/science.1151153. Abstract only.

Bonnet et al., Amplifying genetic logic gates. Science. May 3, 2013;340(6132):599-603. doi: 10.1126/science.1232758. Epub Mar. 28, 2013. Abstract only.

Borujeni et al., Precise quantification of translation inhibition by mRNA structures that overlap with the ribosomal footprint in N-terminal coding sequences. Nucleic Acids Res. May 19, 2017;45(9):5437-5448. doi: 10.1093/nar/gkx061.

Borujeni et al., Translation Initiation is Controlled by RNA Folding Kinetics via a Ribosome Drafting Mechanism. J Am Chem Soc. Jun. 8, 2016;138(22):7016-23. doi: 10.1021/jacs.6b01453. Epub May 26, 2016.

Borujeni et al., Translation rate is controlled by coupled trade-offs between site accessibility, selective RNA unfolding and sliding at upstream standby sites. Nucleic Acids Res. Feb. 2014;42(4):2646-59. doi: 10.1093/nar/gkt1139. Epub Nov. 14, 2013.

Callura et al., Genetic switchboard for synthetic biology applications. Proc Natl Acad Sci U S A. Apr. 10, 2012;109(15):5850-5.

Camacho et al., Next-Generation Machine Learning for Biological Networks. Cell. Jun. 14, 2018;173(7):1581-1592. doi: 10.1016/j.cell.2018.05.015. Epub Jun. 7, 2018.

Cameron et al., A brief history of synthetic biology. Nat Rev Microbiol. May 2014;12(5):381-90. doi: 10.1038/nrmicro3239. Epub Apr. 1, 2014. Abstract only.

Canton et al., Refinement and standardization of synthetic biological parts and devices. Nat Biotechnol. Jul. 2008;26(7):787-93. doi: 10.1038/nbt1413. Abstract only.

Chuai et al., DeepCRISPR: optimized CRISPR guide RNA design by deep learning. Genome Biol. Jun. 26, 2018;19(1):80. doi: 10.1186/s13059-018-1459-4. 18 pages.

Culler et al., Reprogramming cellular behavior with RNA controllers responsive to endogenous proteins. Science. Nov. 26, 2010;330(6008):1251-5. doi: 10.1126/science.1192128.

Daniel et al., Synthetic analog computation in living cells. Nature. May 30, 2013;497(7451):619-23. doi: 10.1038/nature12148. Epub May 15, 2013. Abstract only.

(56) References Cited

OTHER PUBLICATIONS

Danino et al., A synchronized quorum of genetic clocks. Nature. Jan. 21, 2010;463(7279):326-30. doi: 10.1038/nature08753.

Delebecque et al., Organization of intracellular reactions with rationally designed RNA assemblies. Science. Jul. 22, 2011;333(6041):470-4. doi: 10.1126/science.1206938. Epub Jun. 23, 2011. Abstract only.

Dhawan et al., Pan-cancer characterisation of microRNA across cancer hallmarks reveals microRNA-mediated downregulation of tumour suppressors. Nat Commun. Dec. 7, 2018;9(1):5228. doi: 10.1038/s41467-018-07657-1.

Dirks et al., Paradigms for computational nucleic acid design. Nucleic Acids Res. Feb. 27, 2004;32(4):1392-403. doi: 10.1093/nar/gkh291.

Elowitz et al., A synthetic oscillatory network of transcriptional regulators. Nature. Jan. 20, 2000;403(6767):335-8. Abstract only.

Fiannaca et al., nRC: non-coding RNA Classifier based on structural features. BioData Min. Aug. 1, 2017;10:27. doi: 10.1186/s13040-017-0148-2.

Frosst et al., Distilling a Neural Network Into a Soft Decision Tree. Google Brain Team. arXiv Preprint. Nov. 27, 2017. arXiv:1711.09784v1 [cs.LG]. 8 pages.

Gardner et al., Construction of a genetic toggle switch in *Escherichia coli*. Nature. Jan. 20, 2000;403(6767):339-42. Abstract only.

Grabow et al., RNA modularity for synthetic biology. F1000Prime Rep. Nov. 1, 2013;5:46. doi: 10.12703/P5-46. eCollection 2013.

Green et al., Complex cellular logic computation using ribocomputing devices. Nature. Aug. 3, 2017;548(7665):117-121. doi: 10.1038/nature23271. Epub Jul. 26, 2017.

Green et al., Toehold switches: de-novo-designed regulators of gene expression. Cell. Nov. 6, 2014;159(4):925-39. doi: 10.1016/j.cell.2014.10.002. Epub Oct. 23, 2014.

Hunt et al., Ensembl variation resources. Database (Oxford). Jan. 1, 2018;2018:bay119. doi: 10.1093/database/bay119.

Isaacs et al., Engineered riboregulators enable post-transcriptional control of gene expression. Nat Biotechnol. Jul. 2004;22(7):841-7. Epub Jun. 20, 2004.

Isaacs et al., RNA synthetic biology. Nat Biotechnol. May 2006;24(5):545-54. doi: 10.1038/nbt1208.

Jäschke, Genetically encoded RNA photoswitches as tools for the control of gene expression. FEBS Lett. Jul. 16, 2012;586(15):2106-11. doi: 10.1016/j.febslet.2012.05.040. Epub May 31, 2012.

Jurtz et al., An introduction to deep learning on biological sequence data: examples and solutions. Bioinformatics. Nov. 15, 2017;33(22):3685-3690. doi: 10.1093/bioinformatics/btx531.

Khalil et al., A synthetic biology framework for programming eukaryotic transcription functions. Cell. Aug. 3, 2012;150(3):647-58.

Kim et al., Deep learning improves prediction of CRISPR-Cpf1 guide RNA activity. Nat Biotechnol. Mar. 2018;36(3):239-241. doi: 10.1038/nbt.4061. Epub Jan. 29, 2018.

Kim et al., De-Novo-Designed Translation-Repressing Riboregulators for Multi-Input Cellular Logic. Nat Chem Biol. Dec. 2019;15(12):1173-82. doi:10.1038/s41589-019-0388-1. Author Manuscript.

Kim et al., Modulating Responses of Toehold Switches by an Inhibitory Hairpin. ACS Synth Biol. Mar. 15, 2019;8(3):601-605. doi: 10.1021/acssynbio.8b00488. Epub Feb. 15, 2019.

Koo et al., Representation learning of genomic sequence motifs with convolutional neural networks. PLoS Comput Biol. Dec. 19, 2019;15(12):e1007560. doi: 10.1371/journal.pcbi.1007560.

Krishnamurthy et al., Tunable Riboregulator Switches for Post-transcriptional Control of Gene Expression. ACS Synth Biol. Dec. 18, 2015;4(12):1326-34. doi: 10.1021/acssynbio.5b00041. Epub Jul. 27, 2015. 31 pages.

Kudla et al., Coding-sequence determinants of gene expression in *Escherichia coli*. Science. Apr. 10, 2009;324(5924):255-8.

Lebars et al., LNA derivatives of a kissing aptamer targeted to the trans-activating responsive RNA element of HIV-1. Blood Cells, Molecules and Diseases. 2007;38:204-9.

Liu et al., An adaptor from translational to transcriptional control enables predictable assembly of complex regulation. Nat Methods. Nov. 2012;9(11):1088-94. doi: 10.1038/nmeth.2184. Epub Sep. 30, 2012. Abstract only.

Liu et al., Prediction of Long Non-Coding RNAs Based on Deep Learning. Genes (Basel). Apr. 3, 2019;10(4):273. doi: 10.3390/genes10040273.

Lorenz et al., ViennaRNA Package 2.0. Algorithms Mol Biol. Nov. 24, 2011;6:26. doi: 10.1186/1748-7188-6-26.

Lucks et al., Versatile RNA-sensing transcriptional regulators for engineering genetic networks. Proc Natl Acad Sci U S A. May 24, 2011;108(21):8617-22. doi: 10.1073/pnas.1015741108. Epub May 9, 2011.

Luo et al., Prediction of activity and specificity of CRISPR-Cpf1 using convolutional deep learning neural networks. BMC Bioinformatics. Jun. 13, 2019;20(1):332. doi: 10.1186/s12859-019-2939-6. 10 pages.

Ma et al., Low-cost detection of norovirus using paper-based cell-free systems and synbody-based viral enrichment. Synth Biol (Oxf). 2018;3(1):ysy018. doi: 10.1093/synbio/ysy018. Epub Sep. 19, 2018. 11 pages.

Matthews et al., Expanded sequence dependence of thermodynamic parameters improves prediction of RNA secondary structure. J Mol Biol. May 21, 1999;288(5):911-40. Abstract only.

Moon et al., Genetic programs constructed from layered logic gates in single cells. Nature. Nov. 8, 2012;491(7423):249-53.

Mutalik et al., Rationally designed families of orthogonal RNA regulators of translation. Nat Chem Biol. Mar. 25, 2012;8(5):447-54. doi: 10.1038/nchembio.919.

Narita et al., Cis-regulatory hairpin-shaped mRNA encoding a reporter protein: catalytic sensing of nucleic acid sequence at single nucleotide resolution. Nat Protoc. 2007:2(5):1105-16. Epub May 3, 2007.

Narita et al., Highly sensitive genotyping using artificial riboregulator system. Nucleic Acids Symp Ser No. 49. 2005;271-2.

Oberacker et al., Bio-On-Magnetic-Beads (BOMB): Open platform for high-throughput nucleic acid extraction and manipulation. PLoS Biol. Jan. 10, 2019;17(1):e3000107. doi: 10.1371/journal.pbio.3000107.

Pardee et al., Paper-based synthetic gene networks. Cell. Nov. 6, 2014;159(4):940-54 and Supplemental Info. doi: 10.1016/j.cell.2014.10.004. Epub Oct. 23, 2014. 22 pages.

Pardee et al., Rapid, Low-Cost Detection of Zika Virus Using Programmable Biomolecular Components. Cell. May 19, 2016;165(5):1255-1266 and Supplemental Info. doi: 10.1016/j.cell.2016.04.059. Epub May 6, 2016. 23 pages.

Qian et al., Neural network computation with DNA strand displacement cascades. Nature. Jul. 20, 2011;475(7356):368-72.

Qian et al., Scaling up digital circuit computation with DNA strand displacement cascades. Science. Jun. 3, 2011;332(6034):1196-201.

Reeve et al., Predicting translation initiation rates for designing synthetic biology. Front Bioeng Biotechnol. Jan. 20, 2014;2:1. doi: 10.3389/fbioe.2014.00001.

Rinaudo et al., A universal RNAi-based logic evaluator that operates in mammalian cells. Nat Biotechnol. Jul. 2007;25(7):795-801. Epub May 21, 2007.

Rodrigo et al., De novo automated design of small RNA circuits for engineering synthetic riboregulation in living cells. Proc Natl Acad Sci U S A. Sep. 18, 2012;109(38):15271-6. Epub Sep. 4, 2012.

Ruder et al., Synthetic biology moving into the clinic. Science. Sep. 2, 2011;333(6047):1248-52. doi: 10.1126/science.1206843. Abstract only.

Salis et al., Automated design of synthetic ribosome binding sites to control protein expression. Nat Biotechnol. Oct. 2009;27(10):946-50. doi: 10.1038/nbt.1568. Epub Oct. 4, 2009.

Sando et al., Doubly catalytic sensing of HIV-1-related CCR5 sequence in prokaryotic cell-free translation system using riboregulator-controlled luciferase activity. J Am Chem Soc. 2005;127:5300-1.

Simonyan et al., Deep Inside Convolutional Networks: Visualising Image Classification Models and Saliency Maps. Visual Geometry Group, University of Oxford. arXiv Preprint. 2013. arXiv:1312.6034v2 [cs.CV]. 8 pages.

(56) References Cited

OTHER PUBLICATIONS

Takahashi et al., A low-cost paper-based synthetic biology platform for analyzing gut microbiota and host biomarkers. Nat Commun. Aug. 21, 2018;9(1):3347. doi: 10.1038/s41467-018-05864-4.

Takahashi et al., A modular strategy for engineering orthogonal chimeric RNA transcription regulators. Nucleic Acids Res. Aug. 2013;41(15):7577-88.

Tamsir et al., Robust multicellular computing using genetically encoded NOR gates and chemical 'wires'. Nature. Jan. 13, 2011;469(7329):212-5. doi: 10.1038/nature09565. Epub Dec. 8, 2010.

To et al., A comprehensive web tool for toehold switch design. Bioinformatics. Aug. 15, 2018;34(16):2862-2864. doi: 10.1093/bioinformatics/bty216.

Vimberg et al., Translation initiation region sequence preferences in *Escherichia coli*. BMC Mol Biol. Oct. 31, 2007;8:100, 13 pages.

Wainberg et al., Deep learning in biomedicine. Nat Biotechnol. Oct. 2018;36(9):829-838. doi: 10.1038/nbt.4233. Epub Sep. 6, 2018.

Webb, Deep learning for biology. Nature. Feb. 2018;554(7693):555-557. doi: 10.1038/d41586-018-02174-z.

Win et al., Higher-order cellular information processing with synthetic RNA devices. Science. Oct. 17, 2008;322(5900):456-60. doi: 10.1126/science.1160311.

Xie et al., Multi-input RNAi-based logic circuit for identification of specific cancer cells. Science. Sep. 2, 2011;333(6047):1307-11. doi: 10.1126/science.1205527. Abstract only.

Yang et al., STAT3 overexpression promotes metastasis in intrahepatic cholangiocarcinoma and correlates negatively with surgical outcome. Oncotarget. Jan. 31, 2017;8(5):7710-7721. doi: 10.18632/oncotarget.13846.

Zadeh et al., Nucleic acid sequence design via efficient ensemble defect optimization. J Comput Chem. Feb. 2011;32(3):439-52. doi: 10.1002/jcc.21633. Epub Aug. 17, 2010. Abstract only.

Zadeh et al., Nupack: Analysis and design of nucleic acid systems. J Comput Chem. Jan. 15, 2011;32(1):170-3. doi: 10.1002/jcc.21596. Abstract only.

Zhang et al., Control of DNA strand displacement kinetics using toehold exchange. J Am Chem Soc. Dec. 2, 2009;131(47):17303-14. doi: 10.1021/ja906987s. Abstract only.

Zhang et al., Dynamic DNA nanotechnology using strand-displacement reactions. Nature Chemistry 3, 103-113 (2011) doi:10.1038/nchem.957. Abstract only.

Zhang et al., Titer: predicting translation initiation sites by deep learning. Bioinformatics. Jul. 15, 2017;33(14):1234-1242. doi: 10.1093/bioinformatics/btx247. 9 pages.

Zhang et el., Function of hexameric RNA in packaging of bacteriophage phi 29 DNA in vitro. Mol Cell. Jul. 1998;2(1):141-7.

Cambray et al., Evaluation of 244,000 synthetic sequences reveals design principles to optimize translation in *Escherichia coli*. Nat Biotechnol. Nov. 2018;36(10):1005-1015. doi: 10.1038/nbt.4238. Epub Sep. 24, 2018. With supplemental information.

Groher et al. Tuning the Performance of Synthetic Riboswitches using Machine Learning. ACS Synth Biol. Jan. 18, 2019;8(1):34-44. doi: 10.1021/acssynbio.8b00207. Epub Jan. 8, 2019.

Höllerer et al., Large-scale DNA-based phenotypic recording and deep learning enable highly accurate sequence-function mapping. Nat Commun. Jul. 15, 2020;11(1):3551. doi: 10.1038/s41467-020-17222-4.

Kelley et al., Basset: learning the regulatory code of the accessible genome with deep convolutional neural networks. Genome Res. Jul. 2016;26(7):990-9. doi: 10.1101/gr.200535.115. Epub May 3, 2016.

Kinney et al., Massively Parallel Assays and Quantitative Sequence-Function Relationships. Annu Rev Genomics Hum Genet. Aug. 31, 2019;20:99-127. doi: 10.1146/annurev-genom-083118-014845. Epub May 15, 2019.

Kinney et al., Using deep sequencing to characterize the biophysical mechanism of a transcriptional regulatory sequence. Proc Natl Acad Sci U S A. May 18, 2010;107(20):9158-63. doi: 10.1073/pnas.1004290107. Epub May 3, 2010.

Lehr et al., Cell-Free Prototyping of AND-Logic Gates Based on Heterogeneous RNA Activators. ACS Synth Biol. Sep. 20, 2019;8(9):2163-2173. doi: 10.1021/acssynbio.9b00238. Epub Aug. 27, 2019.

Peterman et al., Sort-seq under the hood: implications of design choices on large-scale characterization of sequence-function relations. BMC Genomics. Mar. 9, 2016:17:206. doi: 10.1186/s12864-016-2533-5.

Singh et al. RNA secondary structure prediction using an ensemble of twodimensional deep neural networks and transfer learning. Nat Commun. Nov. 27, 2019;10(1):5407. doi: 10.1038/s41467-019-13395-9.

Valeri et al., Sequence-to-function deep learning frameworks for engineered riboregulators. Nat Commun. Oct. 7, 2020;11(1):5058. doi: 10.1038/s41467-020-18676-2.

* cited by examiner $$R_i = \sum_j \frac{a_i w_{ij}^+}{\sum_i a_i w_{ij}^+} R_j$$

Representative Individual Toehold Switch Saliency Maps

Learned Feature Diversity

Full Toehold Library
Averaged MFE Structures

Full Toehold Library
Averaged Saliency Map (Learned features)

RIBOREGULATORS AND METHODS OF USE THEREOF

RELATED APPLICATIONS

This application is a national stage filing under 35 U.S.C. § 371 of International Patent Application Serial No. PCT/US2020/064695, filed Dec. 11, 2020, which claims the benefit under 35 U.S.C. § 119(e) of U.S. Provisional Application Ser. No. 62/948,175, filed Dec. 13, 2019, entitled "RIBOREGULATORS AND METHODS OF USE THEREOF", the entire contents of each of which are incorporated by reference herein.

FEDERALLY SPONSORED RESEARCH

This invention was made with U.S. Government support under DE-FG02-02ER63445 awarded by the U.S. Department of Energy and HDTRA1-14-1-0006 awarded by the Department of Defense/Defense Advanced Research Projects Agency. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 10, 2022, is named H049870709US01-SEQ-MAT, and is 69,080,020 bytes in size.

BACKGROUND OF INVENTION

Engineered ribonucleic acid (RNA) molecules with targeted biological functions play an important role in synthetic biology (1), particularly as programmable response elements for small molecules, proteins, and nucleic acids. Examples include riboswitches, riboregulators, and ribozymes, many of which hold great promise for a variety of in vitro and in vivo applications (1, 2).

Toehold riboregulators are a class of versatile prokaryotic riboregulators inducible by the presence of a fully programmable trans-RNA trigger sequence (2-6, 15, 16). These RNA synthetic biology modules have displayed impressive dynamic range and orthogonality when used both in vivo as genetic circuit components (2, 5, 6), and in vitro as nucleic acid diagnostic tools using cell-free protein synthesis (CFPS) systems (3, 4, 15, 16).

SUMMARY OF INVENTION

This disclosure provides novel toehold riboregulators and uses thereof. The toehold riboregulators are specific for a particular viral nucleic acid or a particular human transcription factor nucleic acid. The toehold riboregulators may be used to detect the presence of and/or measure the level of such nucleic acids. The presence and/or level of such nucleic acids may be associated with a viral infection or another condition such as a cancer.

Thus, in one aspect, this disclosure provides a toehold riboregulator comprising (a) a nucleic acid sequence comprising any one of SEQ ID NOs: 1-244,000, or (b) nucleotides 21-103 of any one of SEQ ID NOs: 1-244,000, or (c) nucleotides 21-100 of any one of SEQ ID NOs: 1-244,000, or (d) RNA versions of (a), (b) or (c).

In a related aspect, this disclosure provides a toehold riboregulator comprising (a) a nucleic acid sequence comprising any one of SEQ ID Nos: 164989, 43841, 9602, 40182, 62866, 111698, 236638, and 19367, or (b) nucleotides 21-103 of any one of SEQ ID NOs: 164989, 43841, 9602, 40182, 62866, 111698, 236638, and 19367, or (c) nucleotides 21-100 of any one of SEQ ID NOs: 164989, 43841, 9602, 40182, 62866, 111698, 236638, and 19367, or (d) RNA versions of (a), (b) or (c).

In another related aspect, this disclosure provides a toehold riboregulator comprising (a) a nucleic acid sequence comprising any one of SEQ ID Nos: 43841, 9602, 62866, and 19367, or (b) nucleotides 21-103 of any one of SEQ ID NOs: 43841, 9602, 62866, and 19367, or (c) nucleotides 21-100 of any one of SEQ ID NOs: 43841, 9602, 62866, and 19367, or (d) RNA versions of (a), (b) or (c).

In another related aspect, this disclosure provides a toehold riboregulator comprising (a) a nucleic acid sequence comprising any one of SEQ ID Nos: 43841 and 62866, or (b) nucleotides 21-103 of any one of SEQ ID NOs: 43841 and 62866, or (c) nucleotides 21-100 of any one of SEQ ID NOs: 43841 and 62866, or (d) RNA versions of (a), (b) or (c).

Any one of these toehold riboregulators may be covalently attached (or conjugated or operably linked), at its 3' end, to a nucleic acid encoding a reporter protein or reporter RNA.

In some embodiments, as defined herein, the riboregulator is specific for a virus selected from the group consisting of astrovirus, cardiovirus, chikungunya virus, cosavirus, coxsackie virus, dengue virus, ebola virus, hantavirus, human immunodeficiency virus, human parvo virus, human rhino virus, influenza virus: h1n1, influenza virus: h3n2, lassa virus, leishmanial virus, Marburg virus, papilloma virus, poliovirus, rabies virus, smallpox virus, west nile virus, yellow fever virus, an zika virus.

In some embodiments, as defined herein, the riboregulator is specific for a virus selected from the group consisting of dengue virus, human rhino virus, or smallpox virus.

In some embodiments, as defined herein, the riboregulator is specific for dengue virus.

In some embodiments, as defined herein, the riboregulator is specific for human rhino virus.

In some embodiments, as defined herein, the riboregulator is specific for smallpox virus.

In some embodiments, as defined herein, the riboregulator is SEQ ID NO: 43841 and it is it used to detect smallpox virus.

In some embodiments, as defined herein, the riboregulator is SEQ ID NO: 9602 and it is it used to detect dengue virus.

In some embodiments, as defined herein, the riboregulator is SEQ ID NO: 62866 and it is it used to detect smallpox virus.

In some embodiments, as defined herein, the riboregulator is SEQ ID NO: 19367 and it is it used to detect human rhino virus.

The nucleotide sequence of SEQ ID NO: 43841 is
TAATACGACT CACTATAGGG CTTCCTTTTC GTTGATCTCT

CATAGATTTA AACAGAGGAG ATAAATCATG GAGAGATCAA

ACCTGGCGGC AGCGCAAAAG ATG.

The nucleotide sequence of SEQ ID NO: 9602 is
TAATACGACT CACTATAGGG GGGTCTCAGC CACTTCCTTC

TCTAACTTGA AACAGAGGAG ATCAAGTATG AGAAGGAAGA

ACCTGGCGGC AGCGCAAAAG ATG.

The nucleotide sequence of SEQ ID NO: 62866 is
TAATACGACT CACTATAGGG GTCAATACCT AACTCCAATT

TTCAGTGATT AACAGAGGAG AAATCACATG AAATTGGAGA

ACCTGGCGGC AGCGCAAAAG ATG.

The nucleotide sequence of SEQ ID NO: 19367 is
TAATACGACT CACTATAGGG TTCTTCTCCT ATCTTCTTCC

TTTATATGAC AACAGAGGAG AGTCATAATG AGGAAGAAGA

ACCTGGCGGC AGCGCAAAAG ATG.

In some embodiments, as defined herein, the riboregulator is specific for a human transcription factor selected from the group consisting of AC097634.4, ACTB, ACTL6A, ACTN4, AEBP1, AEBP2, AGO1, AGO2, AHR, AIRE, AKNA, AL121581.1, ALX1, ALX4, ANHX, AR, ARHGAP35, ARID3A, ARID3B, ARID3C, ARID4A, ARID4B, ARID5A, ARID5B, ARNT, ARNT2, ARNTL, ARNTL2, ARRB1, ARX, ASCL1, ASCL2, ASCL3, ASCL4, ASCL5, ASH2L, ATF1, ATF2, ATF3, ATF4, ATF5, ATF6, ATF6B, ATMIN, ATOH1, ATOH8, ATXN3, BACH1, BACH2, BARHL1, BARHL2, BARX1, BARX2, BASP1, BATF, BATF2, BATF3, BAZ2A, BCL11A, BCL11B, BCL6, BCL6B, BCOR, BHLHA15, BHLHE40, BHLHE41, BORCS8-MEF2B, BRCA1, BRD7, BRF2, CALCOCO1, CARF, CARM1, CBX4, CC2D1A, CC2D1B, CCAR1, CCNT1, CDC5L, CDK12, CDK13, CDK5RAP2, CDK9, CDX1, CDX2, CDX4, CEBPA, CEBPB, CEBPD, CEBPE, CEBPG, CEBPZ, CGGBP1, CHD2, CHD4, CHD7, CIART, CIITA, CITED1, CLOCK, CNBP, CREB1, CREB3, CREB3L1, CREB3L2, CREB3L3, CREB3L4, CREBBP, CREBRF, CREM, CRX, CRY1, CRY2, CT476828.9, CTCF, CTCFL, CUX1, CUX2, CXXC1, DACH1, DBP, DDIT3, DDN, DEAF1, DHX36, DHX9, DLX1, DLX2, DLX4, DLX5, DMBX1, DMRT1, DMRT2, DNMT3A, DPF2, DR1, DRAP1, DUX4, E2F1, E2F2, E2F3, E2F4, E2F6, E2F7, E2F8, E4F1, EAF2, EBF2, EBF3, EBF4, EED, EGR1, EGR2, EGR3, EGR4, EHF, EHMT2, ELF1, ELF3, ELF4, ELF5, ELK1, ELK3, ELK4, ELL3, ELMSAN1, EN1, ENO1, EOMES, EP300, ERBB4, ERG, ESR1, ESR2, ESRRA, ESRRB, ESRRG, ESX1, ETS1, ETS2, ETV1, ETV2, ETV3, ETV4, ETV5, ETV6, ETV7, EZH2, FERD3L, FEZF1, FEZF2, FIGLA, FLI1, FOS, FOSB, FOSL1, FOSL2, FOXA1, FOXA2, FOXA3, FOXC1, FOXC2, FOXD1, FOXD3, FOXF1, FOXF2, FOXH1, FOXI1, FOXJ1, FOXJ2, FOXK1, FOXK2, FOXL2, FOXM1, FOXN4, FOXO3, FOXP2, FOXP3, FOXQ1, FOXS1, FUBP3, GABPA, GABPB1, GABPB2, GADD45A, GATA1, GATA2, GATA3, GATA4, GATA5, GATA6, GATAD2B, GBX2, GCFC2, GCM1, GFI1, GLI1, GLI2, GLI3, GLIS1, GLIS2, GLMP, GMEB1, GMEB2, GRHL1, GRHL2, GSC, GSX1, GTF2B, GTF3C1, GZF1, H2AFY, H2AFY2, H2AFZ, H3F3A, H3F3B, HAND1, HAND2, HDAC1, HDAC2, HDAC4, HDAC5, HDAC6, HELT, HES1, HES2, HES3, HES4, HES5, HES6, HES7, HESX1, HEY1, HEY2, HEYL, HHEX, HIC2, HIF1A, HINFP, HIVEP1, HLF, HLTF, HMGA1, HMGA2, HMGB1, HMGB2, HMX1, HMX3, HNF1A, HNF1B, HNF4A, HNF4G, HNRNPC, HNRNPK, HNRNPL, HNRNPU, HOXA10, HOXA2, HOXA3, HOXA4, HOXA5, HOXA6, HOXA7, HOXA9, HOXB1, HOXB2, HOXB3, HOXB4, HOXB5, HOXB6, HOXB7, HOXB9, HOXC10, HOXC11, HOXC4, HOXC5, HOXC6, HOXD10, HOXD13, HOXD3, HOXD4, HOXD8, HOXD9, HR, HSF1, HSF2, HSF4, HSF5, HSFX1, HSFX2, HSFX3, HSFX4, HSFY1, HSFY2, IER2, IFI16, IKZF1, IKZF2, IKZF3, IKZF4, IKZF5, INSM1, IRF1, IRF2, IRF2BP1, IRF2BP2, IRF2BPL, IRF3, IRF4, IRF5, IRF6, IRF7, IRF8, IRF9, ISL1, JARID2, JDP2, JMJD1C, JUN, JUNB, JUND, KAT2B, KAT7, KCNIP3, KDM1A, KDM2B, KDM3A, KDM3B, KDM5A, KDM6A, KDM6B, KLF1, KLF10, KLF11, KLF12, KLF13, KLF15, KLF16, KLF17, KLF3, KLF4, KLF5, KLF6, KLF7, KLF8, KMT2A, KMT2D, LDB1, LEF1, LHX2, LHX3, LITAF, LMO2, LMO4, LMX1A, LMX1B, LONP1, LRRFIP1, LYL1, MACC1, MAF, MAF1, MAFA, MAFB, MAFF, MAFG, MAFK, MAX, MAZ, MBD2, MBD3, MED1, MED12, MED8, MEF2A, MEF2B, MEF2C, MEF2D, MEIS1, MEIS2, MEN1, MEOX1, MEOX2, MESP1, MESP2, MITF, MIXL1, MLX, MLXIP, MLXIPL, MMP12, MNT, MRTFA, MSC, MSGN1, MSX1, MSX2, MTA1, MTA2, MTERF3, MTF1, MTF2, MTOR, MUC1, MXD1, MXD3, MXI1, MYB, MYBBP1A, MYBL1, MYBL2, MYC, MYCN, MYEF2, MYF5, MYF6, MYOCD, MYOD1, MYOG, MYPOP, MYT1, MYT1L, MZF1, NACC2, NANOG, NCOA2, NCOR1, NCOR2, NDN, NEUROD1, NEUROD2, NEUROD6, NEUROG1, NEU-ROG2, NEUROG3, NFAT5, NFATC1, NFATC2, NFATC3, NFATC4, NFE2, NFE2L1, NFE2L2, NFE2L3, NFIA, NFIB, NFIC, NFIL3, NFKB1, NFKB2, NFX1, NFXL1, NFYA, NFYB, NFYC, NHLH1, NHLH2, NKRF, NKX2-1, NKX2-2, NKX2-5, NKX2-6, NKX2-8, NKX3-1, NKX3-2, NKX6-1, NKX6-2, NLRC5, NME1, NONO, NOTCH1, NPAS2, NPAS4, NPM1, NR1D1, NR1D2, NR1H2, NR1H3, NR1H4, NR1I2, NR1I3, NR2C1, NR2C2, NR2E3, NR2F1, NR2F6, NR3C1, NR4A1, NR4A2, NR4A3, NR5A1, NR5A2, NR6A1, NRF1, NRIP1, NRL, NSD1, ONECUT2, ONECUT3, OSR1, OSR2, OTX1, OTX2, OVOL1, PARP1, PATZ1, PAX1, PAX2, PAX4, PAX5, PAX6, PAX8, PAX9, PAXBP1, PBX1, PBX2, PBX3, PCGF3, PCGF5, PCGF6, PDX1, PER1, PER2, PER3, PGR, PHB, PHOX2A, PHOX2B, PIH1D1, PITX1, PITX2, PITX3, PKNOX2, PLAG1, PLAGL1, POLRMT, POU1F1, POU2AF1, POU2F1, POU2F2, POU2F3, POU3F2, POU3F4, POU4F1, POU4F2, POU4F3, POU5F1, POU6F1, PPARA, PPARD, PPARG, PRDM1, PRDM11, PRDM12, PRDM13, PRDM14, PRDM15, PRDM2, PRDM4, PRDM5, PRDM6, PRDM7, PRDM9, PRDX5, PRKN, PRMT5, PROP1, PROX1, PRRX1, PSPC1, PTF1A, PURA, PURB, PURG, RAI1, RARA, RARB, RARG, RAX, RAX2, RB1, RBBP4, RBBP5, RBL1, RBL2, RBMX, RBPJ, RBPJL, RCOR1, RCOR2, RCOR3, REL, RELA, RELB, REST, RFX1, RFX2, RFX3, RFX4, RFX5, RFX6, RFX7, RFX8, RNF10, RORA, RORB, RORC, RPS3, RPTOR, RREB1, RRN3, RUNX1, RUNX2, RUNX3, RUVBL2, RXRA, RXRB, SAFB, SALL1, SALL2, SARS, SATB1, SATB2, SCRT1, SCRT2, SCX, SETX, SFPQ, SIN3A, SIRT1, SIX1, SIX2, SIX3, SIX4, SIX5, SIX6, SKIL, SMAD1, SMAD2, SMAD3, SMAD4, SMAD5, SMAD6, SMAD7, SMARCA2, SMARCA4, SMARCB1, SMARCC1, SMARCC2, SMARCD2, SMARCE1, SMYD3, SNAI1, SNAI2, SNAI3, SNCA, SOX1, SOX10, SOX11, SOX12, SOX13, SOX17, SOX18, SOX2, SOX21, SOX3, SOX4, SOX6, SOX7, SOX8, SOX9, SP1, SP2, SP3, SP5, SP7, SPI1, SPIB, SPIC, SREBF1, SREBF2, SRF, SSBP2, SSBP3, SSBP4, ST18, STAT1, STAT3, STAT5B, STAT6, STOX1, SUV39H1, SUV39H2, SUZ12, TAF1, TAF1B, TAF1C, TAF2, TAF5, TAF7, TAF7L, TAF9, TAF9B, TAL1, TAL2, TBL1X, TBL1XR1, TBP, TBPL1, TBPL2, TBR1, TBX15, TBX18, TBX19, TBX2, TBX20, TBX21, TBX22, TBX3, TBX5, TBX6, TBXT, TCF12, TCF15, TCF20, TCF21, TCF3, TCF4, TCF7, TCF7L1, TCF7L2, TCFL5, TEAD1, TEAD2, TEAD3, TEAD4, TEF, TFAM, TFAP2A, TFAP2B, TFAP2C, TFAP2D, TFAP2E, TFAP4, TFCP2, TFCP2L1, TFDP1, TFDP2, TFE3, TFEB, TFEC, TGIF1, THAP1, THAP11, THRA, THRAP3, THRB, TIPARP, TLX1, TNF, TOP1, TOX2, TOX3, TP53, TP63, TP73, TRERF1, TRIM24, TRPS1, TWIST1, TXK, UBTF, UHRF1, USP3, UTY, VAX1, VAX2, VDR, VEZF1, WBP2, WNT1, WNT11, WNT5A, WT1, XBP1, XRCC5, XRCC6, XRN2, YAP1, YBX1, YBX3, YY1, YY2, ZBED1, ZBTB14, ZBTB16, ZBTB17, ZBTB2, ZBTB20, ZBTB24, ZBTB4, ZBTB48, ZBTB5, ZBTB7A, ZBTB7B, ZC3H4, ZC3H6, ZC3H8, ZEB1, ZFHX2, ZFHX3, ZFHX4, ZFP42, ZFPM1, ZGPAT, ZHX3, ZIC1, ZIC2, ZIC3, ZIC4, ZIC5, ZKSCAN3, ZNF131, ZNF143, ZNF148, ZNF174, ZNF175, ZNF202, ZNF205, ZNF217, ZNF219, ZNF239, ZNF277, ZNF281, ZNF322, ZNF335, ZNF350, ZNF395, ZNF431, ZNF497, ZNF501, ZNF513, ZNF516, ZNF536, ZNF541, ZNF564, ZNF568, ZNF589, ZNF605, ZNF613, ZNF639, ZNF649, ZNF658, ZNF668, ZNF691, ZNF692, ZNF704, ZNF709, ZNF711, ZNF740, ZNF746, ZNF750, ZNF821, ZNF835, ZNF93, and ZSCAN21.

In some embodiments, as defined herein, the riboregulator is specific for a human transcription factor selected from the group consisting of NCOR1, E2F3 and ZNF175.

In some embodiments, as defined herein, the riboregulator is SEQ ID NO: 164989 and it is used to detect human transcription factor NCOR1.

In some embodiments, as defined herein, the riboregulator is SEQ ID NO: 111698 and it is used to detect human transcription factor E2F3.

In some embodiments, as defined herein, the riboregulator is SEQ ID NO: 236638 and it is used to detect human transcription factor ZNF175.

```
The nucleotide sequence of SEQ ID NO: 164989 is
TAATACGACT CACTATAGGG CCCTTTGTTT TCTTGCATGA

TTTCTTCTTT AACAGAGGAG AAAAGAAATG ATCATGCAAA

ACCTGGCGGC AGCGCAAAAG ATG.

The nucleotide sequence of SEQ ID NO: 111698 is
TAATACGACT CACTATAGGG TATCTTGATA TGTAACATAA

GCTAACCTTT AACAGAGGAG AAAAGGTATG CTTATGTTAA

ACCTGGCGGC AGCGCAAAAG ATG.

The nucleotide sequence of SEQ ID NO: 236638 is
TAATACGACT CACTATAGGG TGGAACACCA TGAACCATCT

CTTGTGAACT AACAGAGGAG AAGTTCAATG GAGATGGTTA

ACCTGGCGGC AGCGCAAAAG ATG.
```

In some embodiments, the riboregulator is specific for the human transcription factor STAT3.

In another aspect, this disclosure provides a method comprising contacting a sample with any of the foregoing toehold riboregulator conjugated to a reporter domain under conditions sufficient to allow the toehold riboregulator to hybridize to its respective trigger nucleic acid, and detecting and optionally measuring expression of the reporter domain product (e.g., reporter protein or reporter RNA). Detection of the trigger nucleic acid may indicate that the subject from whom the sample was derived has an infection of one of the foregoing viruses or has been exposed to such virus(es) or has a cancer associated with upregulated expression of one of the foregoing transcription factors.

In some embodiments, the sample is obtained from a human subject.

In some embodiments, the subject is suspected of having cancer.

In some embodiments, the subject is suspected of having an infection of one of the foregoing viruses.

In some embodiments, the subject is suspected of having a smallpox virus infection, a dengue virus infection, or a human rhino virus infection.

In some embodiments, the subject is suspected of having a smallpox virus infection.

In some embodiments, the subject is suspected of having a dengue virus infection.

In some embodiments, the subject is suspected of having a human rhino virus infection.

In some embodiments, the subject is suspected of having been exposed to smallpox virus, dengue virus, or human rhino virus.

In some embodiments, the subject is suspected of having been exposed to smallpox virus.

In some embodiments, the subject is suspected of having been exposed to dengue virus.

In some embodiments, the subject is suspected of having been exposed to human rhino virus.

In another aspect, this disclosure provides a method of treating a subject, comprising administering an effective amount of an anti-viral agent to a subject having a viral infection, wherein the subject is identified as having a viral infection by detecting viral mRNA in a sample from the subject using any of the foregoing viral-specific toehold riboregulators.

In another aspect, this disclosure provides a method of treating a subject, comprising administering an effective amount of an anti-cancer agent to a subject having a cancer, wherein the subject is identified as having a cancer by detecting increased mRNA expression of a human transcription factor in a sample from the subject using any of the foregoing transcription-factor specific toehold riboregulators.

A related aspect of this disclosure provides a toehold riboregulator having
    (a) a nucleic acid sequence comprising any one of SEQ ID NOs: 43841, 9602, 62866, 19367, 164989, 111698, and 236638, or
    (b) nucleotides 21-103 of any one of SEQ ID NOs: 43841, 9602, 62866, 19367, 164989, 111698, and 236638, or
    (c) nucleotides 21-100 of any one of SEQ ID NOs: 43841, 9602, 62866, 19367, 164989, 111698, and 236638, or
    (d) RNA versions of (a), (b) or (c).

In some embodiments, the toehold riboregulator is covalently attached, at its 3' end, to a nucleic acid encoding a reporter protein or reporter RNA.

In some embodiments, the toehold riboregulator is specific for dengue virus, human rhino virus, or smallpox virus.

In some embodiments, the toehold riboregulator is specific for a human mRNA encoding a transcription factor selected from E2F3, NCOR1, or ZNF175.

In some embodiments, the toehold riboregulator comprises a nucleotide sequence of any one of SEQ ID NOs: 43841, 9602, 62866, and 19367. In some embodiments, the toehold riboregulator comprises a nucleotide sequence of SEQ ID NO: 43841. In some embodiments, the toehold riboregulator comprises a nucleotide sequence of SEQ ID NO: 9602. In some embodiments, the toehold riboregulator comprises a nucleotide sequence of SEQ ID NO: 62866. In some embodiments, the toehold riboregulator comprises a nucleotide sequence of SEQ ID NO: 19367. In some embodiments, the toehold riboregulator is a plurality of toehold riboregulators comprising a toehold riboregulator comprising a nucleotide sequence of SEQ ID NO: 43841 and a toehold riboregulator comprising a nucleotide sequence of SEQ ID NO: 62866.

Another related aspect of this disclosure provides a method comprising contacting a sample with any one or more of the foregoing toehold riboregulators, covalently attached, at its 3' end, to a nucleic acid encoding a reporter protein or reporter RNA, under conditions sufficient to allow the toehold riboregulator to hybridize to its respective trigger nucleic acid, and detecting and optionally measuring expression of the reporter protein or reporter RNA.

In some embodiments, the sample is obtained from a human subject. In some embodiments, the subject is suspected of having cancer. In some embodiments, the subject is suspected of having a viral infection. In some embodiments, the subject is suspected of having come into contact with a virus, such as smallpox virus, dengue virus, or human rhino virus.

In some embodiments, the toehold riboregulator comprises a nucleotide sequence of any one of SEQ ID NOs: 43841, 9602, 62866, and 19367.

In some embodiments, the toehold riboregulator comprises a nucleotide sequence of SEQ ID NO: 43841. In some embodiments, the toehold riboregulator comprises a nucleotide sequence of SEQ ID NO: 9602. In some embodiments, the toehold riboregulator comprises a nucleotide sequence of SEQ ID NO: 62866. In some embodiments, the toehold riboregulator comprises a nucleotide sequence of SEQ ID NO: 19367. In some embodiments, the toehold riboregulator comprises a toehold riboregulator comprising a nucleotide sequence of SEQ ID NO: 43841 and a toehold riboregulator comprising a nucleotide sequence of SEQ ID NO: 62866.

In some embodiments, the subject is suspected of having a smallpox virus infection or having been exposed to smallpox virus. In some embodiments, the subject is suspected of having dengue virus infection or having been exposed to dengue virus. In some embodiments, the subject is suspect of having human rhino virus infection or having been exposed to human rhino virus.

In some embodiments, the sample has been treated to amplify RNA prior to contact with the riboregulator. In some embodiments, the sample has been treated to amplify RNA isothermally prior to contact with the riboregulator.

Another related aspect of this disclosure provides a method of treating a subject, comprising administering an effective amount of an anti-viral agent to a subject having a viral infection, wherein the subject is identified as having a viral infection or as having been exposed to a virus by detecting viral mRNA in a sample from the subject using one or more of the foregoing toehold riboregulators, including for example a toehold riboregulator comprising a nucleotide sequence of any one of SEQ ID NOs: 43841, 9602, 62866, and 19367.

Another related aspect of this disclosure provides a method of treating a subject, comprising administering an effective amount of an anti-cancer agent to a subject having a cancer, wherein the subject is identified as having a cancer by detecting increased mRNA expression of a human transcription factor in a sample from the subject using a toehold riboregulator, including for example a toehold riboregulator comprising a nucleotide sequence of any one of SEQ ID NOs: 164989, 111698, and 236638.

Another related aspect of this disclosure provides a system for assisted design of RNA-based synthetic biology components comprising at least one pre-processing stage dedicated to transform input nucleic acid sequences into a multi-dimensional representation, at least one machine learning architecture trained and optimized for classification and/or regression of said pre-processed sequences to predict at least one experimentally measured performance metric, and at least one output representing the attention and/or saliency mechanisms exhibited by at least one of the said machine learning architectures to inform further design of RNA-based synthetic biology components.

Another related aspect of this disclosure provides a method for assisted design of RNA-based synthetic biology components comprising generating pre-processed sequences comprising transforming input nucleic acid sequences into a multi-dimensional representation, training and optimizing at least one machine learning architecture for classification and/or regression of said pre-processed sequences to predict at least one experimentally measured performance metric, and generating at least one output representing the attention and/or saliency mechanisms exhibited by at least one of the said machine learning architectures to inform further design of RNA-based synthetic biology components.

These and other aspects and embodiments will be described in greater detail herein.

Figure 1:
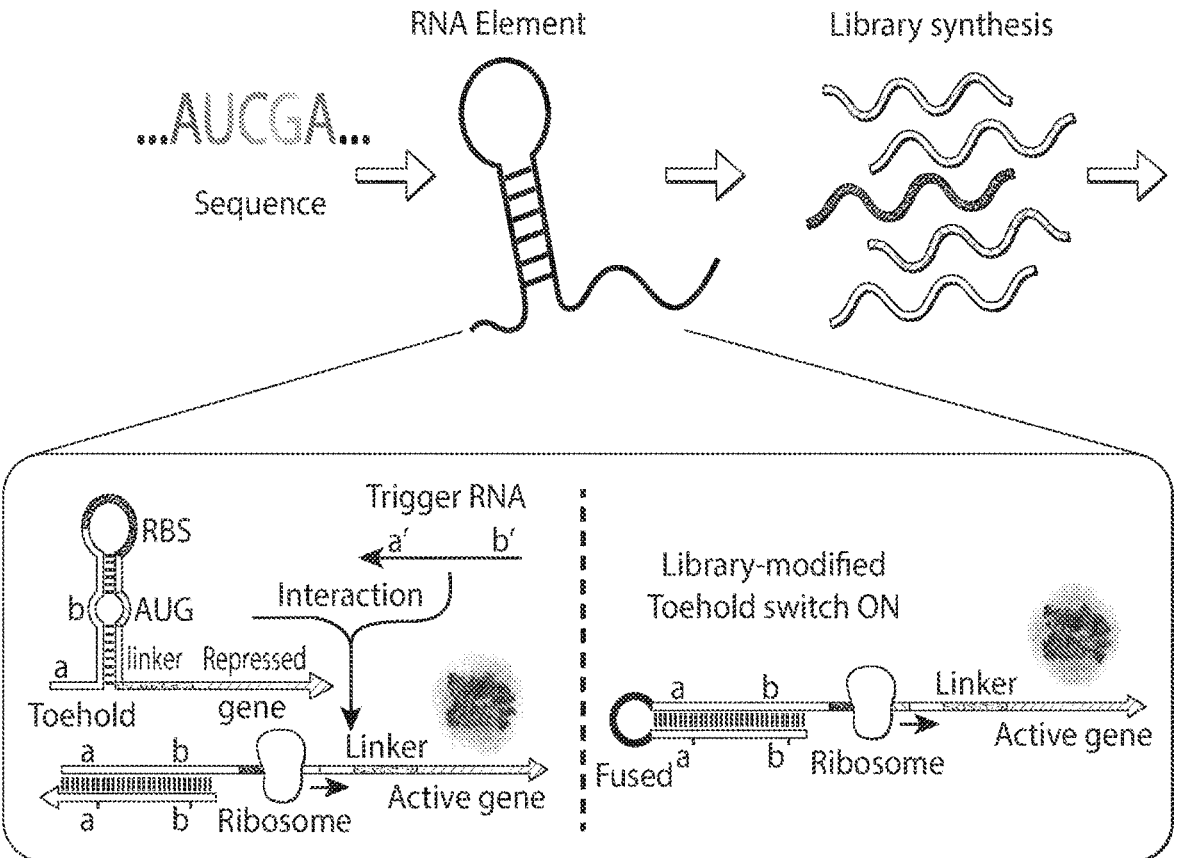
FIG. 1. Deep learning for RNA synthetic biology pipeline. RNA tool selection is followed by library synthesis and characterization with analysis using deep neural networks (DNN) to provide functionality predictions and design insight. We used a high-throughput toehold switch library as a canonical model for the general investigation of RNA synthetic biology tools. The original toehold switch architecture from Green et al. (2) was used, containing a 12-nucleotide (nt) toehold (a/a') and an 18-nt stem (b/b') fully unwound by the trigger (left-bottom). We selected to fuse the RNA trigger to the 5' end of the switch by an unstructured linker to facilitate library synthesis. Then, a flow-sequence (seq) pipeline was used to characterize the fluorescence signal of individual toehold switches in a pooled sequential assay, including pooled induction, FACS sorting, next-generation sequencing (NGS) and count frequency analysis. Finally, various DNN architectures were used to predict data outputs, while features contributing to DNN predictions were intuitively visualized to elucidate biological insights.
Figure 1:
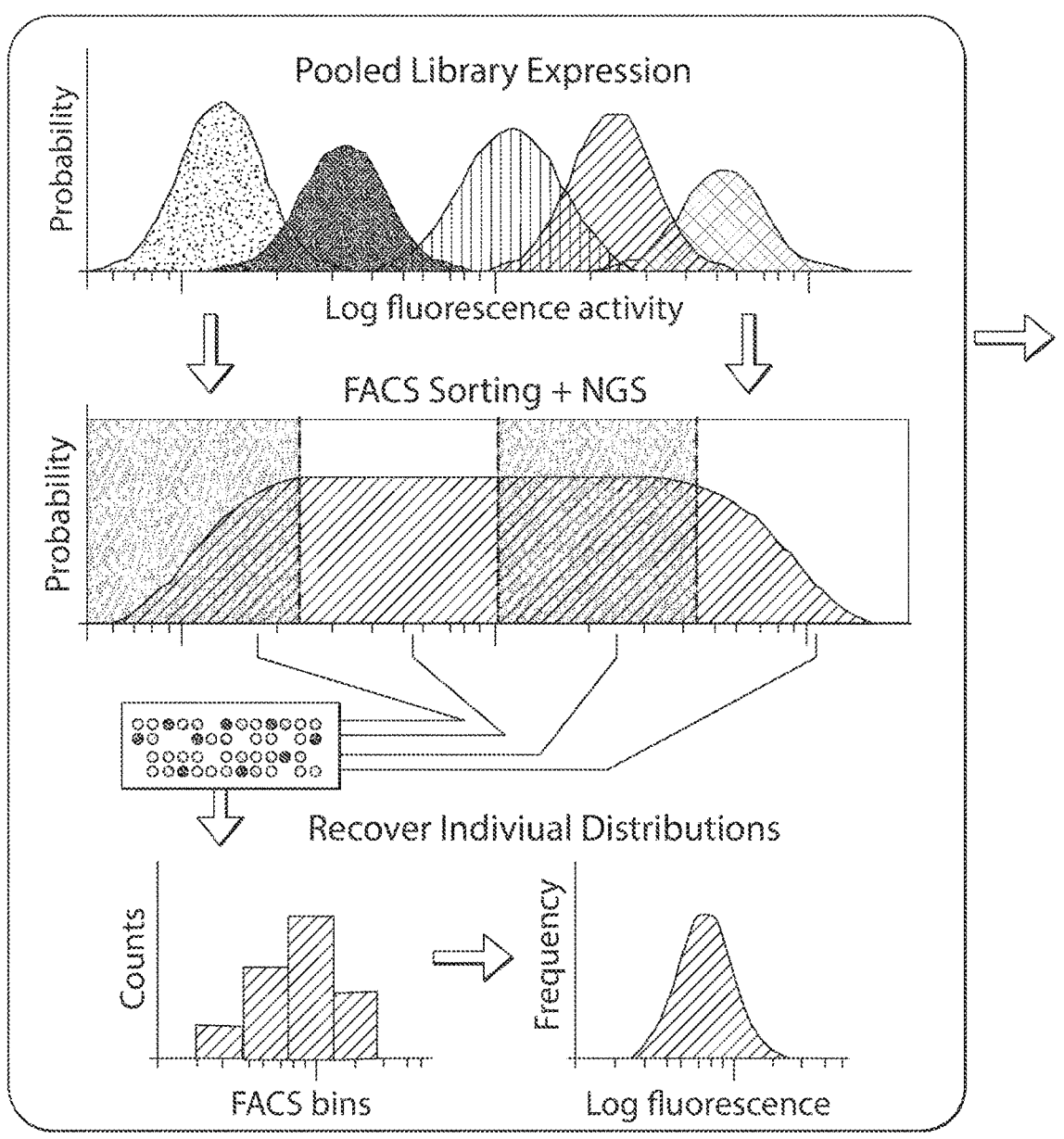
Figure 1:
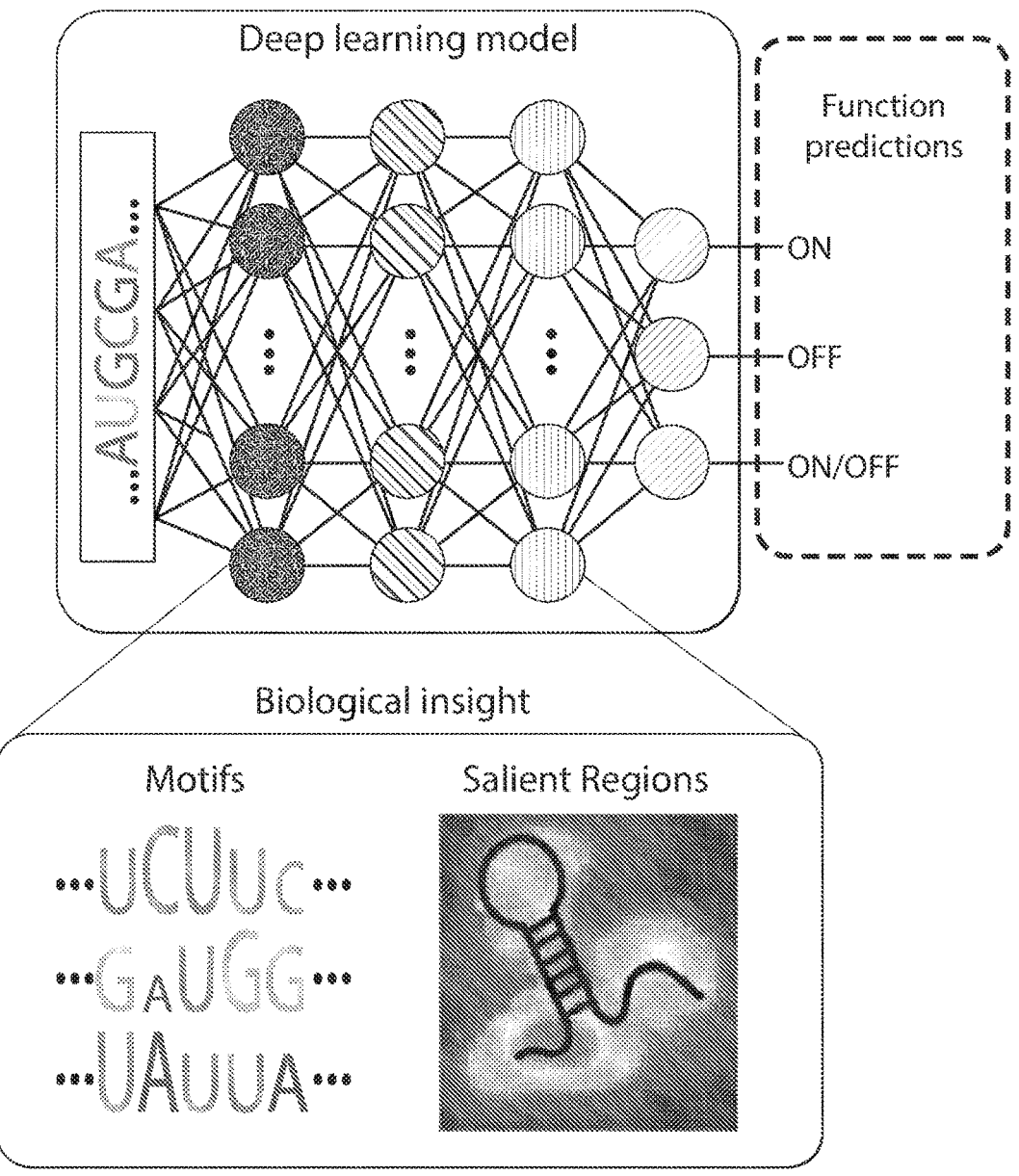

(E) Tested switch/trigger variants from each origin category, including randomly generated sequences, 906 human transcription factor transcripts, and 23 pathogenic viral genomes. (F) Experimental ON/OFF ratios for all triggers tiled across the transcripts of two clinically relevant human transcription factors (stat3 and kmt2a) upregulated in cancerous phenotypes (42, 43), as well as all triggers tiled across the genomes of two pathogenic viruses: West Nile Virus (WNV) and Human Immunodeficiency Virus (HIV). GFP=Green Fluorescent Protein; Seq=Sequence; HPV=Human Papillomavirus.

FIGS. 3A-G. Analysis of toehold switch performance using sequence k-mers, rational thermodynamic features, and sequence-based multilayer perceptron (MLP) models. (A) Sequence logos for k-mer motifs discovered to be disproportionately represented in weakly induced switches (low ON) and leaky switches (high OFF), functional proportions, and E-values. (B) The Pearson correlation (left, |max|=0.4) and $R^2$ metric (right, |max|=0.16) for thirty state-of-the-art thermodynamic features and obtained RBS Calculator v2.1 outputs. (C) Base architecture of investigated MLP models, featuring three fully connected layers. For training in regression-mode, three different outputs were predicted (ON, OFF, ON/OFF), whereas for classification training only a single binary output based on ON/OFF (threshold at 0.7) was predicted. (D) Box and whisker plots for $R^2$ between experimental and regression-based predictions for best performing rational features, logistic regression models and MLPs. (E) Minimum absolute error (MAE) between experimental and predicted values for these same models. (F) Box and whisker plots for area under the curve (AUC) of the receiver-operator curve (ROC) and the precision-recall curve (P-R) in classification-mode predictions compared to experimental values. In both regression and classification, the one-hot encoded sequence MLP delivered top-in-class performance without using pre-computed thermodynamic or kinetic metrics. (G) ROC curves of pre-trained MLP classification models validated with an unseen 168-sequence external dataset from Green et al. (2).

FIGS. 4A-D. Evaluation of neural network architectures with increased capacity. Performance metrics for convolutional neural networks (CNN) and long short-term memory (LSTM) networks trained on one-hot encoded toehold sequences, as well as a CNN trained on a two-dimensional, one-hot encoded sequence complementarity map. All models are compared to the previously reported MLPs trained on the 30 pre-calculated thermodynamic features and one-hot toehold sequences. For regression-based predictions (A) shows box and whisker plots for $R^2$ metric, while (B) shows MAE for all models. In the case of classification-based predictions (C) shows box and whisker plots of the area under the curve (AUC) of the receiver-operator curve (ROC) and the precision-recall curve (P-R) for all tested models. In both regression and classification, the one-hot encoded sequence MLP delivered top-in-class performance as compared to higher capacity deep learning models. (D) ROC curves of pre-trained higher-capacity classification models validated with an unseen 168-sequence external dataset from Green et al. (2). In A-C, for each group of 5 boxes, the first box represents MLP—All Rational Feat., the second box represents MLP—OneHot Seq., the third box represents CNN—OneHot Seq., the fourth box represents LSTM—OneHot Seq., and the fifth box represents CNN—2D Comp. Map.

FIGS. 5A-F. VIS4Map: Visualizing secondary structure features using saliency maps of a sequence-based complementarity matrix input. (A) A simplified schematic of the CNN-based architecture used to generate toehold functional predictions with network attention visualizations. The system receives a one-hot encoded, two-dimensional (2D) sequence complementarity map as input, followed by three 2D convolutional/max-pooling layers, a flattening step, and finally a set of dense layers. After output generation (e.g., OFF), a gradient-weighted activation mapping is performed to visualize activation maximization regions responsible for delivered predictions (VIS4Map). (B) Histograms of the percentage overlap between VIS4Maps generated from a CNN pre-trained to predict minimum free energy (MFE) using 120-nt RNA sequences and MFE maps generated by NUPACK. When analyzed using 500 random test set sequences, the distributions of correctly matched and randomly assigned maps are distinct with increased percentage overlap from matched samples as compared to unmatched. (C) Examples of saliency VIS4Maps compared with their corresponding MFE structures as predicted by NUPACK for three randomly selected 60-nt RNA sequences. See FIG. 16A for additional examples with 120-nt RNA sequences. (D) Four representative VIS4Map examples of randomly selected 118-nt RNA toehold switch sequences from an OFF-predictive CNN model. (E) Averaged VIS4Maps of 10,125 randomly selected toehold switch RNA sequences from our library test-set processed with our OFF-predicting CNN model (left) and compared their corresponding averaged MFE maps obtained using NUPACK (right). (F) Averaged VIS4Maps of the 10% most accurately predicted switches sorted by quartile from lowest OFF (tight) to highest OFF (leaky), inset at the hairpin stem, and toehold region of the switch. After contrast enhancement of averaged VIS4Maps to visualize sparsely distributed secondary structures, a noticeable increase in structures outside of the prominent equilibrium-designed switch hairpin structure appears, corresponding to increased toehold leakiness. A toehold switch schematic (right) is shown to denote how incorrectly folded and potentially weaker kinetically stable intermediate structures might compete with the correctly folded structure that is designed to be reached at equilibrium.

Figure 6A:
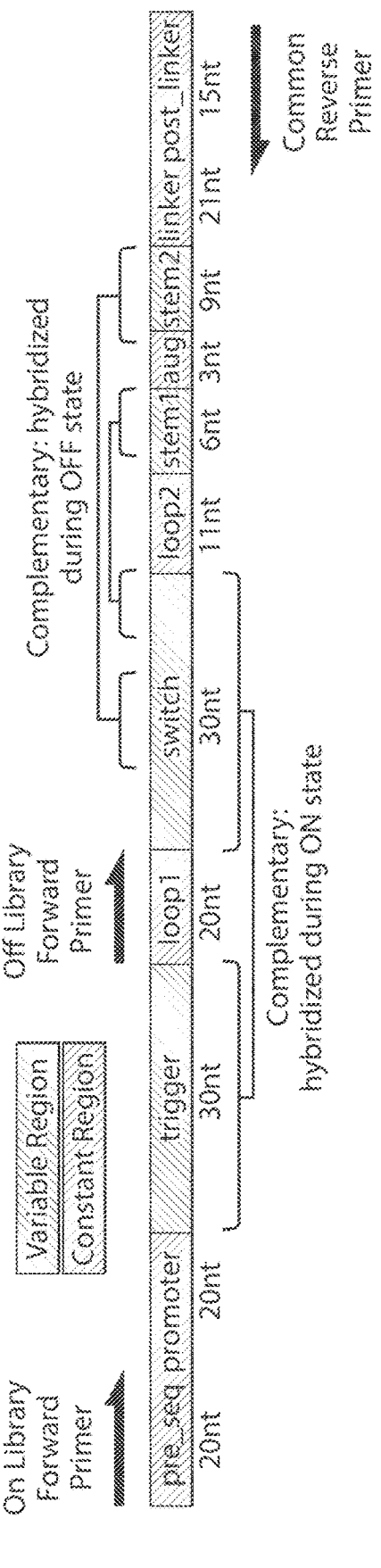
Figure 6B:
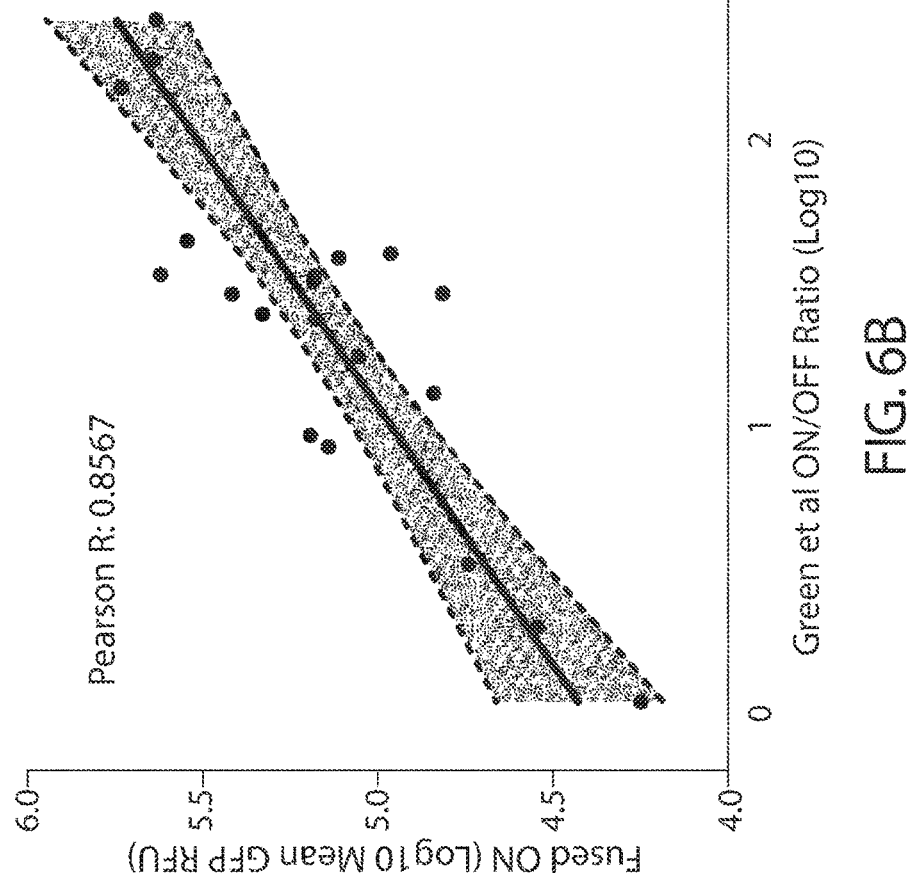

FIGS. 6A-B. Design and validation of oligomer library. Individual toehold switch constructs within the library were synthesized from a pool of oligomers, and a representative panel of constructs was verified against a previously published dataset. (A) Schematic of the pooled library oligo used for the synthesis of our high-throughput toehold switch library. Distinct toehold construct regions include: pre_seq (plasmid backbone sequence) (e.g., SEQ ID NO: 244020), promoter (T7 promoter including GGG) (e.g., SEQ ID NO: 244021), trigger (toehold-unique), switch (complete toehold and ascending stem), loop1 (region linking trigger to switch) (e.g., SEQ ID NO: 244022), loop2 (main toehold switch hairpin loop containing the RBS) (e.g., SEQ ID NO: 244023), stem1 (top half of descending stem), atg (start codon), stem2 (bottom half of descending stem), linker (21 nt sequence of unstructured amino acids) (e.g., SEQ ID NO: 244024) and post_linker (first 15 nt of GFP) (e.g., SEQ ID NO: 244025). Further detail can be found in Table 4. Amplification primers for both ON and OFF libraries (including the common reverse primer) are shown with black arrows. Sequences of common reverse primer, on forward primer and off forward primer are provided as SEQ ID NOs: 244026-244028. (B) Comparison of ON state GFP expression from a panel of 20 individually assayed switches from our high-throughput toehold switch pipeline against the ON/OFF ratio for equivalent switches reported by Green et al. (1). The agreement between the 5' fused triggers used in this work and the separately transcribed triggers used by Green et al. (1) was assessed based on the Pearson correlation coefficient (0.8567). GFP=Green fluorescent protein, nt=nucleotide, RBS=Ribosome binding site.

Figure 7:
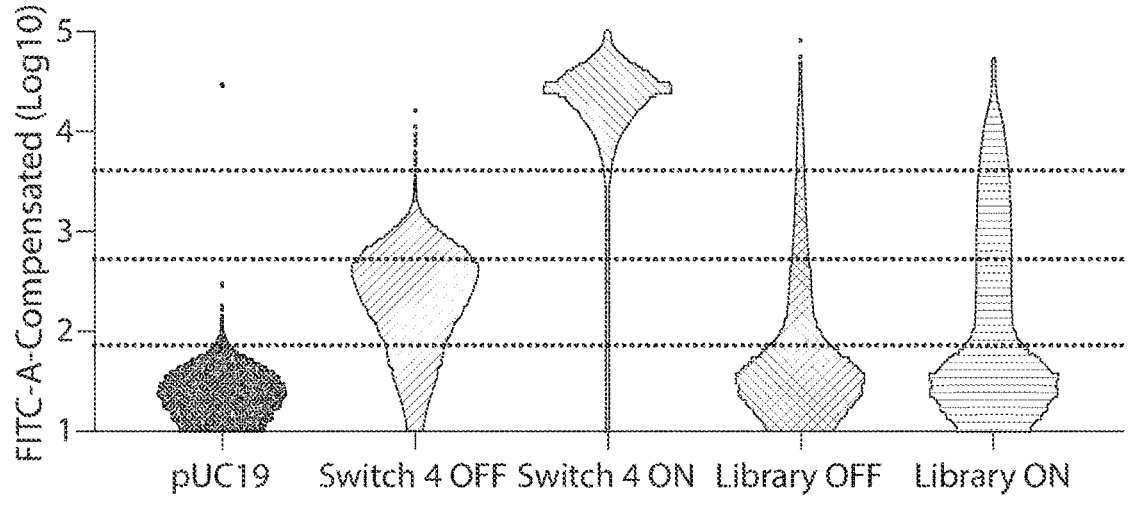

FIG. 7. Library FACS distributions and empirically-derived sorting gates. To determine the boundaries of the sorting gates for our high-throughput toehold switch pipeline, we used Switch #4 from Green et al. (1) in ON and OFF conformations as positive controls, and a pUC19 plasmid lacking a GFP gene as a negative control. Fluorescence distribution plots of IPTG-induced *E. coli* BL21-star cells from the three control conditions are shown alongside complete ON and OFF libraries for comparison. Boundaries for the four sorting bins are shown as dotted lines.

Figure 8A:
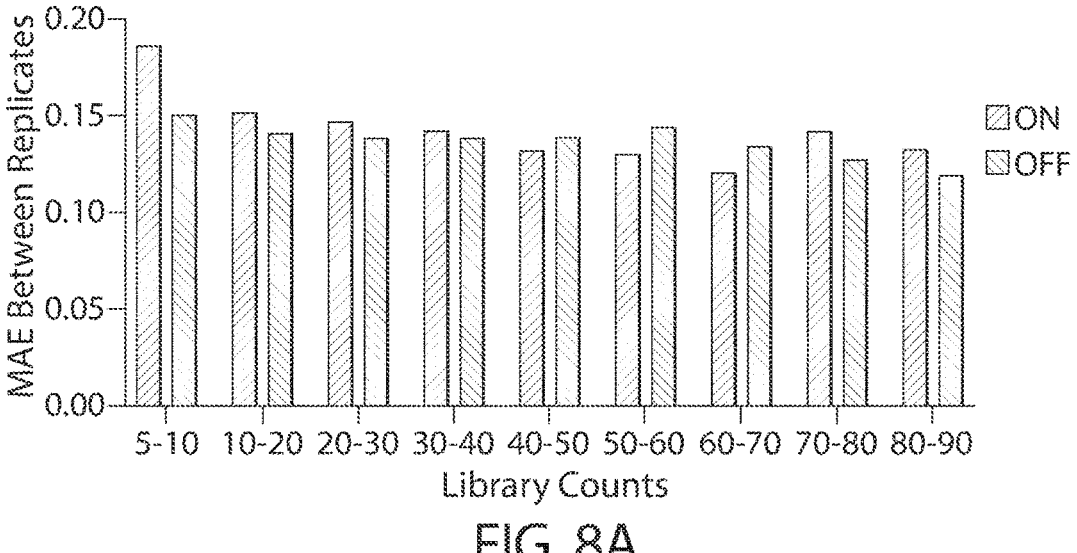
Figure 8B:
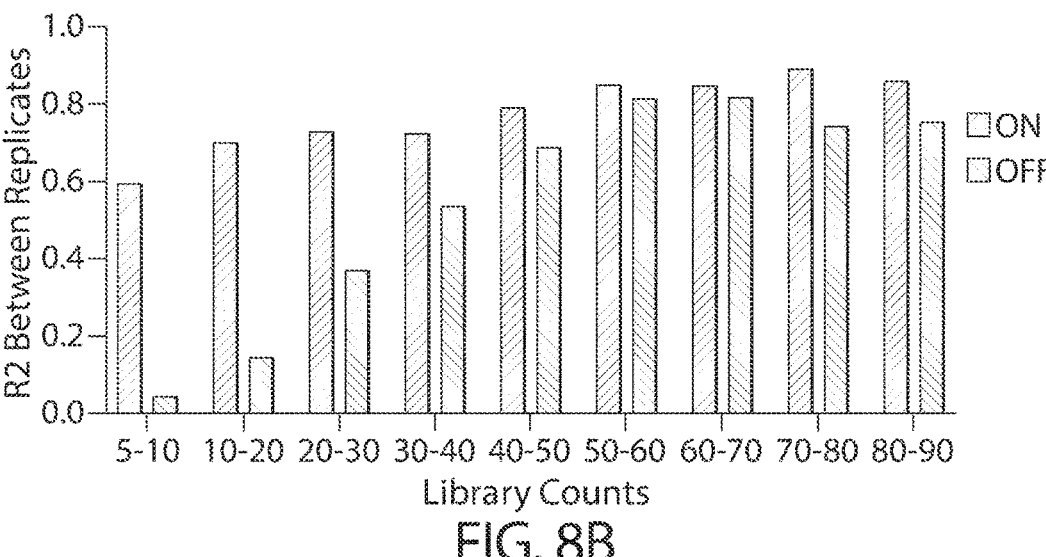

FIGS. 8A-B. Inter-replicate variability of toehold switch libraries. For the same initial toehold library, we performed two replicates of the BL21 transformation process followed by independent induction, sorting, and sequencing. Two metrics were used to compare the inter-replicate variability: (A) the mean absolute error (MAE), and (B) the $R^2$ correlation coefficient. Shown are the MAE and $R^2$ values for ON (first bar in each pair) and OFF (second bar in each pair) measurements at different ranges of library count thresholds.

Figure 9:
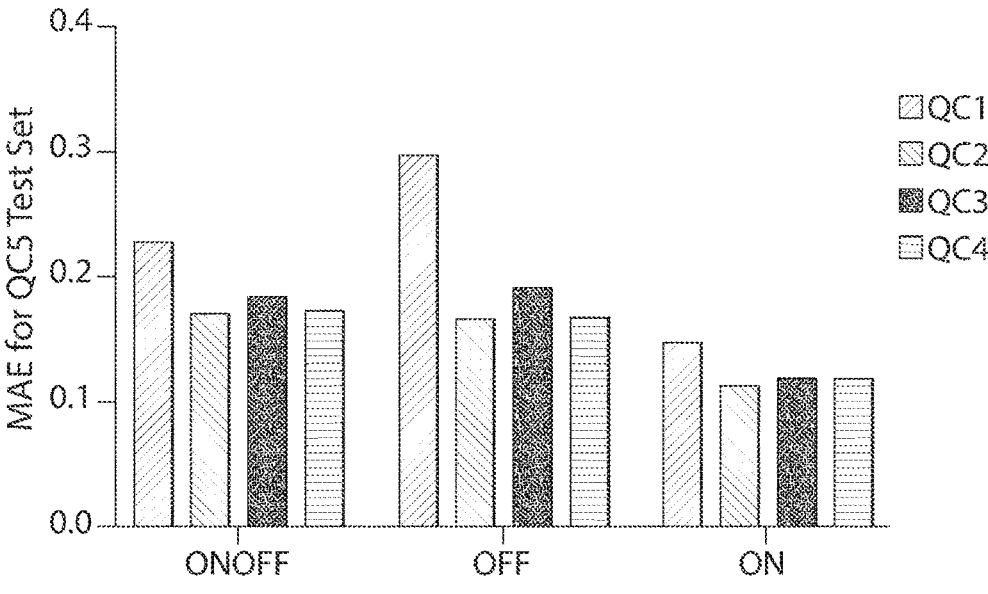
Figure 9:
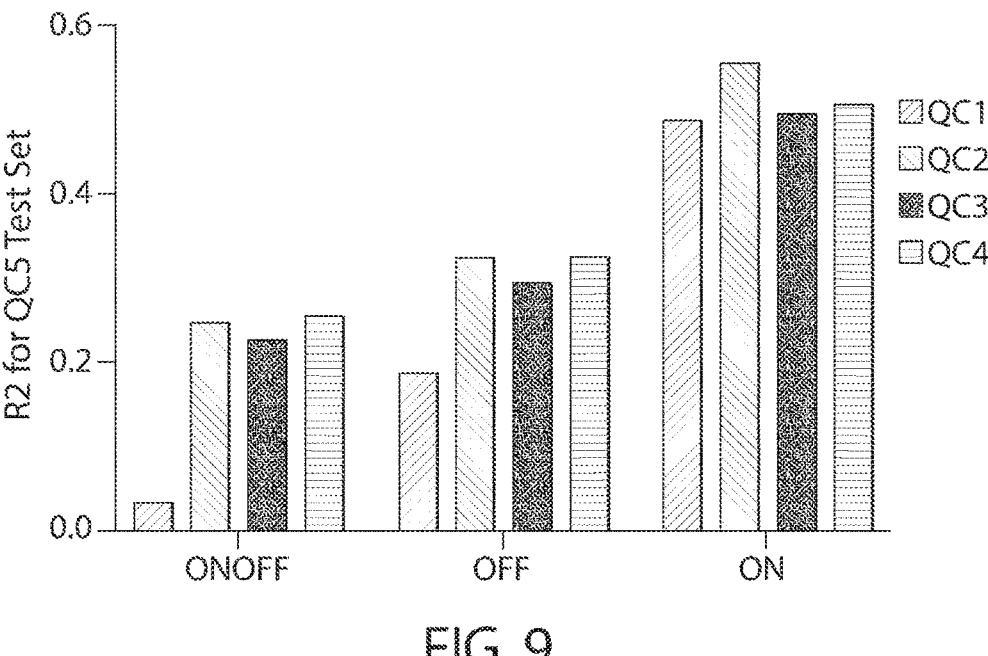

FIG. 9. Effect of QC level on MLP performance. The predictive power of our multilayer perceptron model was evaluated after training with datasets obtained from increasingly stringent quality control (QC) thresholds. The most stringent quality control group (QC5) was withheld as a test set, and an MLP trained on a one-hot representation of the toehold sequence was given either QC1 (first bar in each 4 bar group), QC2 (second bar in each 4 bar group), QC3 (third bar in each 4 bar group), or QC4 (fourth bar in each 4 bar group) as training data. From the resulting test-prediction of QC5 values, we show the MAE (upper panel), and the analogous $R^2$ correlation metric (lower panel) between the predicted and experimental values. See Table S1 for conditions for each QC level.

Figure 10:
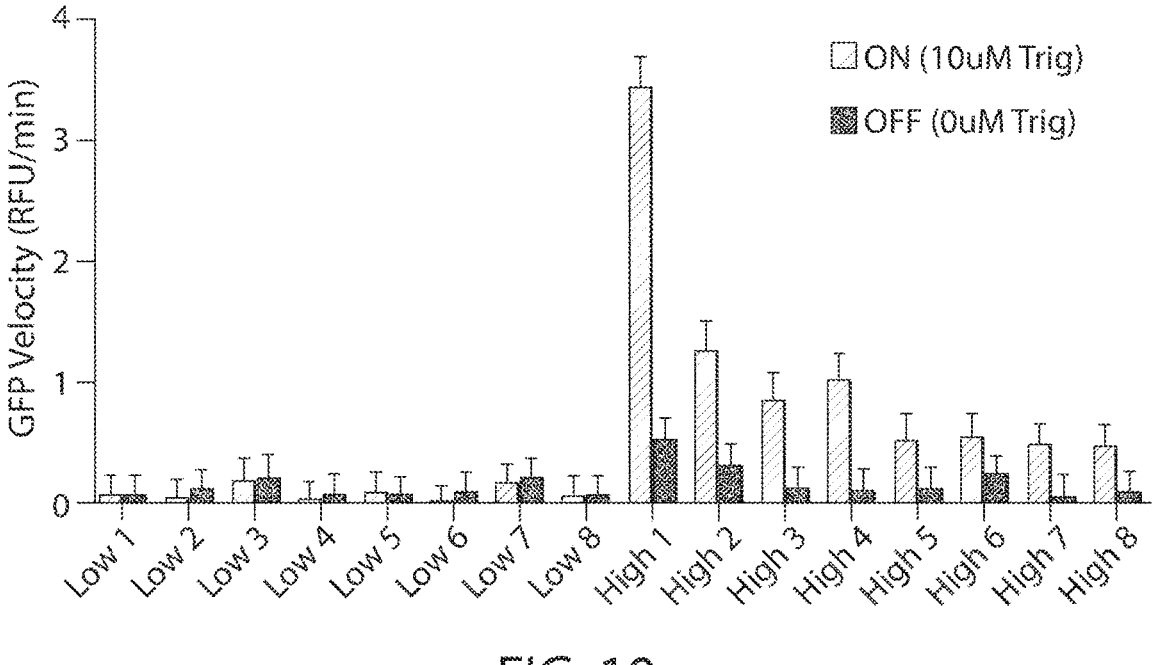

FIG. 10. Cell-free toehold switch validation. A panel of toeholds that showed either a low or high ON/OFF ratio as measured by our high-throughput flow-seq assay were individually cloned and assayed in a cell-free protein synthesis (CFPS) system. The time course velocities of GFP signal evolution are shown for the PURExpress CFPS reactions containing the sixteen switches with or without their separately transcribed RNA triggers. The sequences and flow-seq assay results for these sixteen switches can be found in Table 2. ON measurement is the first bar of each pair and corresponds to 10 μM trigger. OFF measurement is the second bar of each pair and corresponds to 0 μM trigger.

Figure 11A:
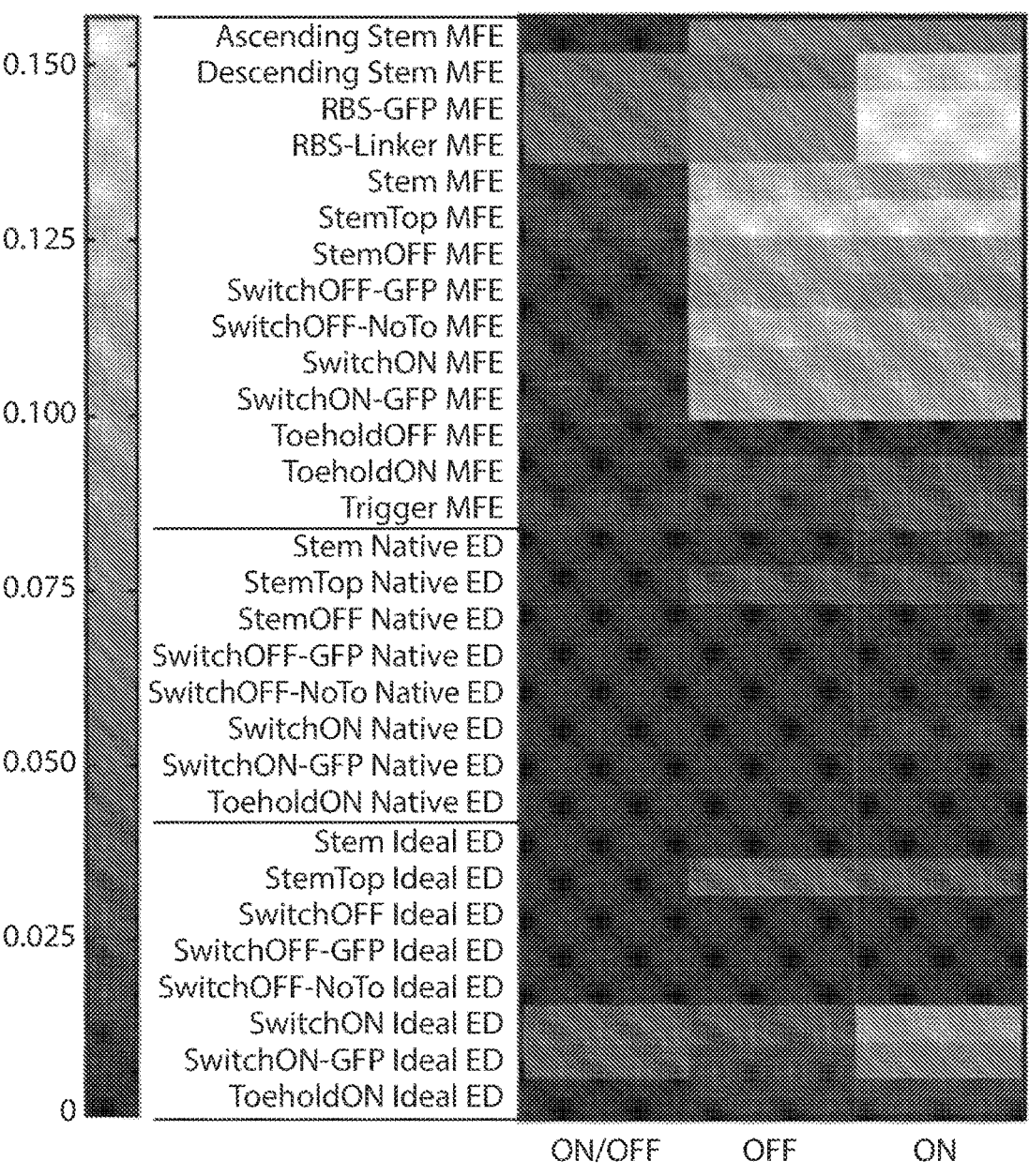
Figure 11B:
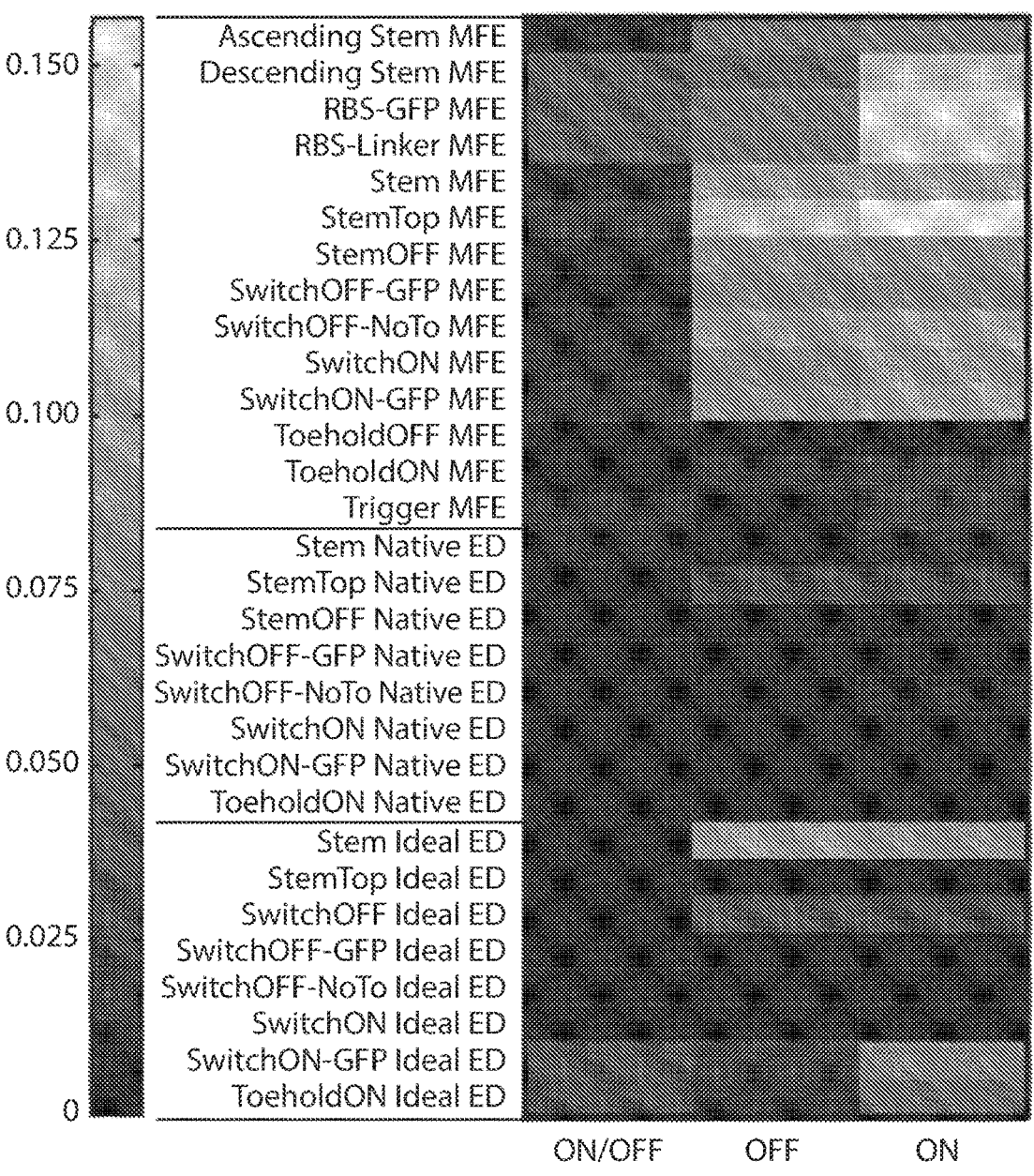

FIGS. 11A-B. Correlation between rational thermodynamic features and toehold switch dataset, subsetted for A-U content. We analyzed the $R^2$ coefficients between 30 commonly used thermodynamic features and the ON, OFF, or ON/OFF measurements of variants in our high-throughput dataset. (A) $R^2$ coefficients for the subset of switches that contained only an A-U or U-A base pair at the top of the toehold switch stem (positions 79 and 91 in Table 4). (B) $R^2$ coefficients for the entire set of switches, allowing for any base pair at the top of the toehold switch stem. Both $R^2$ value sets were compared to evaluate findings from Green et al. (1) where subsetting for switches with an A-U or U-A basepair at the top of the stem was sufficient to dramatically increase the predictive $R^2$ coefficient between thermodynamic features and measured ON/OFF. We found measurable differences between various thermodynamic features when subsetting for an A-U basepair at the top of the hairpin stem, particularly for those in the Ideal Ensemble Defect (ED)

block. However, differences between the $R^2$ values in said subset and those obtained for other possible base-pairs were not statistically significant suggesting no overall increase in predictive value (p>0.05 for ON, OFF, and ON/OFF, two-tailed t-test).

FIGS. 12A-F. Kinetic toehold switch folding analysis using Kinfold. Folding trajectories were run using the Kinfold package for the OFF-state switch sequence (positions 50-134 nt in Table 4). (A) For a single representative toehold switch, six example trajectories are shown. Trajectories in green reached the MFE structure within $10^3$ arbitrary time units (au), while those in blue did not. (B) For two representative toehold switches, 100 trajectories were run for a maximum time of $10^6$ au. Histograms of the time required for a trajectory to reach the MFE structure are shown. Most trajectories took longer than $10^3$ au, compared to the Kinfold analyses in Borujeni et al. (6), where average trajectory times fell in the range of $10^1$-$10^3$ au, and $10^4$ au was the longest allowed trajectory time. (C,D,E,F) For each switch in the QC4 dataset (total 19,983 variants), 100 trajectories were run and the following measurements plotted: (C) histograms of the mean and negative standard deviation of the trajectories' average energy during the first $10^3$ au, (D) the fraction of trajectories that completed folding of the MFE structure before $10^3$ au, (E) the ratio of average trajectory energy to the minimum possible MFE energy, and (F) the $R^2$ correlation between the metrics in C,D,E and the empirical measurements in our toehold switch dataset. For comparison with previous rational features the heatmap axis is set identically to FIG. 3B.

Figure 13A:
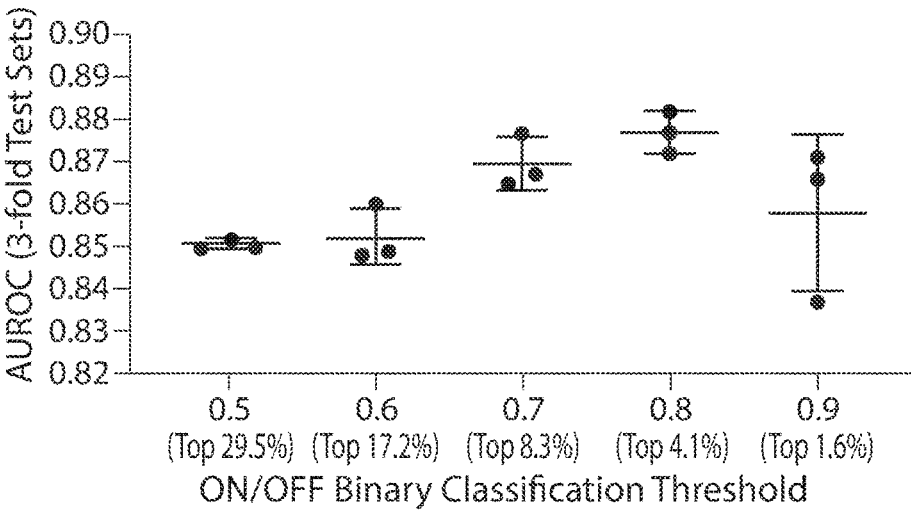
Figure 13B:
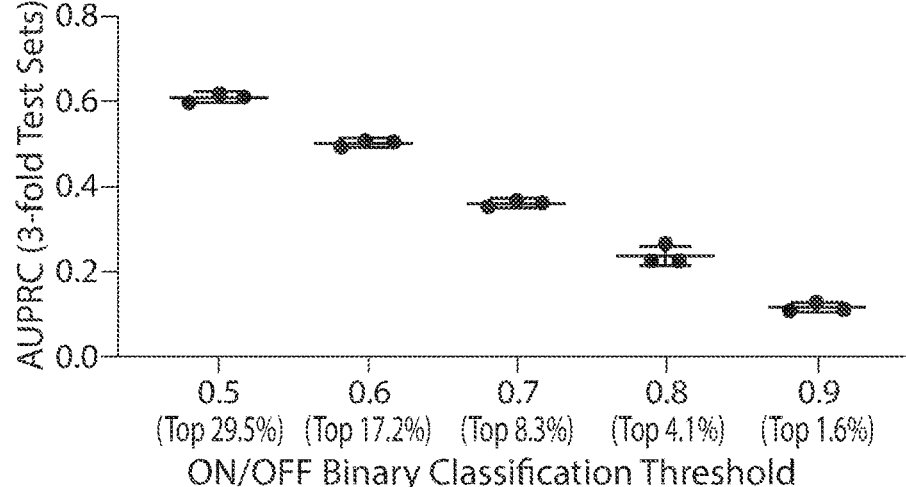
Figure 13C:
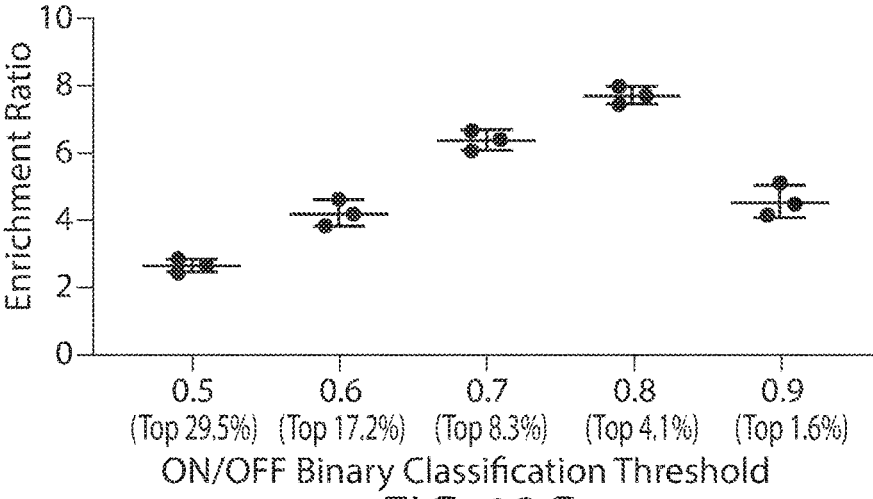

FIGS. 13A-C. Determination of the optimal ON/OFF binary classification cutoff threshold. AUC, P-R, and enrichment ratio analyses were used to determine the optimal cutoff threshold at which to binarize ON/OFF data for classification. We trained a standard MLP architecture on the one-hot sequence representation of the toehold switch at five different binarization thresholds, and compared the following performance metrics: (A) model AUROC results, (B) model AUPRC results, and (C) model enrichment ratio over random chance. The enrichment ratio is calculated as the fraction of true positive toehold switches returned by the model (i.e., the precision) divided by the fraction returned by random chance. The enrichment ratio was specifically calculated at the level of precision for which the recall returns one positive switch per 100, or approximately ten on average for a typical mRNA of length ~1000 nt. The final threshold selected for all classification models in this study was 0.7 (or the top 8.3% of switches), balancing a high enrichment ratio with a practical degree of overall precision.

Figure 14:
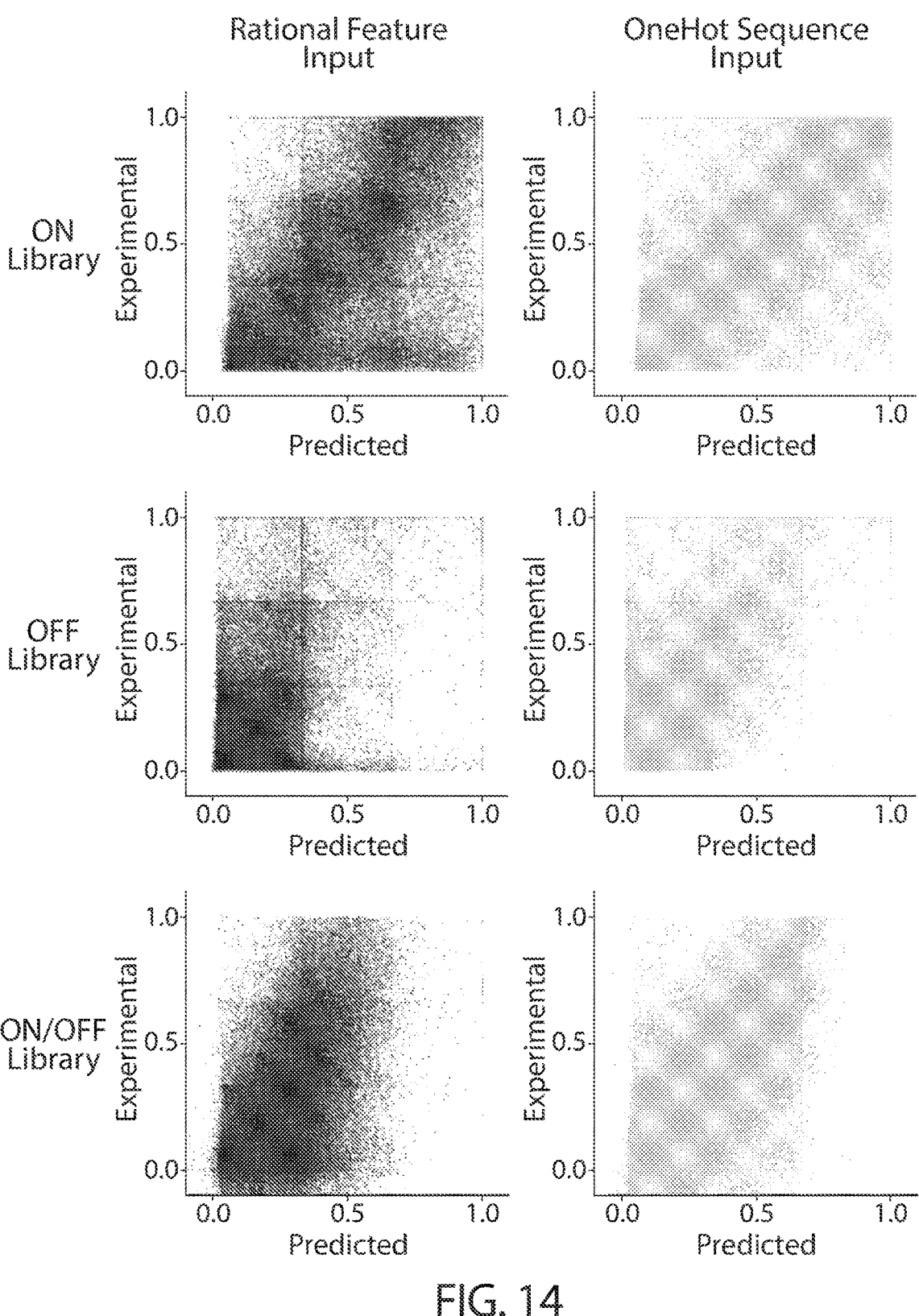
Figure 15A:
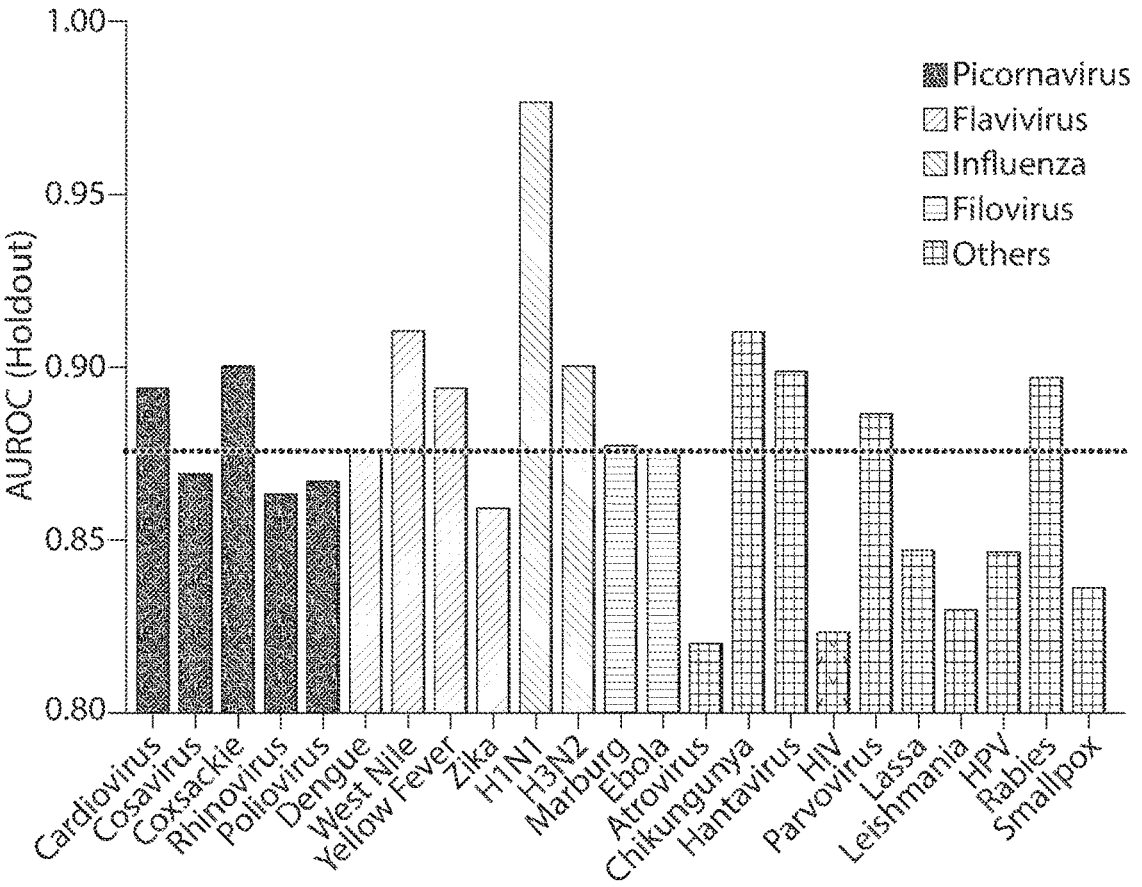
Figure 15B:
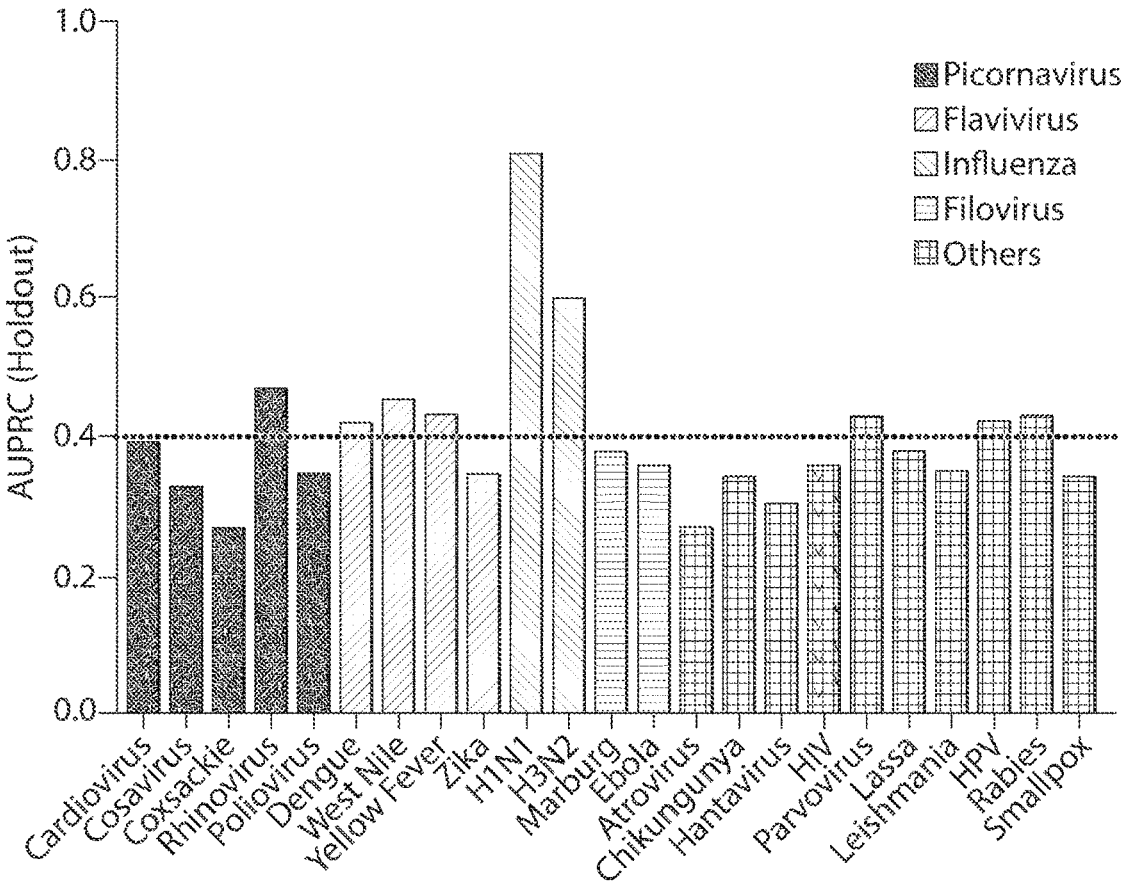
Figure 15C:
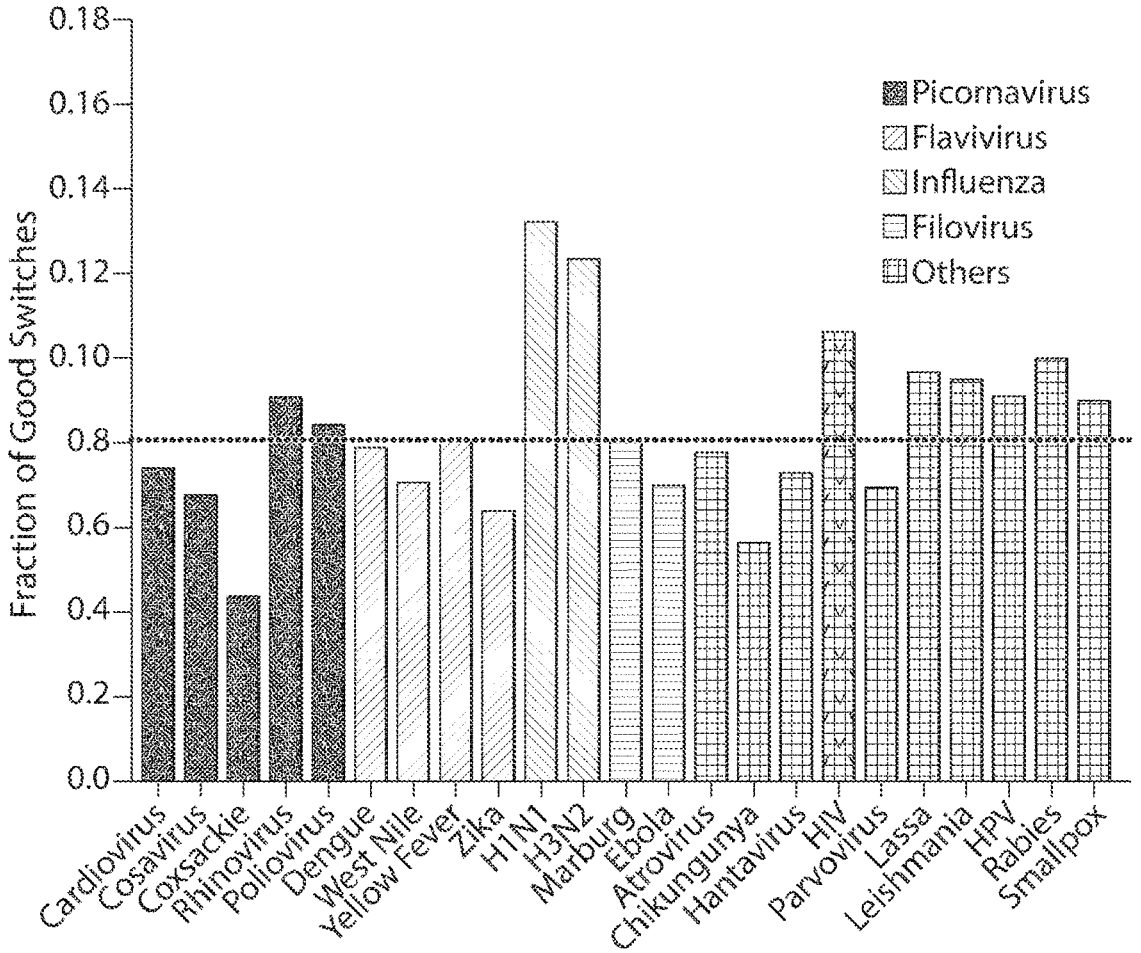
Figure 15D:
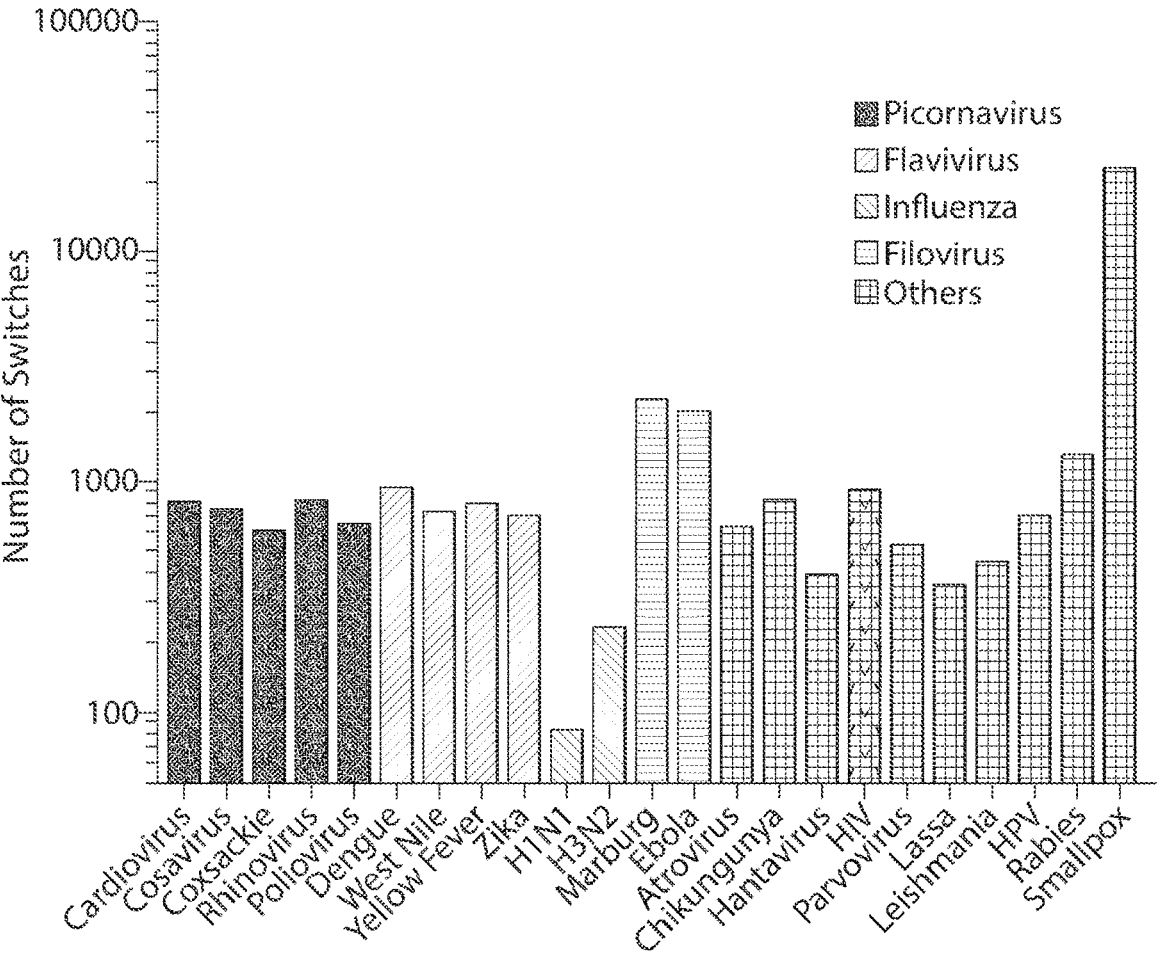

FIG. 14. MLP predictions vs. experimental results. Scatter plots of the predicted versus empirical values of our compiled test set are shown for ten-fold cross-validated MLP models trained with either the 30 pre-calculated rational thermodynamic features as inputs (left, dark green), or the toehold switch one-hot sequence representation as input (right, light green) for ON, OFF, and ON/OFF. Summary statistics are reported in FIG. 3D,E.

FIGS. 15A-D. Holdout validation of individual viral genomes. For each of the 23 pathogenic viruses tiled in our toehold switch dataset, every toehold switch targeting a given viral genome was withheld, and an MLP model was trained with the remaining sequences in the dataset using a one-hot sequence input representation classifying for ON/OFF ratio. The model performance was then evaluated on the switches of the withheld viral genoma as a test set. (A) Area under the receiver operating characteristic curves (AUROC) for holdout viral genomes. Dotted line denotes AUROC average across test samples. (B) Area under the precision-recall curves (AUPRC) for holdout viral genomes. Dotted line denotes AUPRC average across test samples. (C) Fraction of toehold switches in synthesized high-throughput library classified as high-performing for each virus type. Dotted line denotes average at 8%. (D) Total number of toehold switches synthesized for each virus type.

Figures 16A, 16B:
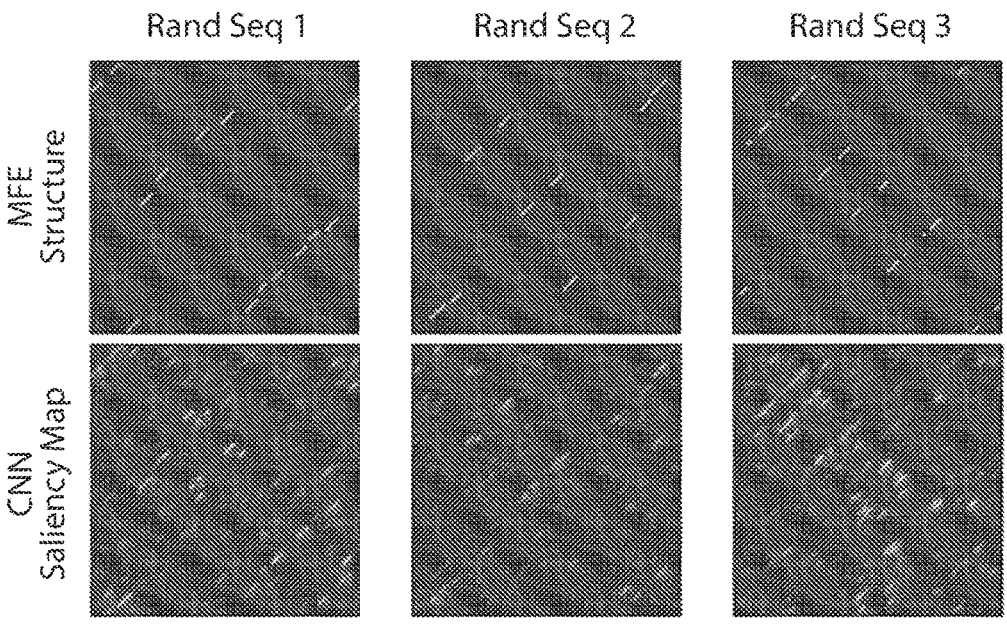

FIGS. 16A-B. VIS4Map analysis of random toehold sequences in MFE predictor 2D CNN model. A dataset of 50,000 random RNA sequences of length 120 nt and their corresponding MFE values were generated using NUPACK. A convolutional neural network (CNN) was then trained to predict the MFE of each sequence using either a one-hot representation or a complementarity map representation of the sequence as input. (A) For three randomly selected RNA sequences, representative saliency maps generated from the CNN model are shown alongside the MFE structure pre-computed independently using NUPACK. The CNN model was trained on complementarity map inputs. Overlap between salient diagonal features in the VIS4Map outputs and MFE structure maps is visible. (B) We then compared the $R^2$ coefficients between NUPACK-calculated MFE values and the predictions of a CNN model trained either on a one-hot representation or a complementarity matrix representation of the random RNA sequences. Error bars show standard deviation from five shuffled test sets.

Figure 17:
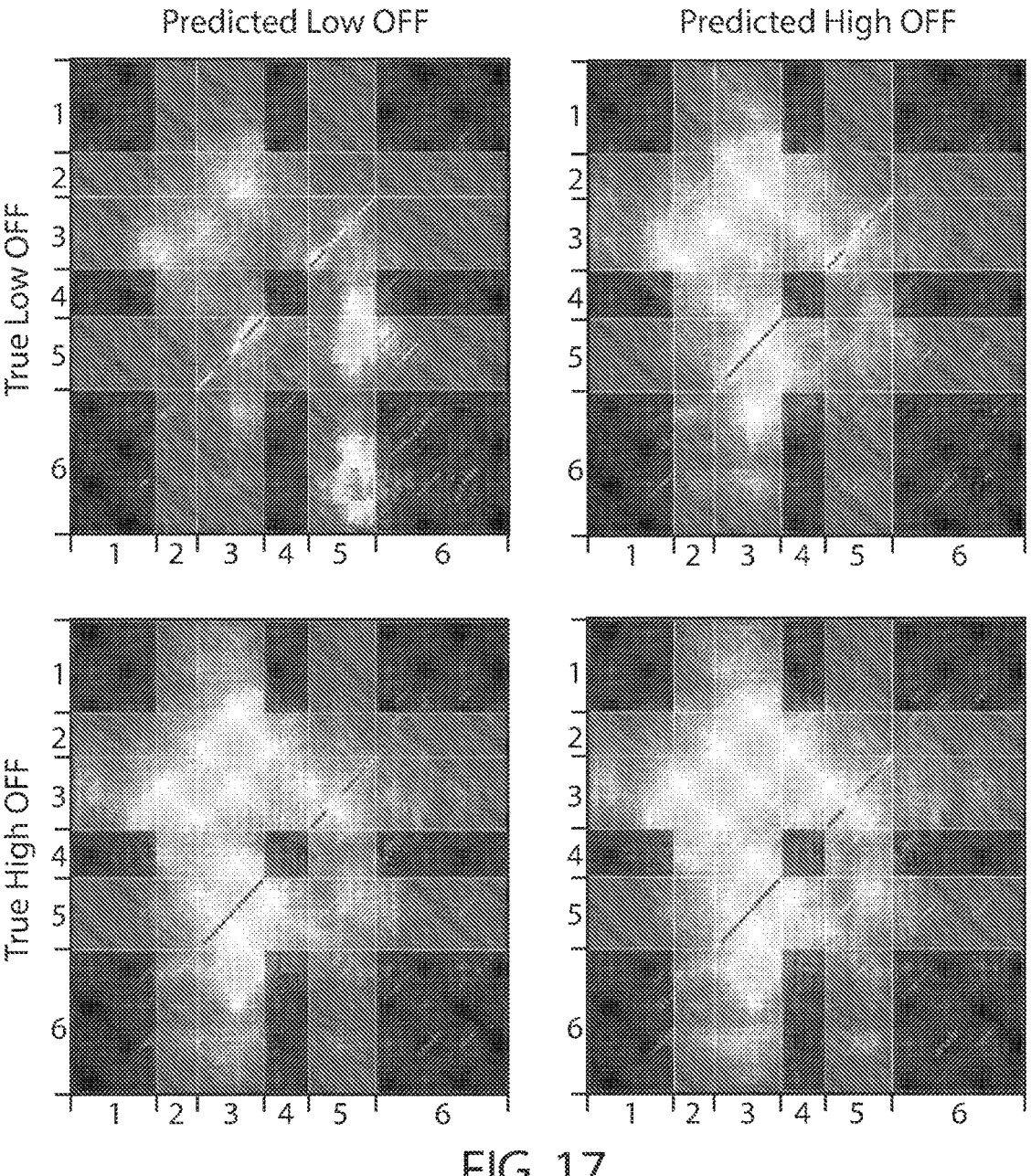

FIG. 17. VIS4Map confusion matrix analysis of switch OFF conformation. Saliency maps generated from a CNN model trained to predict the toehold switch OFF metric are shown for different ground-truth OFF metrics. The model was trained using a complementarity matrix representation of the toehold sequence as input. Regions labeled on the axes are as follows: 1) Constant Loop, 2) Toehold, 3) Ascending Stem, 4) Constant RBS Loop, 5) Descending Stem, and 6) Constant Linker. Regions of interaction between constant regions are shaded darker as they do not contain variability between different switch sequences. All saliency maps were generated from the test set only. Saliency maps were then sorted according to the 25% highest and 25% lowest experimentally-determined OFF signal. The 10% best-predicted and 10% worst-predicted saliency maps from the high OFF and low OFF groups were then averaged to produce the shown confusion matrix. Contrast was enhanced four-fold in the averaged maps in order to visualize more sparsely distributed features.

Figure 18:
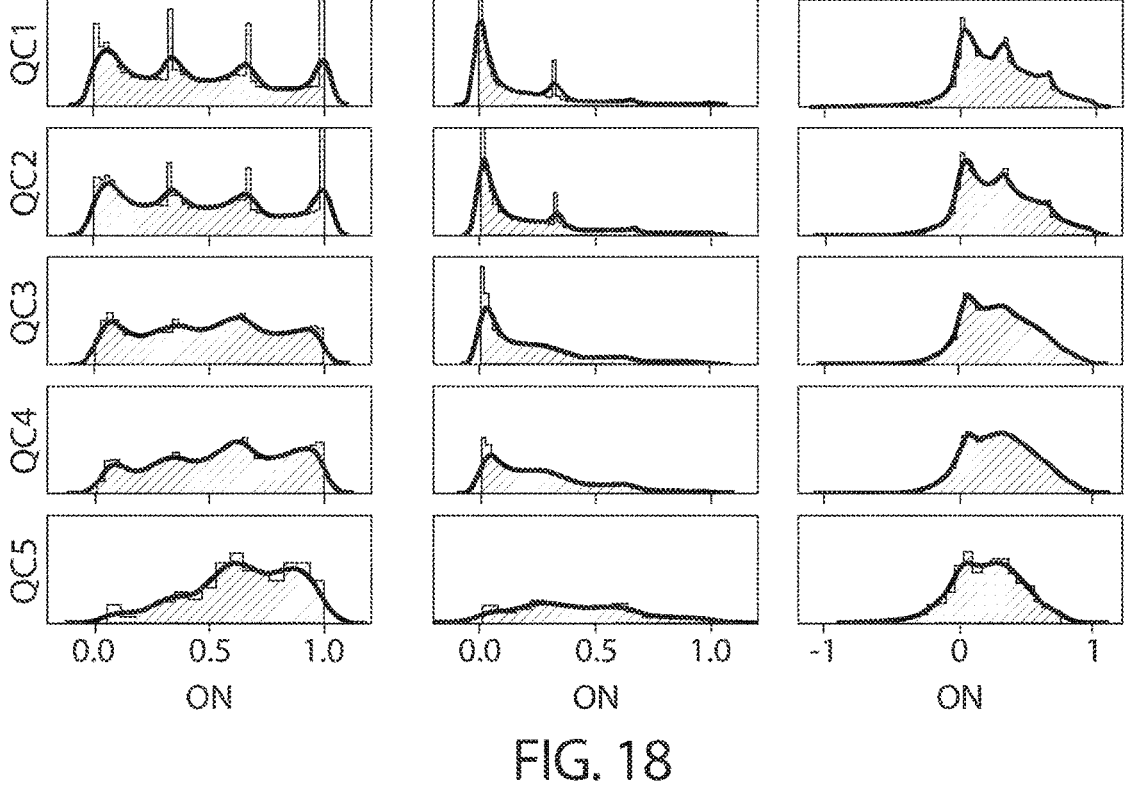

FIG. 18. Dataset distribution vs. QC level. Histograms of toehold switch library values for ON, OFF, and ON/OFF were grouped according to our five different QC threshold levels and are shown here for comparison. The y-axis limits are held constant for ON, OFF, and ON/OFF, respectively, across QC levels after normalizing for data subset size.

Color version of these Figures are accessible on the United States Patent and Trademark Office PAIR website, under the Supplemental Tab of the file history for U.S. Provisional Application Ser. No. 62/948,175, filed Dec. 13, 2019.

DETAILED DESCRIPTION OF INVENTION

This disclosure provides numerous toehold riboregulators, each specific for a particular human transcription factor or a particular virus. Some of these riboregulators may be used to detect the presence of a particular virus, and this may aid in the diagnosis of an infection by such virus. Some of these riboregulators may be used to detect the presence or expression level of a particular human transcription factor, and this may aid in the diagnosis or prognosis of a condition associated with the presence and/or increased expression of such transcription factor. One such condition is cancer. For example, the human transcription factor STAT3 is reportedly upregulated in certain cancers, and it may therefore act as a diagnostic and/or prognostic marker of such cancers.

As will be described in greater detail herein, the toehold riboregulators may be provided covalently conjugated, typically at their 3' ends, to a coding domain. The coding domain may be a reporter domain. The reporter domain may encode a reporter protein. Alternatively, the reporter domain may encode a reporter RNA (e.g., an RNA aptamer). Such toehold riboregulator-reporter domain constructs may be used to detect and/or measure a level (e.g., an expression level) of a nucleic acid of interest (i.e., a trigger nucleic acid that is present in the sample being tested).

Riboregulators are nucleic acid molecules that exist in two different conformations (i.e., closed and open conformations). In the closed conformation, the riboregulator adopts a secondary hairpin structure that sequesters a ribosome binding site (RBS) in a loop domain, rendering the RBS inaccessible to translation machinery. In the open conformation, the riboregulator adopts a linear structure and the RBS is no longer sequestered and rather it is accessible to the translation machinery. Riboregulators are designed to convert from their closed to their open conformations in the presence of a target nucleic acid (referred to herein as a trigger nucleic acid), which is typically the nucleic acid of interest in a sample. Thus, the conversion from closed to open conformations occurs upon specific binding of the riboregulator to a trigger nucleic acid. The binding of to the trigger causes the conversion which then enables expression of a downstream coding domain, such as a reporter protein domain. Presence of the reporter protein is therefore a surrogate for the presence of the trigger nucleic acid.

The riboregulators share a common structure, as shown in FIG. 1, which includes, in a 5' to 3' order, a single-stranded toehold domain, a hairpin domain comprising a stem domain and a loop domain, and a linker domain. The loop domain comprises the ribosome binding site (RBS, e.g., AGAG-GAGA) and the stem domain comprises the start codon, AUG, on the descending strand. The stem domain further comprises first and second stem domains, called stem domain 1 and stem domain 2. The start codon, AUG, separates stem domain 1 from stem domain 2, on the descending strand, as illustrated in FIG. 1. The single-stranded toehold domain and the adjacent ascending sequence of the stem domain together are referred to as the "switch" domain. This domain is represented by a+b (5' to 3') sequences in FIG. 1.

It is this switch domain which is complementary to the "trigger" nucleic acid being detected, which as described above is either a particular viral nucleic acid or a nucleic acid encoding a particular human transcription factor acid. The trigger is represented by a'+b' (3' to 5') sequences in FIG. 1. The trigger sequence a' hybridizes by complementary base pairing to the single-stranded toehold domain denoted a. As the stem domain naturally associates and dissociates (i.e., "breathes"), trigger sequence b' then has the opportunity to migrate into the hairpin and hybridize to the ascending sequence of the stem domain, denoted b. This hybridization unwinds the stem domain further and makes the RBS accessible to the ribosome, and this in turn enables translation of the downstream coding region, and production of the encoded protein (e.g., the reporter protein). In the absence of a trigger nucleic acid, the toehold domain remains single-stranded, the riboregulator typically remains closed, the RBS remains inaccessible to the ribosome machinery, and there is no or little translation of the downstream coding domain.

As will be understood, in their final form, riboregulators are RNA molecules that possess an RBS and are acted upon by ribosome machinery to produce an encoded protein. While they may be provided to a system, such as a cell-free system or an in vivo system, as RNAs, this is likely to be inefficient given the inherent instability of RNA. Instead, they are typically provided in a DNA form, conjugated to a promoter, such as but not limited to a T7 promoter, and are then produced in an RNA form through transcription from the T7 promoter. The sequences provided in the sequence listing submitted herewith and as part of this specification are DNA sequences that comprise the riboregulator sequence in a DNA form (i.e., there is a T in the sequence provided whereas the RNA counterpart would have a U in that position). Thus, these sequences are understood to comprise the DNA form of a riboregulator (with Ts) as well as the RNA form (with Us). As will be discussed below, these sequences also comprise elements in addition to the riboregulator elements discussed above.

The nucleic acids provided as SEQ ID NOs: 1-244,000 are DNAs that comprise the riboregulator elements described above. These sequences have a common structure/sequence as follows, in a 5' to 3' order:

```
Promoter sequence: T7 promoter, 20 nt,
                        (SEQ ID NO: 244001)
TAATACGACTCACTATAGGG;
```

Switch domain sequence: complete toehold (12 nt) and entire ascending stem (18 nt), 30 nt in total; variable sequence;

```
Loop domain sequence: includes RBS, 11 nt,
                        (SEQ ID NO: 244002)
AACAGAGGAGA;
```

Stem domain 1 sequence: top half of descending stem, 6 nt, variable sequence will be dictated by switch domain sequence, as illustrated in FIG. 6A;
ATG or AUG: start codon, 3 nt;
Stem domain 2 sequence: bottom half of descending stem, 9 nt, variable sequence will be dictated by switch domain sequence, as illustrated in FIG. 6A;
Linker domain sequence: sequence encoding unstructured amino acids, 21 nt,

```
                        (SEQ ID NO: 244003)
AACCTGGCGGCAGCGCAAAG;
```

Post-linker sequence: ATG start of reporter gene, 3 nt.

Accordingly, each of the sequences in the enclosed sequence listing is 103 nucleotides in length. These nucleic acid sequences are provided as DNA strands, which are then transcribed from the T7 promoter into RNA strands which are able to self-hybridize and thereby adopt the riboregulator structure described above. Further, before use, each of these sequences may be conjugated (i.e., operably linked) to a coding domain at their 3' ends. These sequences may be provided in a replication vector and/or an expression vector, and optionally in a host cell.

This disclosure contemplates use of the entire 103 nt sequence, for example by conjugating such sequence to a coding domain. Alternatively, this disclosure contemplates use of the sequence presented by nucleotides 21-100, which represent the toehold domain, the hairpin domain, and the linker domain, preferably in RNA form (i.e., with Ts replaced with Us and with an RNA backbone).

A cell or a cell-free system may be contacted with the riboregulator in its DNA form, and it may be transcribed from the T7 promoter in order to form its RNA form. A sample to be tested may be contacted with the DNA form, provided such sample is capable of transcribing the DNA form. Alternatively, the sample to be tested may be contacted with the RNA form, and thus the sample to be tested may be contacted with a riboregulator RNA sequence beginning at the switch domain and having a coding domain. In relation to SEQ ID NOs: 1-244,000, this means that samples may be contacted with RNA versions of these sequences that lack nucleotides 1-20 but that comprise a coding domain conjugated to their 3' ends.

Use of riboregulators in vitro as nucleic acid diagnostic tools using cell-free protein synthesis (CFPS) systems have been described previously (3, 4, 15, 16), and reference can be made to such prior teachings.

It is to be understood therefore that in its RNA form, the riboregulator typically lacks the promoter sequence and it is conjugated to a coding domain as shown in FIG. 1.

It is also to be understood that other promoters may be used in place of the T7 promoter that is provided in SEQ ID NOs: 1-244,000.

The consensus sequence therefore comprises certain constant or invariant sequences including the promoter sequence, the loop domain sequence, the linker sequence, and the post-linker sequence. The switch domain sequence, the stem domain 1 sequence, and the stem domain 2 sequence are all variable (i.e., they will vary between riboregulators), although they will have regions of complementarity to each other. This is illustrated in FIG. 6A which shows that stem domain 1 sequence is complementary to a 3' region of the switch domain, and stem domain 2 sequence is complementary to a 5' region of the switch domain. The complementarity of these regions results in the stem domain.

In general, the hairpin and stem domains described herein form at and are stable under physiological conditions, e.g., conditions present within a cell (e.g., conditions such as pH, temperature, and salt concentration that approximate physiological conditions). Such conditions include a pH between 6.8 and 7.6, more preferably approximately 7.4. Typical temperatures are approximately 37° C.

Various of the nucleic acids provided in this disclosure may be regarded as non-naturally occurring, artificial, engineered or synthetic. This means that the nucleic acid is not found naturally or in naturally occurring, unmanipulated, sources. A non-naturally occurring, artificial, engineered or synthetic nucleic acid may be similar in sequence to a naturally occurring nucleic acid but may contain at least one artificially created insertion, deletion, inversion, or substitution relative to the sequence found in its naturally occurring counterpart. A cell that contains an engineered nucleic acid may be regarded as an engineered cell.

In some instances, the riboregulators are operably linked to coding regions that encode reporter proteins. Such reporter proteins are typically used to visualize activation of the riboregulator and thus presence of the trigger nucleic acid in the sample being analyzed. Reporter proteins suitable for this purpose include but are not limited to fluorescent or chemiluminescent reporters (e.g., GFP variants, luciferase, e.g., luciferase derived from the firefly (*Photinus pyralis*) or the sea pansy (*Renilla reniformis*) and mutants thereof), enzymatic reporters (e.g., β-galactosidase, alkaline phosphatase, DHFR, CAT), etc. The eGFPs are a class of proteins that has various substitutions (e.g., Thr, Ala, Gly) of the serine at position 65 (Ser65). The blue fluorescent proteins (BFP) have a mutation at position 66 (Tyr to His mutation) which alters emission and excitation properties. This Y66H mutation in BFP causes the spectra to be blue-shifted compared to the wtGFP. Cyan fluorescent proteins (CFP) have a Y66W mutation with excitation and emission spectra wavelengths between those of BFP and eGFP. Sapphire is a mutant with the suppressed excitation peak at 495 nM but still retaining an excitation peak at 395 and the emission peak at 511 nM. Yellow FP (YFP) mutants have an aromatic amino acid (e.g. Phe, Tyr, etc.) at position 203 and have red-shifted emission and excitation spectra.

The riboregulators comprise an RBS. Exemplary RBS sequences include, but are not limited to, AGAGGAGA (or subsequences of this sequence, e.g., subsequences at least 6 nucleotides in length, such as AGGAGG). Shorter sequences are also acceptable, e.g., AGGA, AGGGAG, GAGGAG, etc. Numerous synthetic ribosome binding sites have been created, and their translation initiation activity has been tested. The activity of any candidate sequence to function as an RBS may be tested using any suitable method. For example, expression may be measured as described in Example 1 of published PCT application WO 2004/046321, or as described in reference 53 of that published PCT application, e.g., by measuring the activity of a reporter protein encoded by an mRNA that contains the candidate RBS appropriately positioned upstream of the AUG.

Particular Riboregulators

Some of the riboregulators of this disclosure are specific for (i.e., they specifically hybridize to, and thus can be used to detect) nucleic acids (DNA or RNA) from particular viruses. These viruses are astrovirus, cardiovirus, chikungunya virus, cosavirus, coxsackie virus, dengue virus, ebola virus, hantavirus, human immunodeficiency virus, human parvo virus, human rhino virus, influenza virus: h1n1, influenza virus: h3n2, lassa virus, leishmanial virus, Marburg virus, papilloma virus, poliovirus, rabies virus, smallpox virus, west nile virus, yellow fever virus, and zika virus. The switch domain of these virus-specific riboregulators will hybridize to a nucleic acid, such as a transcript, from one of these viruses. Table 5 provides details relating to the SEQ ID NO: viral specificity.

Of particular interest are riboregulators having a nucleotide sequence selected from the group consisting of SEQ ID NOs: 43841, 9602, 62866, and 19367. Of particular interest are riboregulators that are specific for smallpox virus, dengue virus, and human rhino virus.

Some of the riboregulators of this disclosure are specific for (i.e., they specifically hybridize to, and thus can be used to detect and optionally measure) nucleic acids (DNA or RNA) that encode particular human transcription factors. These human transcription factors are AC097634.4, ACTB, ACTL6A, ACTN4, AEBP1, AEBP2, AGO1, AGO2, AHR, AIRE, AKNA, AL121581.1, ALX1, ALX4, ANHX, AR, ARHGAP35, ARID3A, ARID3B, ARID3C, ARID4A, ARID4B, ARID5A, ARID5B, ARNT, ARNT2, ARNTL, ARNTL2, ARRB1, ARX, ASCL1, ASCL2, ASCL3, ASCL4, ASCL5, ASH2L, ATF1, ATF2, ATF3, ATF4, ATF5, ATF6, ATF6B, ATMIN, ATOH1, ATOH8, ATXN3, BACH1, BACH2, BARHL1, BARHL2, BARX1, BARX2, BASP1, BATF, BATF2, BATF3, BAZ2A, BCL11A, BCL11B, BCL6, BCL6B, BCOR, BHLHA15, BHLHE40, BHLHE41, BORCS8-MEF2B, BRCA1, BRD7, BRF2, CALCOCO1, CARF, CARM1, CBX4, CC2D1A, CC2D1B, CCAR1, CCNT1, CDC5L, CDK12, CDK13, CDK5RAP2, CDK9, CDX1, CDX2, CDX4, CEBPA, CEBPB, CEBPD, CEBPE, CEBPG, CEBPZ, CGGBP1, CHD2, CHD4, CHD7, CIART, CIITA, CITED1, CLOCK, CNBP, CREB1, CREB3, CREB3L1, CREB3L2, CREB3L3, CREB3L4, CREBBP, CREBRF, CREM, CRX, CRY1, CRY2, CT476828.9, CTCF, CTCFL, CUX1, CUX2, CXXC1, DACH1, DBP, DDIT3, DDN, DEAF1, DHX36, DHX9, DLX1, DLX2, DLX4, DLX5, DMBX1, DMRT1, DMRT2, DNMT3A, DPF2, DR1, DRAP1, DUX4, E2F1, E2F2, E2F3, E2F4, E2F6, E2F7, E2F8, E4F1, EAF2, EBF2, EBF3, EBF4, EED, EGR1, EGR2, EGR3, EGR4, EHF, EHMT2, ELF1, ELF3, ELF4, ELF5, ELK1, ELK3, ELK4, ELL3, ELMSAN1, EN1, ENO1, EOMES, EP300, ERBB4, ERG, ESR1, ESR2, ESRRA, ESRRB, ESRRG, ESX1, ETS1, ETS2, ETV1, ETV2, ETV3, ETV4, ETV5, ETV6, ETV7, EZH2, FERD3L, FEZF1, FEZF2, FIGLA, FLI1, FOS, FOSB, FOSL1, FOSL2, FOXA1, FOXA2, FOXA3, FOXC1, FOXC2, FOXD1, FOXD3, FOXF1, FOXF2, FOXH1, FOXI1, FOXJ1, FOXJ2, FOXK1, FOXK2, FOXL2, FOXM1, FOXN4, FOXO3, FOXP2, FOXP3, FOXQ1, FOXS1, FUBP3, GABPA, GABPB1, GABPB2, GADD45A, GATA1, GATA2, GATA3, GATA4, GATA5, GATA6, GATAD2B, GBX2, GCFC2, GCM1, GFI1, GLI1, GLI2, GLI3, GLIS1, GLIS2, GLMP, GMEB1, GMEB2, GRHL1, GRHL2, GSC, GSX1, GTF2B, GTF3C1, GZF1, H2AFY, H2AFY2, H2AFZ, H3F3A, H3F3B, HAND1, HAND2, HDAC1, HDAC2, HDAC4, HDAC5, HDAC6, HELT, HES1, HES2, HES3, HES4, HES5, HES6, HES7, HESX1, HEY1, HEY2, HEYL, HHEX, HIC2, HIF1A, HINFP, HIVEP1, HLF, HLTF, HMGA1, HMGA2, HMGB1, HMGB2, HMX1, HMX3, HNF1A, HNF1B, HNF4A, HNF4G, HNRNPC, HNRNPK, HNRNPL, HNRNPU, HOXA10, HOXA2, HOXA3, HOXA4, HOXA5, HOXA6, HOXA7, HOXA9, HOXB1, HOXB2, HOXB3, HOXB4, HOXB5, HOXB6, HOXB7, HOXB9, HOXC10, HOXC11, HOXC4, HOXC5, HOXC6, HOXD10, HOXD13, HOXD3, HOXD4, HOXD8, HOXD9, HR, HSF1, HSF2, HSF4, HSF5, HSFX1, HSFX2, HSFX3, HSFX4, HSFY1, HSFY2, IER2, IFI16, IKZF1, IKZF2, IKZF3, IKZF4, IKZF5, INSM1, IRF1, IRF2, IRF2BP1, IRF2BP2, IRF2BPL, IRF3, IRF4, IRF5, IRF6, IRF7, IRF8, IRF9, ISL1, JARID2, JDP2, JMJD1C, JUN, JUNB, JUND, KAT2B, KAT7, KCNIP3, KDM1A, KDM2B, KDM3A, KDM3B, KDM5A, KDM6A, KDM6B, KLF1, KLF10, KLF11, KLF12, KLF13, KLF15, KLF16, KLF17, KLF3, KLF4, KLF5, KLF6, KLF7, KLF8, KMT2A, KMT2D, LDB1, LEF1, LHX2, LHX3, LITAF, LMO2, LMO4, LMX1A, LMX1B, LONP1, LRRFIP1, LYL1, MACC1, MAF, MAF1, MAFA, MAFB, MAFF, MAFG, MAFK, MAX, MAZ, MBD2, MBD3, MED1, MED12, MED8, MEF2A, MEF2B, MEF2C, MEF2D, MEIS1, MEIS2, MEN1, MEOX1, MEOX2, MESP1, MESP2, MITF, MIXL1, MLX, MLXIP, MLXIPL, MMP12, MNT, MRTFA, MSC, MSGN1, MSX1, MSX2, MTA1, MTA2, MTERF3, MTF1, MTF2, MTOR, MUC1, MXD1, MXD3, MXI1, MYB, MYBBP1A, MYBL1, MYBL2, MYC, MYCN, MYEF2, MYF5, MYF6, MYOCD, MYOD1, MYOG, MYPOP, MYT1, MYT1L, MZF1, NACC2, NANOG, NCOA2, NCOR1, NCOR2, NDN, NEUROD1, NEUROD2, NEUROD6, NEUROG1, NEUROG2, NEUROG3, NFAT5, NFATC1, NFATC2, NFATC3, NFATC4, NFE2, NFE2L1, NFE2L2, NFE2L3, NFIA, NFIB, NFIC, NFIL3, NFKB1, NFKB2, NFX1, NFXL1, NFYA, NFYB, NFYC, NHLH1, NHLH2, NKRF, NKX2-1, NKX2-2, NKX2-5, NKX2-6, NKX2-8, NKX3-1, NKX3-2, NKX6-1, NKX6-2, NLRC5, NME1, NONO, NOTCH1, NPAS2, NPAS4, NPM1, NR1D1, NR1D2, NR1H2, NR1H3, NR1H4, NR1I2, NR1I3, NR2C1, NR2C2, NR2E3, NR2F1, NR2F6, NR3C1, NR4A1, NR4A2, NR4A3, NR5A1, NR5A2, NR6A1, NRF1, NRIP1, NRL, NSD1, ONECUT2, ONECUT3, OSR1, OSR2, OTX1, OTX2, OVOL1, PARP1, PATZ1, PAX1, PAX2, PAX4, PAX5, PAX6, PAX8, PAX9, PAXBP1, PBX1, PBX2, PBX3, PCGF3, PCGF5, PCGF6, PDX1, PER1, PER2, PER3, PGR, PHB, PHOX2A, PHOX2B, PIH1D1, PITX1, PITX2, PITX3, PKNOX2, PLAG1, PLAGL1, POLRMT, POU1F1, POU2AF1, POU2F1, POU2F2, POU2F3, POU3F2, POU3F4, POU4F1, POU4F2, POU4F3, POU5F1, POU6F1, PPARA, PPARD, PPARG, PRDM1, PRDM11, PRDM12, PRDM13, PRDM14, PRDM15, PRDM2, PRDM4, PRDM5, PRDM6, PRDM7, PRDM9, PRDX5, PRKN, PRMT5, PROP1, PROX1, PRRX1, PSPC1, PTF1A, PURA, PURB, PURG, RAI1, RARA, RARB, RARG, RAX, RAX2, RB1, RBBP4, RBBP5, RBL1, RBL2, RBMX, RBPJ, RBPJL, RCOR1, RCOR2, RCOR3, REL, RELA, RELB, REST, RFX1, RFX2, RFX3, RFX4, RFX5, RFX6, RFX7, RFX8, RNF10, RORA, RORB, RORC, RPS3, RPTOR, RREB1, RRN3, RUNX1, RUNX2, RUNX3, RUVBL2, RXRA, RXRB, SAFB, SALL1, SALL2, SARS, SATB1, SATB2, SCRT1, SCRT2, SCX, SETX, SFPQ, SIN3A, SIRT1, SIX1, SIX2, SIX3, SIX4, SIX5, SIX6, SKIL, SMAD1, SMAD2, SMAD3, SMAD4, SMAD5, SMAD6, SMAD7, SMARCA2, SMARCA4, SMARCB1, SMARCC1, SMARCC2, SMARCD2, SMARCE1, SMYD3, SNAI1, SNAI2, SNAI3, SNCA, SOX1, SOX10, SOX11, SOX12, SOX13, SOX17, SOX18, SOX2, SOX21, SOX3, SOX4, SOX6, SOX7, SOX8, SOX9, SP1, SP2, SP3, SP5, SP7, SPI1, SPIB, SPIC, SREBF1, SREBF2, SRF, SSBP2, SSBP3, SSBP4, ST18, STAT1, STAT3, STAT5B, STAT6, STOX1, SUV39H1, SUV39H2, SUZ12, TAF1, TAF1B, TAF1C, TAF2, TAF5, TAF7, TAF7L, TAF9, TAF9B, TAL1, TAL2, TBL1X, TBL1XR1, TBP, TBPL1, TBPL2, TBR1, TBX15, TBX18, TBX19, TBX2, TBX20, TBX21, TBX22, TBX3, TBX5, TBX6, TBXT, TCF12, TCF15, TCF20, TCF21, TCF3, TCF4, TCF7, TCF7L1, TCF7L2, TCFL5, TEAD1, TEAD2, TEAD3, TEAD4, TEF, TFAM, TFAP2A, TFAP2B, TFAP2C, TFAP2D, TFAP2E, TFAP4, TFCP2, TFCP2L1, TFDP1, TFDP2, TFE3, TFEB, TFEC, TGIF1, THAP1, THAP11, THRA, THRAP3, THRB, TIPARP, TLX1, TNF, TOP1, TOX2, TOX3, TP53, TP63, TP73, TRERF1, TRIM24, TRPS1, TWIST1, TXK, UBTF, UHRF1, USP3, UTY, VAX1, VAX2, VDR, VEZF1, WBP2, WNT1, WNT11, WNT5A, WT1, XBP1, XRCC5, XRCC6, XRN2, YAP1, YBX1, YBX3, YY1, YY2, ZBED1, ZBTB14, ZBTB16, ZBTB17, ZBTB2, ZBTB20, ZBTB24, ZBTB4, ZBTB48, ZBTB5, ZBTB7A, ZBTB7B, ZC3H4, ZC3H6, ZC3H8, ZEB1, ZFHX2, ZFHX3, ZFHX4, ZFP42, ZFPM1, ZGPAT, ZHX3, ZIC1, ZIC2, ZIC3, ZIC4, ZIC5, ZKSCAN3, ZNF131, ZNF143, ZNF148, ZNF174, ZNF175, ZNF202, ZNF205, ZNF217, ZNF219, ZNF239, ZNF277, ZNF281, ZNF322, ZNF335, ZNF350, ZNF395, ZNF431, ZNF497, ZNF501, ZNF513, ZNF516, ZNF536, ZNF541, ZNF564, ZNF568, ZNF589, ZNF605, ZNF613, ZNF639, ZNF649, ZNF658, ZNF668, ZNF691, ZNF692, ZNF704, ZNF709, ZNF711, ZNF740, ZNF746, ZNF750, ZNF821, ZNF835, ZNF93, and ZSCAN21. Table 5 provides details relating to the SEQ ID NO: transcription factor specificity.

In some embodiments, the riboregulator is specific for STAT3 transcription factor, and it is used to detect and optionally measure the expression level of this transcription factor. Riboregulators specific for STAT3 are provided as SEQ ID NOs: 210632-210860.

Of particular interest are riboregulators having a nucleotide sequence selected from the group consisting of SEQ ID NOs: 164989, 111698, and 236638. Of particular interest are riboregulators that are specific for transcription factors NCOR1, E2F3 and ZNF175.

This disclosure refers to riboregulators that are specific for a particular virus or a particular transcription factor. This intends that the switch domain in such riboregulators is complementary to a nucleic acid sequence in or produced from the particular virus or to a nucleic acid coding for the particular transcription factor. The nucleic acid sequence in or produced from the particular virus or the nucleic acid coding for the particular transcription factor are considered triggers in this disclosure.

This disclosure contemplates variants of the riboregulators provided herein. For example, the disclosure contemplates variants that differ from the disclosed sequences by 1, 2, 3, 4 or 5 nucleotides, wherein such variants retain the ability to specifically hybridize to the original trigger of interest (i.e., the trigger of their parent riboregulator). Such variants may have a cell-free ON/OFF value that less than that of their parent riboregulator provided that such ON/OFF value is still suitable for use. The ON/OFF value may be for example 2, 3, 4, 5, or more.

The riboregulators may be defined by their strength, and this in turn may be defined by the level of expression of the coding domain in the presence (ON state) versus in the absence (OFF state) of the trigger nucleic acid. The riboregulators may have a cell-free ON/OFF value of about 2 to about 10, and may be further subdivided into those having an ON/OFF value of about 2 to about 5 and about 5 to about 8 and about 8 to about 10. In some instances, riboregulators with higher ON/OFF may be preferred. The ON/OFF of an individual riboregulator in a cell-free system may be determined as described in the Examples.

Applications/Uses

The riboregulators may be used in a number of applications. For example, they may be used to detect presence of nucleic acid such as an RNA in a sample, and such a method may comprise combining any one or a combination (e.g., 2) of the toehold riboregulators provided herein with a sample, wherein the riboregulator comprises a switch domain including a single-stranded toehold domain that is complementary to a nucleic acid (e.g., an RNA) in the sample, such as a nucleic acid encoding a transcription factor a viral protein (e.g., a transcription factor RNA or a viral RNA). The riboregulator comprises a coding domain that encodes a reporter protein, under conditions that allow translation of the coding domain in the presence of the nucleic acid (e.g., RNA) of interest but not in the absence of such nucleic acid (e.g., RNA). The method further comprises detecting the reporter protein as an indicator (or surrogate) of the nucleic acid (e.g., RNA) of interest. As used herein, conditions that allow translation of the coding domain are conditions that include all the necessary machinery to produce a protein from an RNA such as but not limited to ribosomes, tRNAs, and the like.

Samples to be tested include samples obtained from a subject. The subject may be a human or a non-human.

In some instances, the subject is a subject having, suspected of having, or at risk of having a condition associated with the presence of a particular viral nucleic acid (e.g., a viral RNA) such as an infection by one of the viruses listed above. Thus, for example, the subject may be a subject having, suspected of having, or at risk of having an astrovirus infection, a cardiovirus infection, a chikungunya virus infection, a cosavirus infection, a coxsackie virus infection, a dengue virus infection, an ebola virus infection, a hanta-virus infection, a human immunodeficiency virus infection, a human parvo virus infection, a human rhino virus infection, an influenza h1n1 virus infection, an influenza h3n2 virus infection, a lassa virus infection, a leishmanial virus infection, a Marburg virus infection, a papilloma virus infection, a polio virus infection, a rabies virus infection, a smallpox virus infection, a west nile virus infection, a yellow fever virus infection, or a zika virus infection.

In some instances, the subject is a subject having, suspected of having, or at risk of having a condition associated with the presence and optionally increased expression of a particular human transcription factor from the list provided herein. A condition associated with the presence and optionally increased expression of a particular human transcription factor from the list provided herein is cancer.

In some embodiments, the transcription factor is STAT3 and the cancer is epithelial cancer such as squamous cell carcinoma of the head and neck, breast, ovary, prostate or lung cancer. In some embodiments, the cancer is intrahepatic cholangiocarcinoma. The presence and/or expression level of STAT3 may be used to diagnose or to prognose a particular cancer.

In some instances, the disclosure contemplates use of more than one virus-specific riboregulator. For example, some methods may involve contacting a sample with a plurality of virus-specific riboregulators in order to detect the presence of a plurality of viruses at the same time, or at least to test for the presence of a plurality of viruses at the same time. In this way, a single sample may be used and screened for the presence of a number of viruses. In order to distinguish which virus(es) are present in the sample, the riboregulators may be distinguished from each other based on the reporter protein to which they are operably linked. For example, GFP may be used as the reporter protein for HIV specific riboregulators.

The disclosure further contemplates that one or more riboregulators specific for the same virus may be used together. This may help with increasing the sensitivity of the detection assay. For example, riboregulators having SEQ ID Nos: 43841 and 62866 may be used together to detect smallpox virus. In some instances, the riboregulators are physically separate and drive translation of their respective reporter protein. In other instances, the riboregulators are physically attached, for example as an AND or an OR gate, and may contributed collectively to translation of a single reporter protein. Reference can be made to published PCT application WO 2014/074648 for a discussion of AND OR gates in the context of concatenated riboregulators.

In some embodiments, the riboregulator is operably linked to a coding domain that encodes a suicide gene (or suicide protein). In this way, the riboregulator can be used to selectively kill cells that are infected with a particular virus selected from the list provided herein. Alternatively, the riboregulator can be used to selectively kill cells that have increased expression of a particular transcription factor, such as STAT3, and which may therefore be cancer cells or pre-cancerous cells. An exemplary suicide gene is thymidylate synthase, and a subject is administered ganciclovir following production of the thymidylate synthase. In some embodiments, the suicide gene is herpes simplex virus type 1 thymidine kinase (HSV1-TK).

The riboregulators may be used to detect targets of interest such as viruses, and thus diagnose exposure to or infection by such viruses. The riboregulators may be used with an unmanipulated sample. Alternatively, the sample may be processed prior to contact with the riboregulator. For example, the sample may processed in order to extract RNA. Additionally or alternatively, the sample may be process to amplify RNA.

There are various techniques, including isothermal techniques, for amplifying nucleic acids such as RNA. One such method, referred to as nucleic acid sequence based amplification (NASBA)-mediated RNA amplification, is described by Pardee et al. Cell, 165:1255-1266, 2016. For example, RNA may be amplified using a method that comprises reverse transcription of a target RNA of interest using a sequence-specific reverse primer to form an RNA/DNA duplex. This duplex is then contacted with RNase H to degrade the RNA template. A forward primer having a T7 promoter is then introduced and allowed to bind and initiate elongation from the complementary strand, to form a double-stranded DNA product. T7-mediated transcription is then used to generate copies of the target RNA. NASBA is initiated at a higher temperature (e.g., about 65° C.) and then followed by isothermal amplification at about 41° C.

When used together, the isothermal RNA amplification and riboregulator-mediated detection steps provide a relatively low-cost and low-resource detection strategy.

The step of contacting the sample with the riboregulator can be performed in solution. Alternatively it can be performed in a paper-based form, as described by Pardee et al. Cell, 165:1255-1266, 2016.

EXAMPLES

In order that the invention described herein may be more fully understood, the following examples are set forth. It should be understood that these examples are for illustrative purposes only and are not to be construed as limiting this invention in any manner.

Engineered RNA modules are programmable elements capable of detecting small molecules, proteins, and nucleic acids. While useful, predicting the behavior of these tools remains a challenge, a situation that could be addressed through enhanced pattern recognition from deep learning. Thus, we investigate Deep Neural Networks (DNN) to predict toehold switch function as a canonical riboswitch model in synthetic biology. To facilitate DNN training, we synthesized and characterized in vivo a dataset of 91,534 toehold switches spanning 23 viral genomes and 906 human transcription factors. DNNs trained on nucleotide sequences ($R^2=0.43$) outperformed previous state-of-the-art thermodynamic and kinetic models ($R^2=0.0001-0.04$) and allowed for human-understandable attention-visualizations (VIS4Map) to identify failure modes. This deep learning pipeline constitutes a major step forward in engineering and understanding of RNA synthetic biology.

Materials and Methods

Toehold Switch Architecture Selection

The first-generation toehold switch architecture from Green et al. (SI-1) was selected in order to maximize the sequence variability in switch regions contributing to secondary structure. Where in later designs the trigger RNA only unwound a fraction of the stem (SI-1-3), in this earlier design the entire hairpin stem was variably complementary to the trigger, increasing the diversity of characterized RNA hairpins (FIG. 1A). An alternative fused ON state was also utilized. Normally, toehold switches detect the presence of a separate trigger RNA transcribed in trans to the OFF-state switch mRNA. However, for the testing of a large library of toehold-switch pairings, a two-plasmid system becomes intractable because each switch is designed around a specific cognate trigger. A two-plasmid system can also increase stochasticity caused by copy number variability. Green et al. (SI-1) found a strong positive correlation between conditions when the trigger is fused to the switch and conditions when un-fused, separate triggers are transcribed in excess. We confirmed this correlation ourselves on a subset of twenty toehold switches by comparing the signal from the alternative fused ON state used in our library to the measured ON/OFF from Green et al. (SI-1). Green et al have stated that due to a low switch plasmid copy number their OFF state rarely exceeded background autofluorescence, meaning that their reported ON/OFF ratios are essentially ON state measurements. The resulting comparison of signal from the alternative fused ON state we measured and the un-fused ON state measured by Green et al using a two-plasmid system resulted in a Pearson R=0.8567, as seen in FIG. 6B. Thus, the ON state of the switch can be reliably approximated by fusing the trigger RNA to the 5' end of the switch mRNA using a constant, unstructured linker sequence (FIG. 1A, 6A), allowing for the direct synthesis of trigger-switch cognates on a single plasmid.

Library Trigger Sequence Selection

Viral genomes were obtained on Nov. 6, 2018, from the NCBI/NIH website (genome/viruses). Each retrieved genome was tiled 30 bp at a time (the trigger length), with a stride of 5 bp, spanning the respective genome. Human transcription factors were obtained using ENSEMBL 94 BioMart (SI-4) utilizing the Gene Ontology term GO:0044212 (transcription regulatory region DNA binding). The coding region of each transcription factor was tiled 30 bp at a time with a stride of 10. A remaining portion of the designs (~10,000) was based on random 30 bp triggers.

Toehold Library Synthesis

We designed 244,000 toehold switch variants using 230 bp oligos, which were ordered and synthesized by Agilent. For each toehold switch variant, the oligo was designed containing the following sequence components in order from 5' to 3': 20 nt of common backbone, a T7 Promoter, the 30 nt Trigger sequence, a 20 nt unstructured Linker, the 12 nt Toehold, the 18 nt Ascending Stem, a 11 nt SD-containing Loop, the 18 nt Descending Stem including the start codon, a 21 nt AA-Linker, and the first 15 nt of the GFP gene. A schematic of the design can be found in FIG. 6A. In the previous validation of the fused trigger approach by Green et al. (SI-1), only part of the trigger was fused to avoid recombination of long repeated sequences, but the nature of our flow-seq pipeline allowed us to avoid this issue since the integrity of all variants was confirmed after measuring fluorescence through next-generation sequencing (NGS). The oligos were received at a stock amount of 10 pmol, which we diluted in 500 uL TE buffer for a working concentration of 20 nM. Of this working stock, 0.25 uL was used in 50 uL qPCR reactions using NEB Q5 polymerase 2×MM with 50 nM final concentration of appropriate primers. Two separate amplifications were done from the working stock of the oligo library for the ON and OFF states, respectively. One amplification, for the ON state, used a primer hybridizing to the 5' common backbone region. The resulting insert contained both the Switch RNA module and the Trigger attached to its 5' end. The second amplification, for the OFF state, used a primer hybridizing to the 20 nt unstructured Linker and included a T7 promoter and the 5' common backbone region in its tail. The OFF-state insert contained only the Switch RNA module without the Trigger module attached. See FIG. 6A for a full schematic of the amplification scheme. A third amplification linearized a ColE1 plasmid backbone for subsequent ligation. This backbone was the same ColE1 backbone as was used in Green et al. (SI-1) for transcribing trigger RNAs, but with a GFPmut3b-ASV gene inserted. All amplicons were cleaned from their reaction buffers by using carboxyl-coated magnetic beads (SI-5) (protocol 4.3): 1× concentration of beads to clean the longer linear backbone product, and 2× bead concentration to clean the smaller insert products. Both inserts were ligated separately into the ColE1 backbone in front of the GFPmut3b-ASV gene using golden gate cloning, as follows. The linearized plasmid backbone was diluted to 500 ng total mass. The ON or OFF insert was added according to a 1:1 molar ratio of insert to plasmid backbone. The inserts and backbone dilutions were prepared into 50 uL ligation reaction volumes, containing 5 uL NEB buffer 3.1, 5 uL T4 ligase buffer, 1 uL BsmBI, 0.5 uL Dpn1, 1 uL T4 ligase, and any remaining volume with nuclease-free water. The 50 uL reaction was placed into a thermocycler for 100 cycles of two steps: 16 C for 10 min and 37 C for 10 min. A final enzyme inactivation step at 65 C for 15 min was done. The ligation products were precipitated out of their reaction buffers using ethanol precipitation. The 50 uL ligation reactions were added to 1.5 mL Eppendorf tubes containing 150 uL of pure ethanol, 5 uL 0.3M sodium acetate (pH 5.2), and 1 uL glycoblue. Tubes were left on dry ice for 20 min and then immediately placed in a 4 C tabletop centrifuge and spun at max RPM for 30 min. Tubes were decanted, and 175 uL of 70% ethanol was added to the tube containing the pellet. Tubes were spun at max speed for 5 min. Tubes were then removed from the centrifuge, decanted, and allowed to dry for 15 min. Ligation products were then eluted in 4 uL TE buffer. For initial library transformation, 50 uL EclonI Supreme cells were given the full 4 uL ligation product elution and electro-transformed. Transformation efficiencies exceeding $10^7$ CFU/mL were achieved, and the expanded cells were harvested using a MaxiPrep kit (Qiagen). The resulting pool of plasmids was then electroporated into BL21 star *E. coli*, where transformation efficiencies exceeding $10^6$ were achieved.

Flow-Seq Pipeline

Induction was achieved by expanding BL21 cells overnight at 37 C in LB media with carbenicillin (carb) selection and then diluted 50× into fresh media. After the cells reached OD600 of 0.3 at 37 C (~2 hours of growth), 0.2 mM IPTG was added, and the cells were allowed to express for another 3 hours at 37 C. The cells were then moved to room temperature and sorted on a Sony SH800 FACS machine with four bins. A positive control consisting of Switch #4 from Green et al. (SI-1), one of the highest performing switches from that study's first-generation design, was cloned both in its OFF state and in the modified fused-trigger ON state. This positive control switch was then used to mark the highest and middle bins of GFP signal, while a negative control consisting of a pUC19 plasmid (containing no GFP) was used to mark the lowest bin of GFP signal (FIG. 7). Approximately 40 million events were sorted for each library. Cells in collected bins were diluted 10× into fresh LB media with carb selection and allowed to expand overnight at 30 C. The expanded cells were then harvested using a MaxiPrep kit (Qiagen).

Deep Sequencing, Read Data Processing and Read Count Analysis

Plasmid collected from sorted cells was amplified using NEB Q5 polymerase 2×MM and primers targeting the common backbone region upstream and downstream of the variable toehold region. The resulting 184 bp (OFF) or 224 bp (ON) PCR products were then analyzed by NGS using a MiSeq or NextSeq instrument (Illumina). Raw paired-end sequencing reads were quality filtered and merged with PEAR 0.9.1. Only sequences matching our intended designs were retained for further analysis. For the ON and OFF libraries, respectively, 10,390,207 reads and 20,788,966 reads were mapped to a correct switch sequence. The individual fluorescence distribution of the ON and OFF state for each switch was measured by calculating its frequency in each bin and assigning a normalized signal metric in the range of [0,1] (FIGS. 1C, D). An ON/OFF metric was calculated as the difference between the ON and OFF signal metrics independently (FIG. 1E). Frequencies of each variant were tabulated for each cell-sorted bin and normalized to the total reads per bin. Each variant's functional value was computed as the weighted mean of its normalized frequencies across all bins, scaled between 0 and 1. The ON/OFF ratios were then calculated as the subtracted difference between ON and OFF (since the fluorescence data had been collected on a logarithmic scale), resulting in a range scaled between −1 and 1.

Library Quality Control

A second biological replicate of our flow-seq pipeline was carried out that produced 60,800 ON measurements, 98,295 OFF measurements, and 30,101 ON/OFF ratio measurements where both ON and OFF were available for the same switch. The $R^2$ and MAE between our two datasets were calculated at different read count thresholds. Based on the results (FIGS. 8A-B), five different QC thresholds were established, some of which also included standard deviation cutoffs (Table 1, FIG. 18). QC1 and QC2 contained OFF data with significantly worse $R^2$ compared to QC3, QC4, and QC5, but only QC1 contained OFF data with worse MAE. We determined that the inter-replicate drop in $R^2$ for OFF values was mainly due to the skewness of the data—indeed, the OFF data consistently showed worse $R^2$ values than the ON data throughout the paper, despite having consistently better MAE values. Therefore, we chose to trust in the inter-replicate MAE values more than the inter-replicate $R^2$ metric for the OFF data.

To further evaluate the different QC levels, the most stringent data (QC5) were withheld as a test set, and an MLP fed a one-hot representation of the toehold sequence was trained on the four lower QC levels. The results for both predictive $R^2$ and MAE showed QC1 to be of significantly inferior quality, but QC2, QC3, and QC4 to be of roughly similar quality (FIG. 9). This result was consistent with the fact that inter-replicate MAE was notably worse at the QC1 count threshold but essentially unchanged across the read count thresholds contained by QC2, QC3, and QC4. The QC2 dataset gave the best predictive results by a small margin and was also significantly larger than QC3 or QC4 (Table 1). With these analyses in mind, QC2 was chosen as the final threshold for inclusion in our dataset. Within the measured ON/OFF ratios in the QC2 dataset, 40,824 had triggers of viral origin, 47,005 had triggers of human origin, and 3,705 had randomly generated trigger sequences.

Cell-Free Switch Validation

Eight of the best switches and eight of the worst switches were synthesized as PCR products, as previously described (SI-2). Briefly, they were ordered as single Ultramer oligos (IDT) without the Trigger fused, from the T7 promoter to the first 36 nt of the common linker and GFP sequences. These were added to a GFP gene by a single PCR amplification step. Triggers were in vitro transcribed from separate oligos that contained the antisense sequence and the antisense T7 promoter, to which the sense strand of the T7 promoter was annealed. Trigger RNA was purified using an RNA Clean &

Concentrator kit (Zymo), while Switch DNA was purified using a MinElute kit (Qiagen). To a 5 uL PURExpress reaction were added 2 U/uL Murine RNAse Inh, 5 nM of Toehold Switch PCR product, and either no Trigger RNA or 10 uM of Trigger RNA. Measurements of GFP velocity can be found in FIG. 10. The exact Switches tested and their library assay measurements can be found in Table 2.

Calculations Made with ViennaRNA, Kinfold, and the RBS Calculator

All thermodynamic MFE and ensemble defect calculations, as well as kinetic Kinfold calculations, were obtained using a custom-made python code including libraries from packages such as Biopython (Ref: github.com/biopython/biopython), ViennaRNA (Ref: github.com/ViennaRNA/ViennaRNA), RNAsketch (Ref: github.com/ViennaRNA/RNAsketch) and Pysster (Ref: github.com/budach/pysster). Calculations of thermodynamic rational parameters to include in our database were obtained from toehold RNA sequences by taking each basal 145-nucleotide toehold sequence and then isolating different sections (e.g., GGG, Trigger, Loop1, Switch, Loop2, Stem1, AUG, Stem2, Linker, Post-linker) into distinct sub-sequences with biological relevance for functional analysis (see FIG. 6A, Table 4). Minimum Free Energy (MFE) was calculated for all these sections using the previously reported python-based ViennaRNA Library. MFE calculation using ViennaRNA also specifies a secondary structure in dot-parens-plus notation (unpaired base=dot, base-pair=matching parentheses, and nick between strands=plus). Ideal structures are assumed to be connected and free of pseudoknots. These ideal secondary structures for such sections are:

SwitchOFF='... (((((((((... (((((... ))))))... )))))))))'
SwitchOFF_GFP=' ... (((((((((... (((((... ))))-)) ... ))))))))) ... (((... (((((... ))))) ... ))) ... '
SwitchOFF_NoTo='((((((((... (((((... )))))) ... ))))))-))) ... (((... (((((... ))))) ... ))) ... '
SwitchON=' ... ((((((((((((((((((((((((... ))))-))))))))))))))))))))))) ... '
SwitchON_GFP=' ... (((((((((((((((((((((... ... ))))))))))))))))))))))) ... (((... (((((... )))-)) ... ))) ... '
ToeholdON=' ... (((((((((((... ))))))))))))'
Stem='((((((((... (((((... )))))) ... )))))))))'
StemTop='(((((... ))))))'

Ensemble defect as a rational parameter was calculated via ViennaRNA/NUPACK for each of the toehold switches in the above subsets of sequence regions: SwitchOFF, SwitchOFF_GFP, Switch_OFF_NoTo, SwitchON, SwitchON_GFP, ToeholdON, Stem, StemTop. This calculation used both the native (calculated from MFE) and the ideal (predefined above) dot-Bracket representation for each sequence to assess the average number of nucleotides that are incorrectly paired at equilibrium. Thirty rational parameters were calculated for each toehold using these methods (fourteen MFE values, eight ideal ensemble defect values, and eight native ensemble defect values).

Figures 12A, 12B:
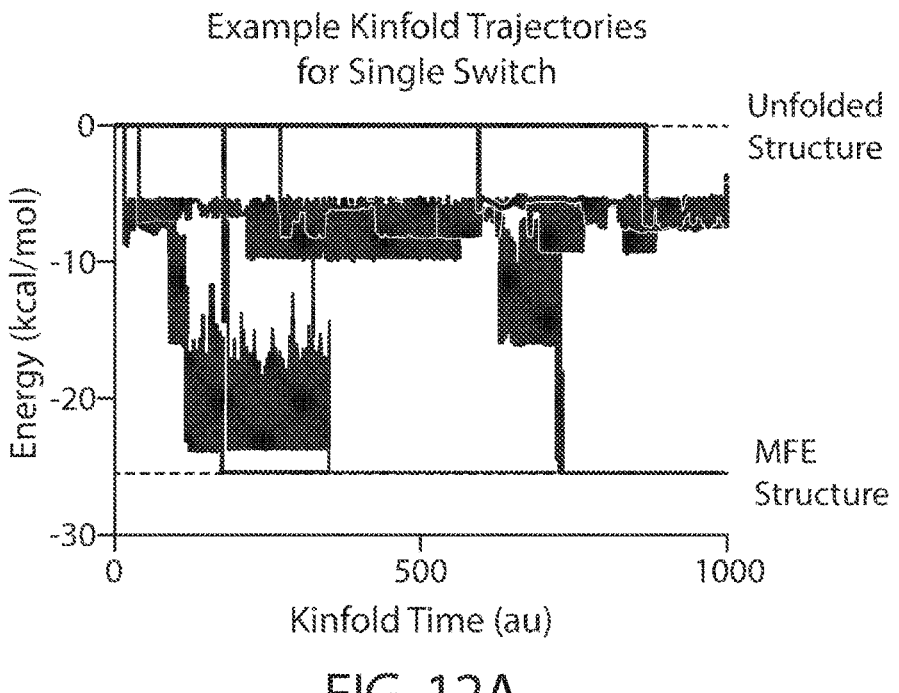
Figure 12C:
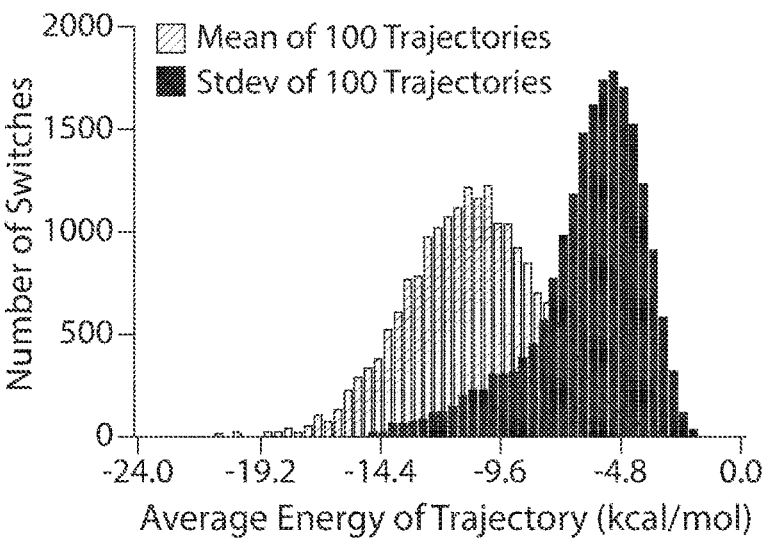
Figure 12D:
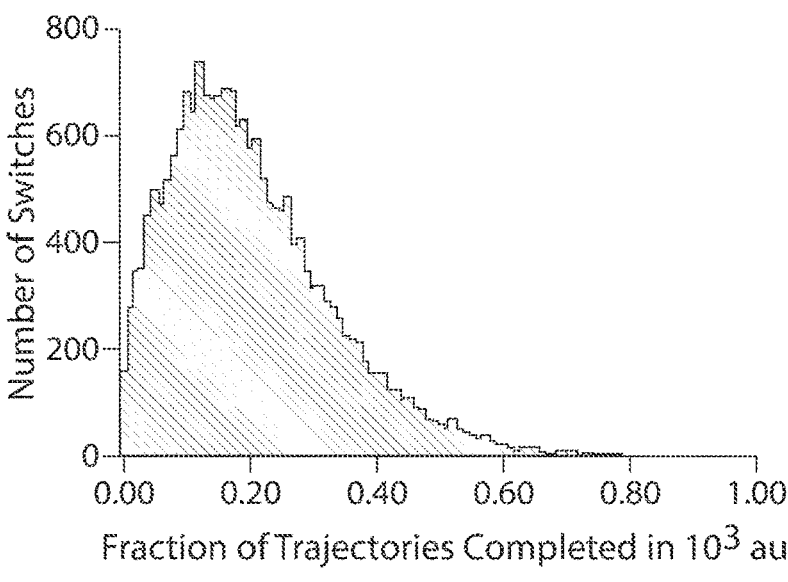

Kinetic analyses using Kinfold were run from the ViennaRNA package. The OFF-switch sequence was selected, spanning nucleotides 50 to 134 in Table 4 from the start of the toehold to the end of the linker. Due to the large size of the toehold switch RBS, Kinfold trajectories ran for 100-1000× longer than for RBS's previously analyzed relating to the RBS calculator in Borujeni et al. (SI-6) (FIG. 12B). Hence our analysis was scaled down to the QC4 dataset (containing 19,983 total switches), with 100 Kinfold trajectories run for each switch with a maximum stopping time of $10^3$ arbitrary Kinfold units (au). The energy and time at each step of each trajectory were recorded. If the MFE structure was reached within $10^3$ au, it was assumed that the RNA would remain in the MFE structure for the rest of the $10^3$ au timeframe. From each energy trajectory spanning $10^3$ au, the average energy (in kcal/mol) was calculated by integrating the energy-time curve and dividing by $10^3$. For each switch, the following features were extracted: the mean and standard deviation of the average energy of its 100 sampled trajectories (FIG. 12C), the ratio of the mean average energy to the MFE (FIG. 12E), and the fraction of trajectories that reached the MFE structure within the analyzed $10^3$ timeframe (FIG. 12D).

For predictions by the RBS Calculator, an API was used to access the most recent publicly available version (2.1). Due to limiting computational costs, the QC3 dataset was used instead of the QC2 dataset. For each switch, the translation initiation rate (TIR) of the on-target start codon was predicted for both the ON and OFF states ("SwitchON_GFP" and "SwitchOFF_GFP" respectively in Table 4).

K-Mer Motif Search

Figure 3A:
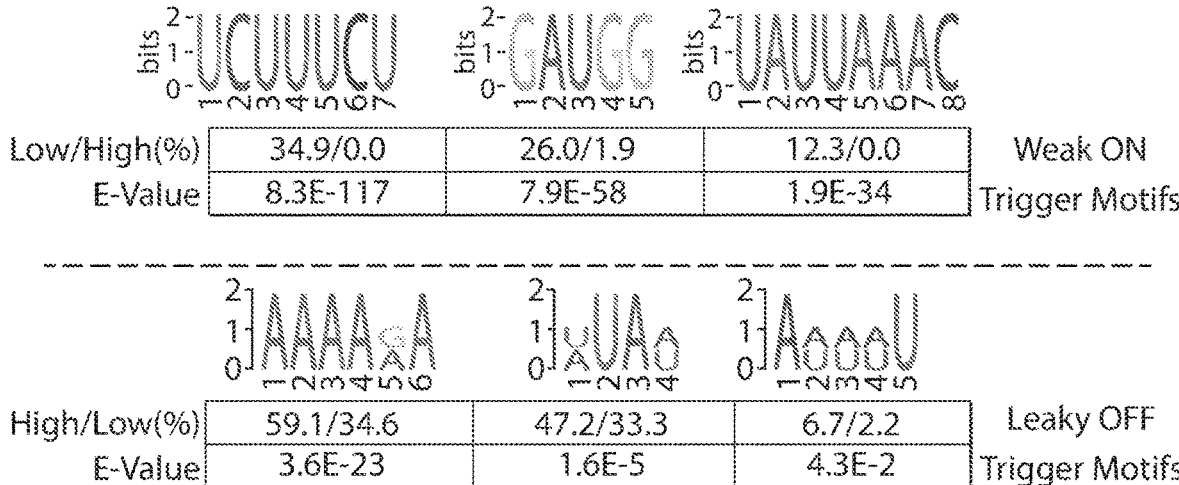

In order to compare sequence-level motifs between the best and worst variants measured in our dataset, we performed a k-mer search for over-represented sequence motifs at the tails of our observed functional values. We first filtered the variants for high quality, retaining those with a QC4 score or above. We then took the top and bottom 1,000 variants based on the ON and OFF functional values, respectively. We utilized DREME (SI-7) to test for enrichment or depletion of all possible subsequences of length 3-16 bases, using the indicated foreground and background frequencies. All results above the default E-value cutoff are shown (FIG. 3A, Table 3)

Deep Learning Model Architectures

MLP—Rational Features

The multilayer perceptron (MLP) model based on rational features included a 30-feature input followed by three dense fully connected layers of 25, 10, and 7 neurons, respectively, with rectified linear unit (ReLU) activation, batch normalization, and 20% dropout. This network was then fed to a final three-neuron layer (ON, OFF, ON/OFF) with linear activation for regression output, or to a final two-neuron layer (ON/OFF: binarized at +/−0.7) with softmax activation for classification output.

MLP—OneHot Seq

The MLP model based on the one-hot encoded full 145-nucleotide sequence input was achieved by using a flatten layer followed by three dense layers with ReLU activation, batch normalization, and 20% dropout. Dense layers used 128, 64, and 32 neurons, respectively. This network was then fed to a final three-neuron layer (ON, OFF, ON/OFF) with linear activation for regression output, or to a final two-neuron layer (ON/OFF: binarized at +/−0.7) with softmax activation for classification output.

MLP—Hybrid Rational Features/OneHot Seq

The ensemble MLP model was based on the rational features, as well as a one-hot encoded full 145-nucleotide sequence as input. To construct this model, two networks were assembled in parallel. The first network uses the same architecture for the MLP model with rational features, while the second network used the architecture of the MLP model for one-hot encoded 145-nucleotide sequences. Both networks were then concatenated and connected to a four-neuron dense fully connected layers with ReLU activation. This network was then fed to a final three-neuron layer (ON, OFF, ON/OFF) with linear activation for regression output, or to a final two-neuron layer (ON/OFF: binarized at +/−0.7) with softmax activation for classification output.

CNN—OneHot Seq

The Convolutional Neural Network (CNN) model based on the one-hot encoded full 145-nucleotide sequence as input was achieved by direct feeding of the input to three convolutional layers with ReLU activation, batch normalization, and 20% dropout. The convolutional layers used had 32, 64, and 128 filters of size 3, respectively. Same-padding was used with L1 and L2 kernel regularization. The output from the convolutional layers was flattened and fed to two fully connected sequential dense layers of 16 neurons each with ReLU activation, batch normalization, and 20% dropout. This network was then fed to a final three-neuron layer (ON, OFF, ON/OFF) with linear activation for regression output, or to a final two-neuron layer (ON/OFF: binarized at +/−0.7) with softmax activation for classification output.

CNN—2D Complementarity Map

The Convolutional Neural Network (CNN) model based on the one-hot encoded categorical 2D complementarity-directional matrix from the full 145-nucleotide sequence as input was achieved by direct feeding of the input to three convolutional layers with ReLU activation, batch normalization, and 30% dropout. The convolutional layers used had 32, 64, and 128 filters of size 5×5 respectively. Same-padding was used with L1 and L2 kernel regularization. The output from the convolutional layers was flattened and fed to two fully connected sequential dense layers of 16 neurons each with ReLU activation, batch normalization, and 20% dropout. This network was then fed to a final three-neuron layer (ON, OFF, ON/OFF) with linear activation for regression output, or to a final two-neuron layer (ON/OFF: binarized at +/−0.7) with softmax activation for classification output.

LSTM—OneHot Seq

The Long Short-Term Memory (LSTM) recurrent neural network model on the one-hot encoded full 145-nucleotide sequence as input was achieved by direct feeding of the input to a network with 128 recurrent units. The output of this was then connected to 100-neuron fully connected dense layer with ReLU activation, followed by batch normalization and 30% dropout. This network was then fed to a final three-neuron layer (ON, OFF, ON/OFF) with linear activation for regression output, or to a final two-neuron layer (ON/OFF: binarized at +/−0.7) with softmax activation for classification output.

All models were trained using a maximum of 300 epochs, considering a 20-epoch early stopping patience, which gets triggered upon lack of model improvement on the validation set. Batch size for all models was 64*(1+ngpus), where ngpus is defined as the number of used graphic processing units during model training. All trained regression models were verified for reported metrics using 10-fold cross-validation, while classification-trained models were evaluated on three shuffled test sets as indicated.

Complementarity Matrix and VIS4Map

Complementary maps were defined as a One-Hot Encoded Categorical 2D Complementarity-directional Matrix (total number of tensor dimensions=3) constructed by defining columns and rows of the matrix as the position of potential complementarity between any two given pairs of nucleotides in a single RNA sequence. The value in each position is defined as a one-hot encoded categorical variable according to the Watson-Crick pairing of the two nucleotides defining that position. Nucleotide pairings are assigned the following category: G-C (6)=[0 0 0 0 0 1], C-G (5)=[0 0 0 0 0 1 0], A-U (4)=[0 0 0 0 1 0 0], U-A (3)=[0 0 0 1 0 0 0], G-U (2)=[0 0 1 0 0 0 0], U-G (1)=[0 1 0 0 0 0 0], NonWCpairs (0)=[1 0 0 0 0 0 0]. VIS4Maps were generated using a modified algorithm, attention, activation maximization and saliency map visualization for Keras (Keras-Vis, Ref: github.com/raghakot/keras-vis) with tensorflow backend.

In this case, gradients were calculated from a regression model for all regions of the image to visualize what spatial features cause the predicted output to increase. To visualize the toehold regions that are mostly responsible for each prediction, small positive or negative gradients are highlighted using a normalization strategy. Given this information, such techniques allow us to generate heatmap-encoded saliency map images that spatially relate to the toehold regions in the complementarity map that lead to accurate predictions.

Results

Engineered ribonucleic acid (RNA) molecules with targeted biological functions play an important role in synthetic biology (1), particularly as programmable response elements for small molecules, proteins, and nucleic acids. Examples include riboswitches, riboregulators, and ribozymes, many of which hold great promise for a variety of in vitro and in vivo applications (1, 2). Despite their appeal, the design and validation of this emerging class of synthetic biology modules have proven challenging due to variability in function that remains difficult to predict (2-9). Current efforts aiming to unveil fundamental relationships between RNA sequence, structure, and behavior focus mostly on mechanistic thermodynamic modeling and low-throughput experimentation, which often fail to deliver sufficiently predictive and actionable information to aid in the design of complex RNA tools (2-9). Deep learning, by contrast, constitutes a set of computational techniques well suited for pattern recognition in complex and highly combinatorial biological problems (10-14), such as the sequence design space of RNA tools. However, the application of deep learning to predicting function in RNA synthetic biology has been limited by a notable scarcity of datasets large enough to effectively train deep neural networks. Toehold switches, in particular, represent a canonical RNA element in synthetic biology that could greatly benefit from deep learning approaches to better predict function and elucidate useful design rules.

Toehold switches are a class of versatile prokaryotic riboregulators inducible by the presence of a fully programmable trans-RNA trigger sequence (2-6, 15, 16). These RNA synthetic biology modules have displayed impressive dynamic range and orthogonality when used both in vivo as genetic circuit components (2, 5, 6), and in vitro as nucleic acid diagnostic tools using cell-free protein synthesis (CFPS) systems (3, 4, 15, 16). Similar to other RNA synthetic biology tools, a substantial fraction of toehold switches show poor to no measurable function when tested experimentally, and while efforts have been made to establish rational, mechanistic rules for improved performance based on low-throughput datasets (2-9, 15, 16), the practical utility of these approaches remains inconclusive. Thus, considering the wide applicability and general challenges of toehold switch design, our objective in this study was to develop a deep learning platform to predict toehold switch function as a canonical RNA switch model in synthetic biology.

To achieve this goal, we first aimed to expand the size of available toehold datasets using a high-throughput DNA synthesis and sequencing pipeline to characterize over $10^5$ new toehold switches. We then used this comprehensive new dataset to demonstrate that deep neural networks trained directly on switch RNA sequences can outperform rational thermodynamic and kinetic analyses to predict toehold switch function. Furthermore, we enhanced the transparency of our deep learning approach by utilizing a nucleotide (nt) complementarity matrix input representation to visualize learned secondary structure patterns in selected models. This attention-visualization technique, which we term VIS4Map (Visualizing Secondary Structure Saliency Maps), allowed us to identify RNA module failure modes by discovering secondary structures that our deep learning model used to accurately predict toehold switch function. The resulting dataset, models, and visualization analysis (FIG. 1) represent a substantial step forward for the validation and interpretability of high-throughput approaches to designing RNA synthetic biology tools, surpassing the limits of current mechanistic RNA secondary structure modeling.

Library Synthesis, Characterization, and Validation

As mentioned previously, a fundamental hurdle in applying deep learning techniques to RNA synthetic biology systems is the limited size of currently published datasets, which are notably smaller than typical dataset sizes required for training of deep network architectures in other fields (10, 17-21). For example, to date, less than 1000 total toehold switches have been designed and tested (2-6, 9, 15, 16), a situation that currently limits the synthetic biology community's ability to utilize deep learning techniques for analysis of this type of response molecules. Therefore, towards improving our understanding and ability to predict new functional RNA-based response elements, we first set out to synthesize and characterize an extensive in vivo library of toehold switches using a high-throughput flow-seq pipeline (22) for subsequent exploration using various machine learning and deep learning architectures.

Figures 2A, 2B:
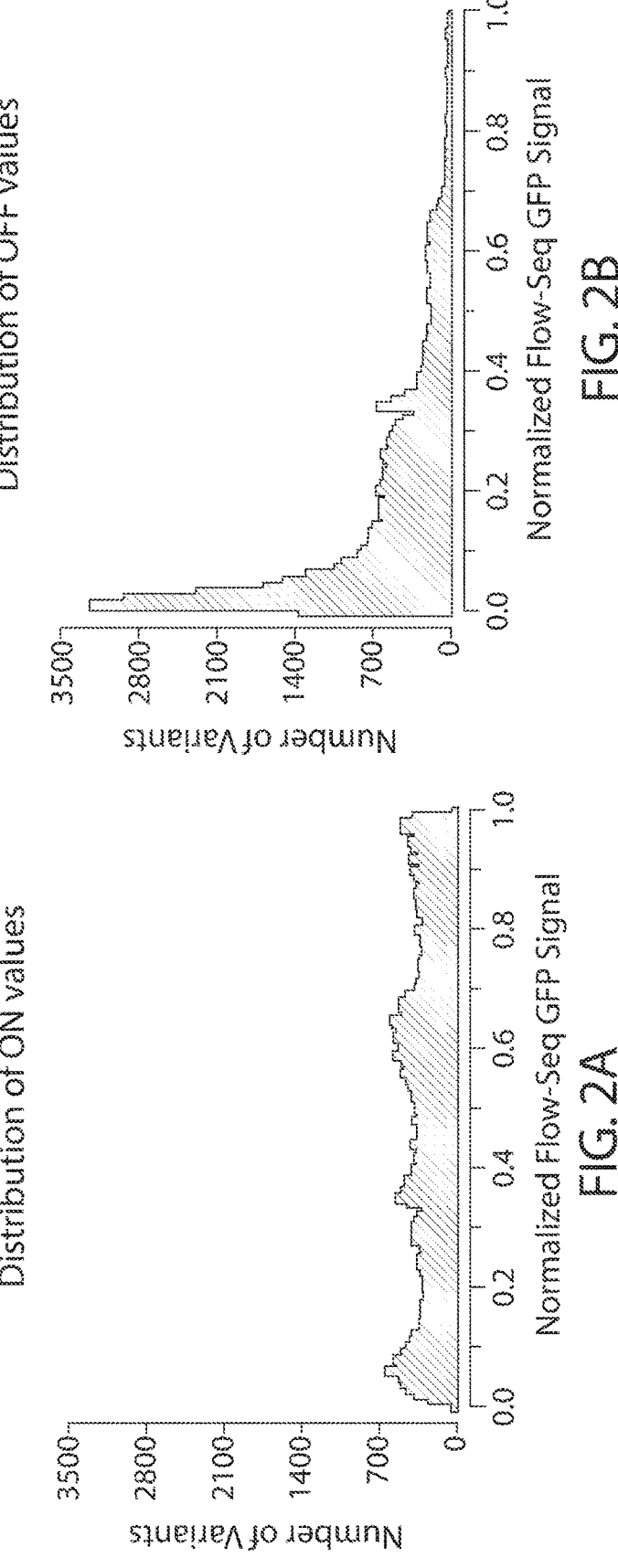
FIGS. 2A-F. Flow-seq toehold switch library characterization and trigger ontology. The distribution of recovered toeholds for (A) ON-state signals, (B) OFF-state signals, and (C) calculated ON/OFF ratios are shown (selected from quality control process #3, QC3 in FIG. 18 and Table 1). (D) Validation results for toehold switches expressed in a PUR-Express cell-free system with un-fused trigger RNA, including eight low-performing (poor, ON/OFF <0.05) and eight high-performing (good, ON/OFF >0.97) samples. Obtained flow-seq data show competency in performance-based switch classification within this distinct biological context.
Figures 2C, 2D:
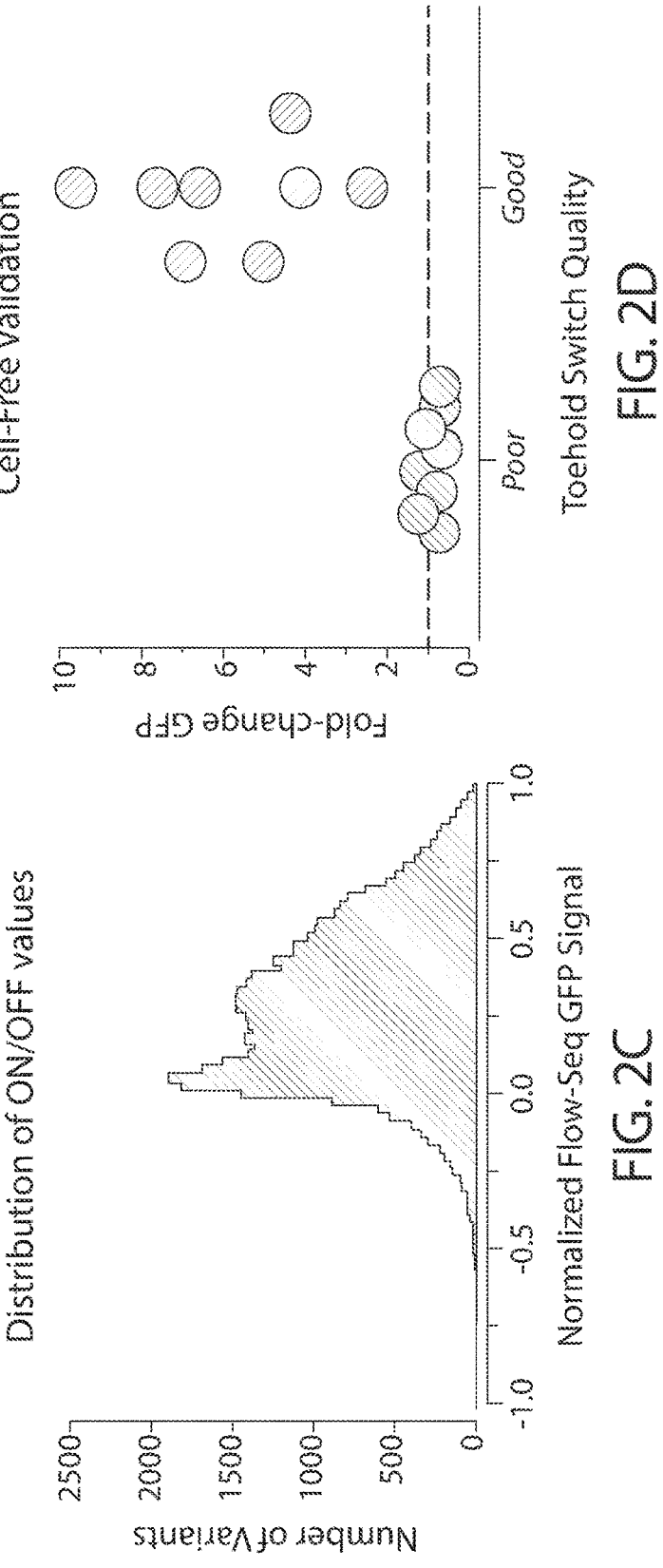
Figure 2E:
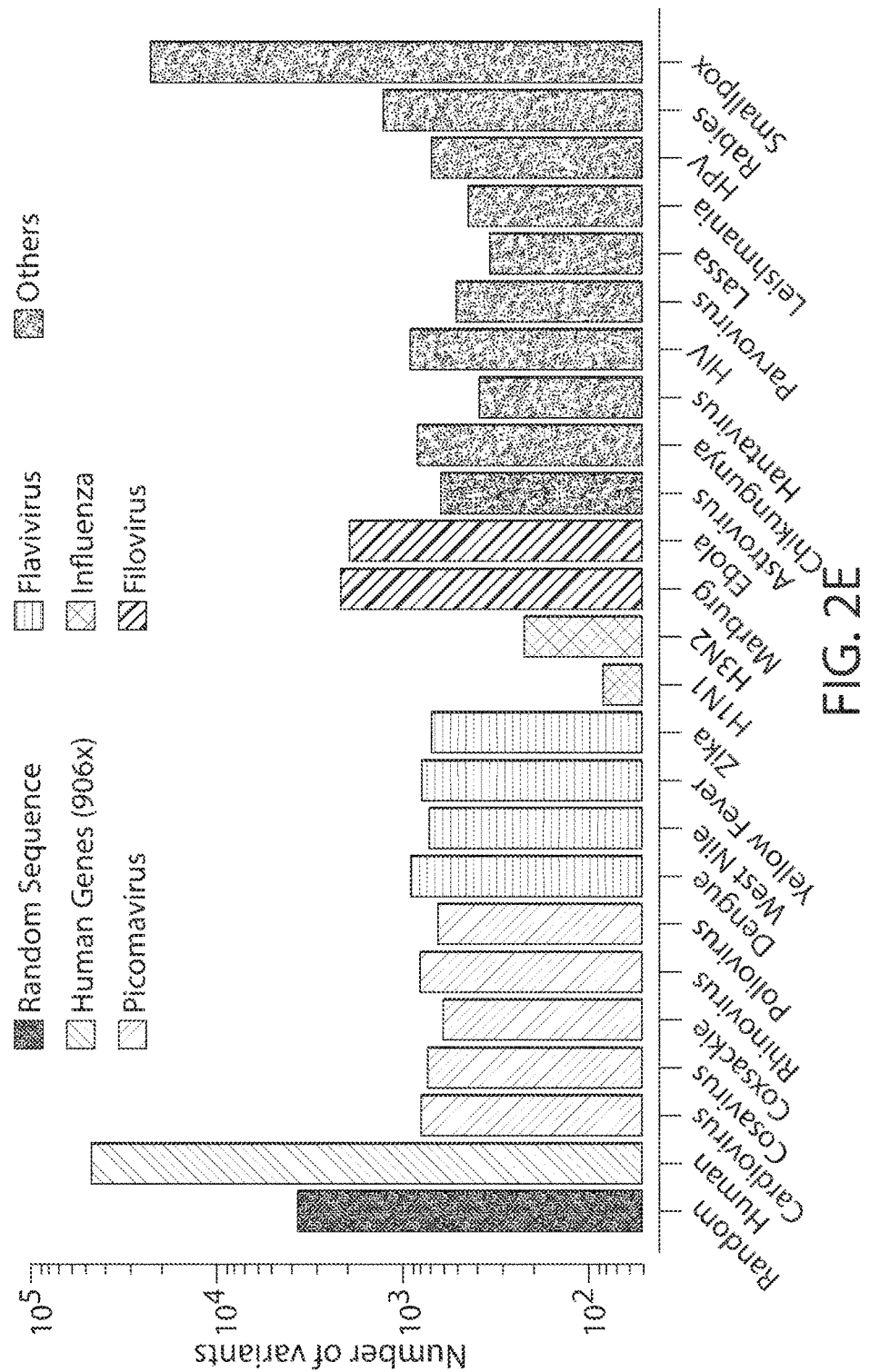
Figure 2F:
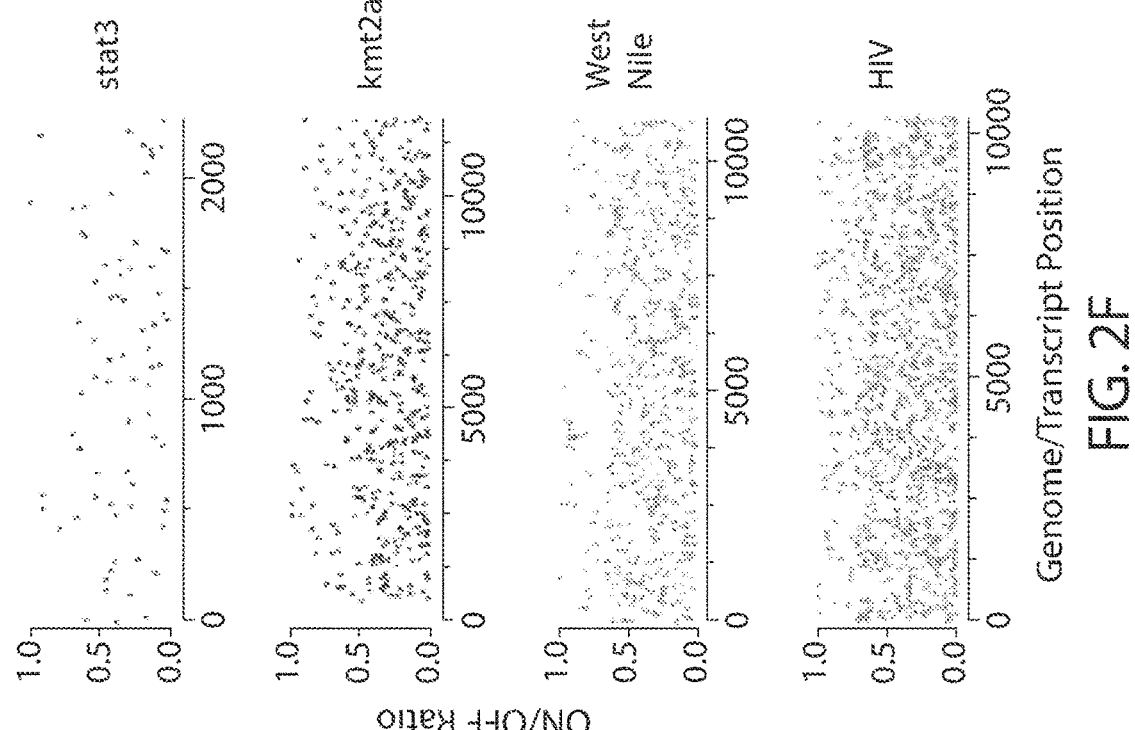

Our toehold switch library was designed and synthesized based on a large collection (244,000) of putative trigger sequences, spanning the complete genomes of 23 pathogenic viruses, the entire coding regions of 906 human transcription factors, and ~10,000 random sequences. From a synthesized oligo pool, we generated two construct libraries, for ON and OFF states, which were subsequently transformed into BL21 *Escherichia coli* (FIGS. 1, 6A-B). The first library contained OFF toehold switch constructs that lacked a trigger, while the second library of ON constructs contained the same toeholds with the complementary triggers fused to their corresponding switches. The two libraries were then sorted on a fluorescence-activated cell sorter (FACS) using four bins (FIGS. 1, 7), and the toehold switch variants contained in each bin were quantified using next-generation sequencing (NGS) to recover their individual fluorescence distributions from raw read counts (FIG. 1). After quality control (Table 1), the toehold switch library contained 109,067 ON state measurements (FIG. 2A), 163,967 OFF state measurements (FIG. 2B), and 91,534 ON/OFF paired difference ratios (FIG. 2C), where both ON and OFF states were characterized for each switch (FIGS. 2E,F). ON and OFF data were normalized from 0 to 1, resulting in an ON/OFF difference ratio normalized from −1 to 1.

Since RNA synthetic biology tools such as toehold switches are often used within in vitro cell-free systems (3, 4, 15, 16), we validated our in vivo ON/OFF measurements in an in vitro setting to ensure these were reasonable indicators of switch performance in a CFPS system. To achieve this, we selected eight high-performance switches and eight low-performance switches, and individually cloned and characterized them in a PURExpress CFPS (FIGS. 1D, 10 and Table 2). All low-performance switches showed no induction, while the high-performance switches showed a spread of cell-free ON/OFF ratios between 2 and 10 (p<0.0001 between high and low switches, two-tailed t-test). These results confirm that while the performance of toehold switches in vivo and in vitro may differ, in vivo measurements can still be used to classify categorically whether a switch will function in vitro.

Rational Analysis Using Thermodynamic RNA Secondary Structure Models

Figure 3B:
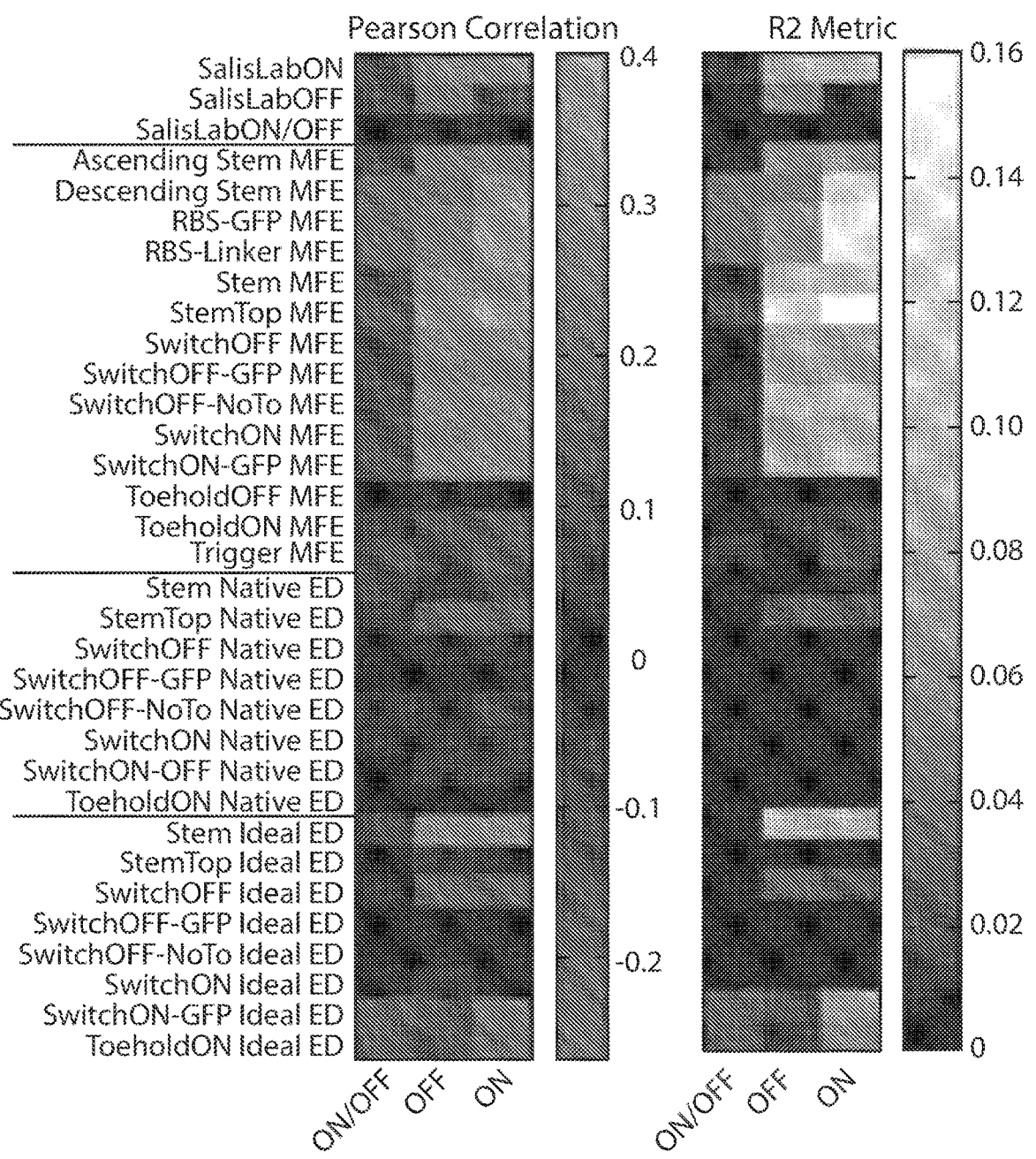

Before initiating the exploration of deep learning models to predict function in our large-scale toehold switch library, we sought to determine whether traditional tools for analyzing synthetic RNA modules could be used to accurately predict toehold switch behavior, including k-mer searches and mechanistic modeling using thermodynamic parameters. K-mer searches of biological sequence data are often used to discover motifs, and while certain overrepresented motifs were found in our dataset (FIG. 3A and Table 3), utilization of these did not significantly improve functional predictions of switch behavior. Other current state-of-the-art approaches for designing RNA synthetic biology tools primarily analyze secondary structure using thermodynamic principles (23-25). Following such prior works, we used NUPACK (23) and ViennaRNA (25) software packages to calculate a total of 30 rational features for our entire library, including the minimum free energy (MFE), ideal ensemble defect (IED), and native ensemble defect (NED) of the entire toehold switch library as well as various sub-segments in each sequence (Table 4). A number of these parameters had previously been reported to correlate with experimental toehold switch ON/OFF measurements for smaller datasets (2), and NUPACK's design algorithm, in particular, is set to optimize IED when proposing target RNA secondary structures (3, 4, 15, 23). However, when analyzing these rational features with our larger dataset, we found them to be poor predictors of toehold switch function (FIGS. 3B, 11A-B). In modest agreement with the findings of Green et al. (2), the MFE of the RBS-linker region showed the highest correlation of this feature set for ON/OFF ($R^2$: ON=0.14, OFF=0.06, ON/OFF=0.04), with NUPACK's IED also showing above-average correlation ($R^2$: ON=0.07, OFF=0.02, ON/OFF=0.03). While measurable, these correlation metrics were far too weak for practical use in computer-aided design of this specific RNA synthetic biology tool (3, 4, 15, 23).

Moving forward, we explored the use of more complex thermodynamic models that take into account well-established hypotheses for translation initiation and the ribosome docking mechanism in combination with multiple thermodynamic features to improve their predictions (26-31). One of the most developed of these models is the Ribosome Binding Site (RBS) calculator (v2.1; Salis Lab); a comprehensive model parameterized on thousands of curated RBS variants (26-29). We used the RBS calculator to predict the ON and OFF translation initiation rates for our toehold switches, but also found low predictive performance comparable to other rational features (FIG. 3B) when tested on our database ($R^2$: ON=0.09, OFF=0.05, ON/OFF=0.0001).

Figure 12E:
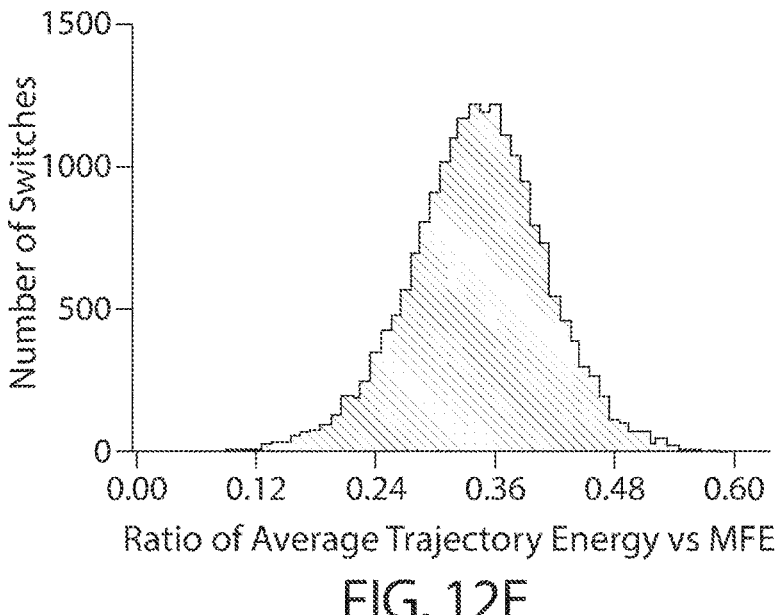
Figure 12F:
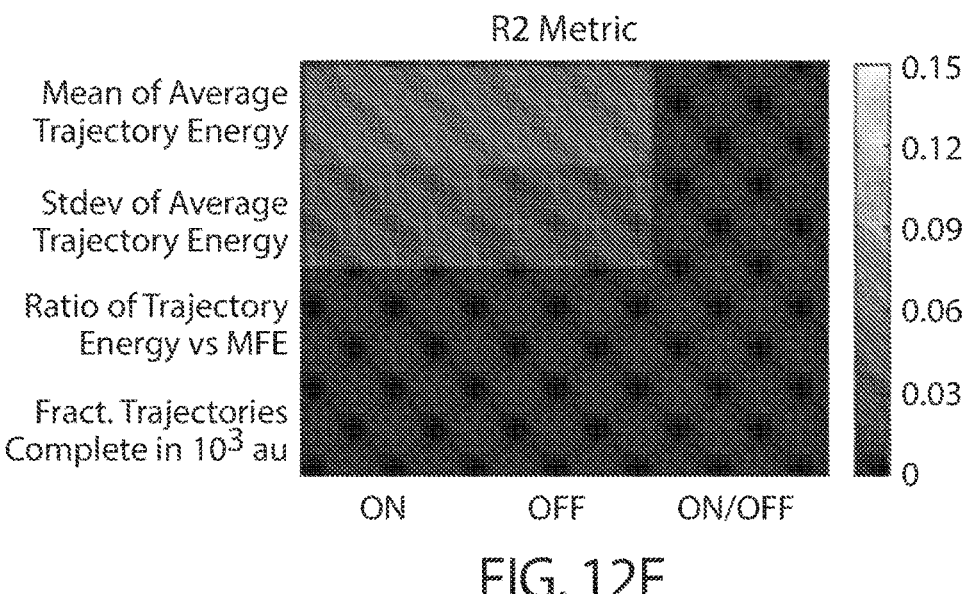

One potential explanation for the limited predictive power of current thermodynamic models for RNA folding tasks concerns the influence of kinetically stable secondary structure intermediates that may compete with thermodynamic equilibrium states (29, 32). To determine whether a kinetic analysis of toehold switch folding dynamics could help explain our experimental results, we calculated four additional features based on kinetic trajectories using the Kinfold package (33) (FIG. 12A-F). As with predictions obtained using other thermodynamic models, these kinetic features showed poor correlations ($R^2$: ON=0.04, OFF=0.04, ON/OFF=0.001 for the best feature) to our empirical dataset (FIG. 12E). Considering these results, the cause of limited function predictions from thermodynamic and kinetic models of RNA secondary structure remains unclear but may stem from the use of potentially incomplete energetic models, incorrect mechanistic hypotheses, and from interference within the in vivo context of the bacterial cells. Regardless of the source of error, we sought to explore deep learning as a machine learning paradigm to develop models with higher predictive abilities than previously reported, with the hope of allowing useful computer-aided systems for the design of RNA synthetic biology tools.

Improved Prediction Using Sequence-Based Multilayer Perceptron Models

Figure 3C:
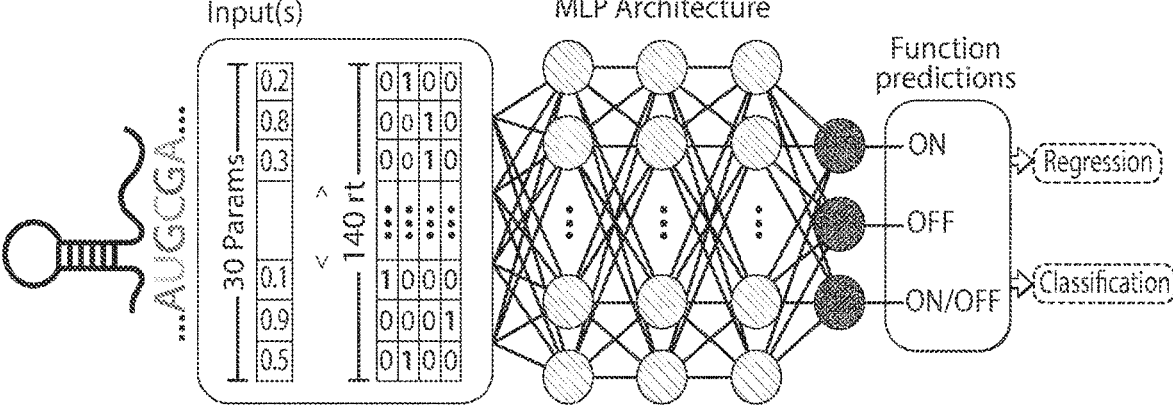
Figure 3D:
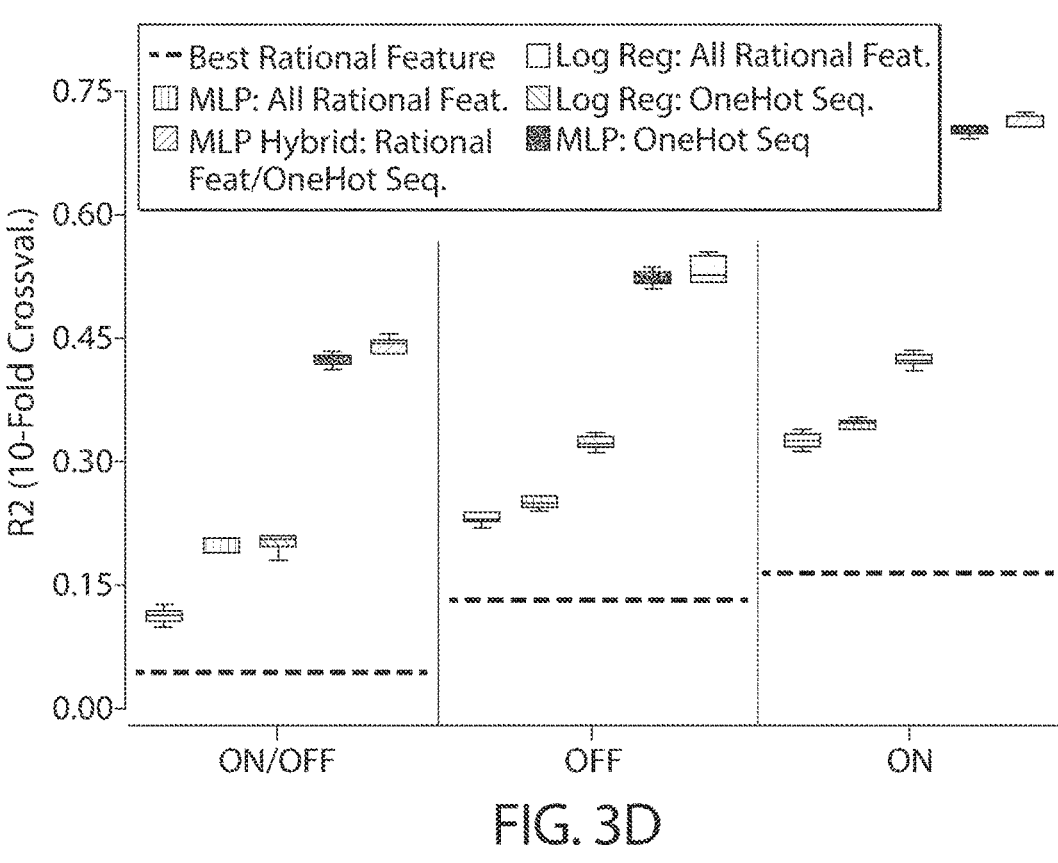
Figure 3E:
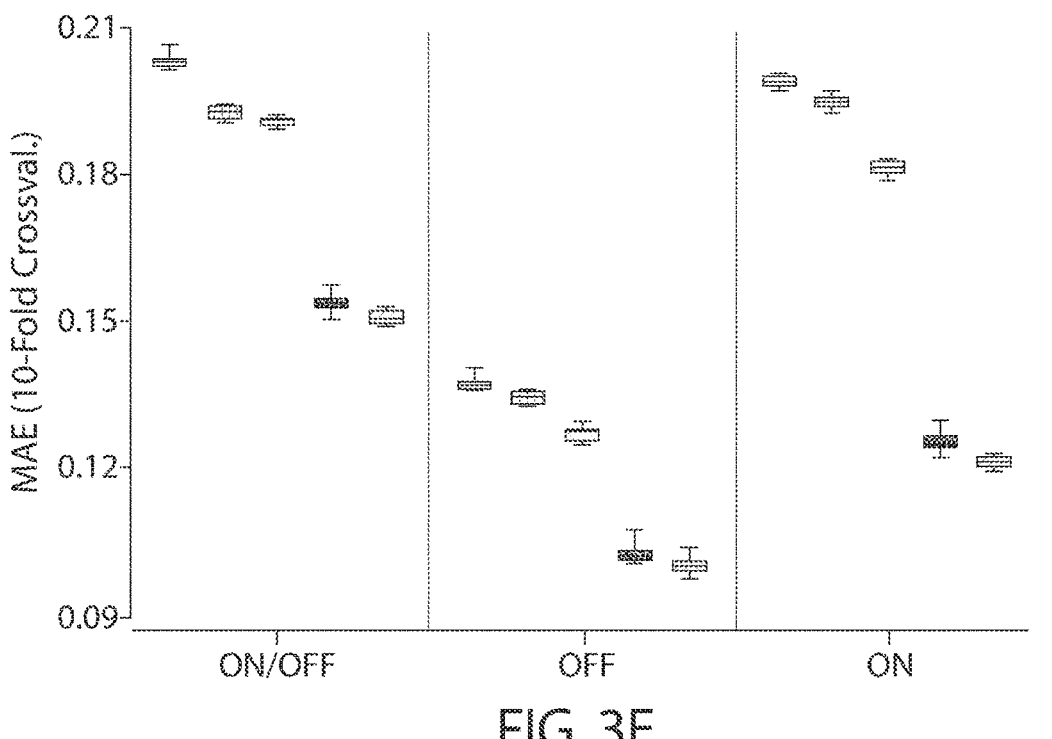
Figures 3F, 3G:
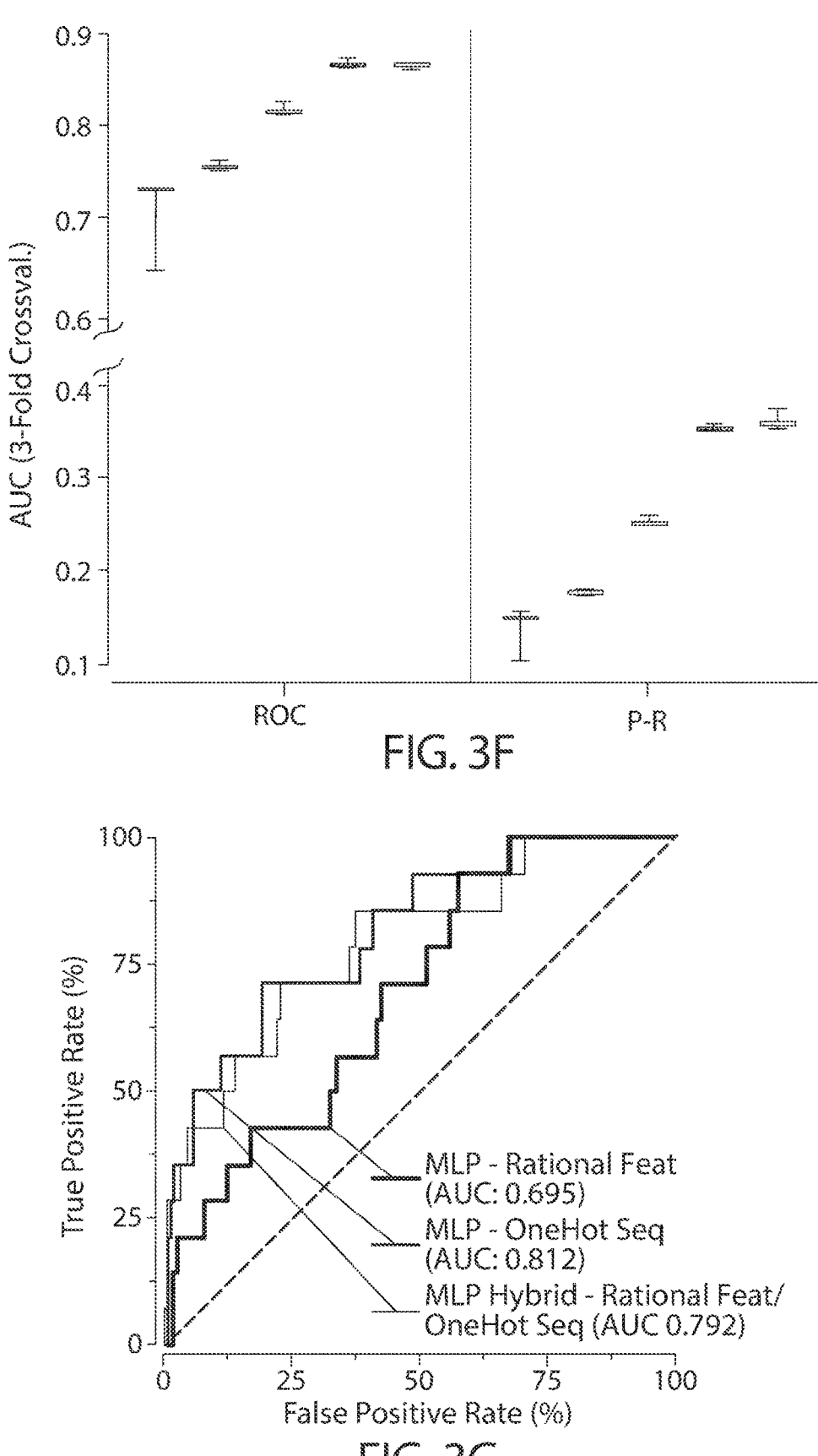

Given that simple regression models based on state-of-the-art RNA thermodynamic and kinetic calculations were ineffective at predicting toehold switch performance, we next tested the use of a type of feed-forward neural networks, also known as multilayer perceptron (MLP) models, as a baseline architecture for our investigation (FIG. 3C). We first trained a three-layer MLP model on our dataset with an input consisting of the 30 previously calculated thermodynamic rational features (see Methods section for further detail). When trained in regression-mode, this MLP model was able to deliver better predictions than any of the individual rational features or the RBS calculator based on $R^2$ and MAE ($R^2$: ON=0.35, OFF=0.25, ON/OFF=0.20) (FIGS. 3D, E). Similarly, when this model was trained for classification (ON/OFF: binarized at +/−0.7), as seen in FIG. 13, it achieved a 0.76 area under the receiver-operator curve (AUROC) and 0.18 area under the precision-recall curve (AUPRC), as seen in FIG. 3F. The MLP model modestly outperformed a logistic regressor trained on the same rational features (FIGS. 3D,E,F), suggesting that the MLP architecture was able to abstract higher-order patterns from these features as compared to simpler non-hierarchical models.

While these results already constitute an improvement compared to the current state-of-the-art analysis of RNA synthetic biology tools, we wondered whether the use of pre-computed rational features as network input led to information loss that could inherently limit the predictive power of these models. Considering that possibility, we trained an MLP model solely on one-hot encoded sequence representations of our toehold switches, eliminating potential bias introduced by a priori mechanistic modeling. We found that this sequence-based MLP delivered improved functional predictions based on $R^2$ and MAE ($R^2$: ON=0.70, OFF=0.53, ON/OFF=0.43) metrics (FIGS. 3D, E, 14). These values represent a doubling of $R^2$ performance as compared to the MLP trained on rational features and a ten-fold improvement in ON/OFF $R^2$ over the best rational feature used for previous linear models.

Similarly, when training for classification, our one-hot sequence MLP produced improved AUROCs and AUPRCs, reaching 0.87 and 0.36, respectively (FIG. 3F). This improvement in performance when training on sequence-only inputs compared to rational features suggests that significant information loss occurs when performing thermodynamic calculations on toehold switch sequences, a problem that may extend to other RNA synthetic biology tools in use today. Also, the sequence-only MLP model dramatically outperformed the logistic regressor model trained on the same one-hot sequence input (FIGS. 3D,E,F), further supporting the hypothesis that improved accuracy of our sequence-based MLP arises from learned hierarchical non-linear features extracted directly from RNA sequences.

A combined input concatenating both the rational features and the one-hot representation was also evaluated, giving a small, but significant improvement in regression mode ($\Delta R^2 \approx 0.025$ and $\Delta MAE \approx -0.0025$, $p < 0.05$ for all six comparisons, two-tailed t-test), but with no significant improvement for AUROC or AUPRC when in classification mode (FIGS. 3D,E,F). These results suggest that while the use of rational features may facilitate the abstraction of potentially relevant information of toehold switch function, the one-hot sequence-only MLP model can recover such information if given enough training data without a priori hypothesis-driven assumptions built into the model.

In order to validate the degree of biological generalization in our sequence-only MLP model, we withheld 23 viral genomes tiled in the toehold switch dataset during training and predicted their function resulting in a 0.82-0.98 AUROC range (average 0.87, FIG. 15). We then carried out an external validation on a previously published dataset of 168 characterized toehold switches (2) that our models had never seen before and that had been collected under different experimental conditions. Our MLP models achieved an AUROC of 0.70, 0.81, and 0.79, when trained on rational features, one-hot sequence, and hybrid inputs, respectively (FIG. 3G). The improved performance observed when training the models directly on nucleotide sequence rather than thermodynamic features, even for an external dataset, suggest a competent degree of biological generalization and supports the value of modeling RNA synthetic biology tools using deep learning and high-throughput datasets, removing current assumptions from mechanistic rational parameters.

Predictive Performance of Higher-Capacity Deep Learning Models

Having explored relatively simple deep learning architectures first, we next sought to determine whether training our dataset on higher-capacity convolutional neural networks (CNN) and long short-term memory (LSTM) recurrent neural networks could increase our predictive ability. CNN and LSTM models have been applied to a variety of biological datasets in recent years, and have been cited as being particularly adept at recognizing motifs and long-range interactions in nucleotide sequence data (10, 17-20, 34-38). We specifically evaluated a CNN trained on a one-hot sequence input, an LSTM trained on a one-hot sequence input, and a CNN applied to a two-dimensional (2D), one-hot complementarity map representation input (see Methods for complete descriptions of all models). Upon evaluating both the $R^2$ and MAE in regression mode and the AUROC and AUPRC in classification mode for these models (FIGS. 4A,B,C,D), we concluded that these neural network architectures did not lead to superior predictive models, as compared to the sequence-based, three-layer MLP described previously. We reasoned that, in these specific cases, increased model capacity led to under- or over-fitting, requiring additional training examples or improved fine-tuning to accelerate effective training.

Visualizing Learned RNA Secondary Structure Motifs with VIS4Map

One significant drawback of using deep learning approaches to predict biological function is the inherent difficulty in understanding learned patterns in a way that aids researchers in elucidating biological mechanisms underlying the model predictions. By contrast, mechanistic hypothesis-driven models can more directly inform which aspects of a biological theory best explain the observations. Various methods have been established to address this limitation, including alternative network architectures (39), and the use of saliency maps (40, 41), which reveal the regions of an input that deep learning models pay attention to when making predictions. While saliency maps have been previously used to visualize model attention in one-hot representations of sequence data (10, 17, 18, 20, 40), such implementations focus only on the primary sequence and have not been developed to identify secondary structure interactions, which are specially relevant in the operation of RNA synthetic biology elements. In the few cases where secondary structure has been investigated, input representations have been constrained to predetermined structures based on the predictions of thermodynamic models (37, 38), whose abstractions we have found cause significant information loss.

In order to better explain our deep learning model's predictions, we sought to visualize RNA secondary structures learned by our neural networks in a manner unconstrained by thermodynamic modeling. To achieve this, we chose to use a CNN trained on two-dimensional nucleotide complementarity map representations (FIG. 5A) to allow for attention pattern visualization in this secondary structure space. Each position in this complementarity map corresponds to the potential pair between two nucleotides, indicating its identity with a one-hot encoding (G-C, C-G, A-U, U-A, G-U, U-G, or an unproductive pair). We hypothesized that by training deep networks on such a representation of RNA sequences, it would be possible for generated saliency maps to reveal learned secondary structure features as visually intuitive diagonal features. Importantly, because the complementarity map is unconstrained by a priori hypotheses of RNA folding (similarly to our sequence-based MLP models), we anticipated this approach to be able to identify secondary structures that might be overlooked by commonly used thermodynamic and kinetic algorithms, such as NUPACK and Kinfold.

Figure 5A:
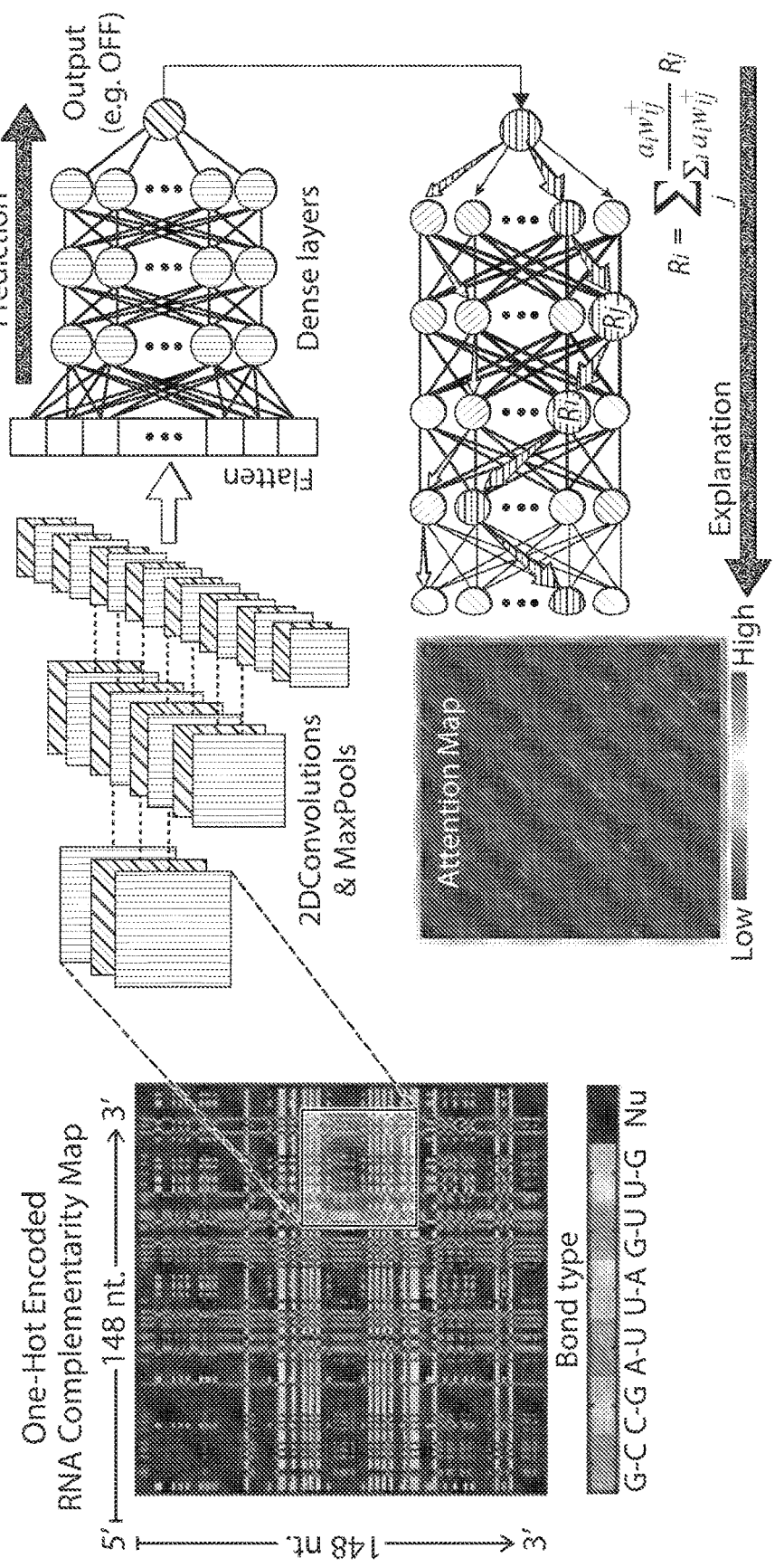
Figure 5B:
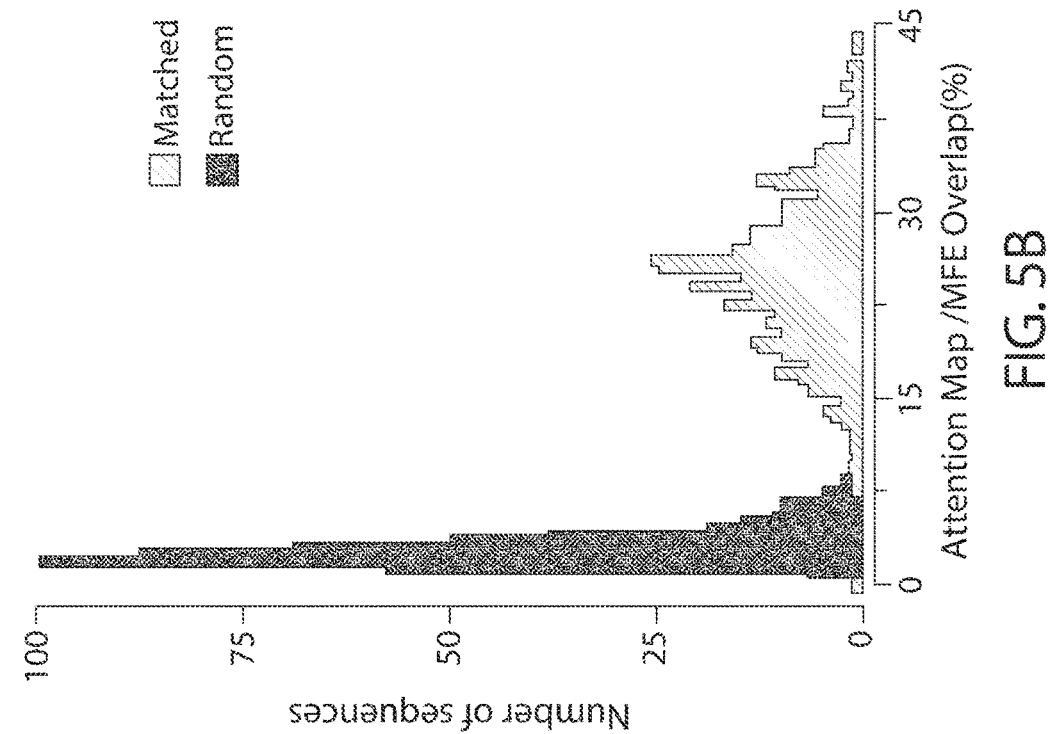
Figure 5C:
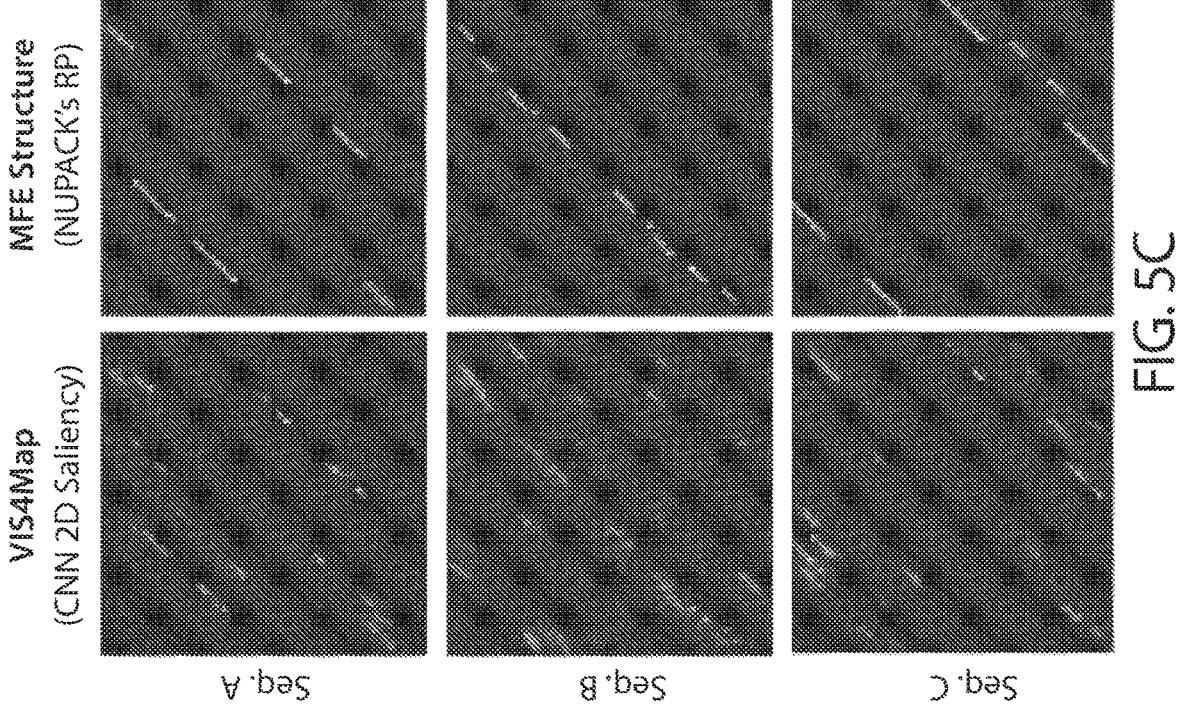

To validate the feasibility of our visualization approach, we first pre-trained a CNN to predict NUPACK MFE values from complementarity map representations of a randomly selected in silico RNA sequence dataset. Because MFE is directly determined by RNA secondary structure, we anticipated that a CNN undergoing this pre-training would likely pay attention to secondary structure features, a situation that was confirmed through visualization of individual attention maps (FIGS. 5B,C). Additionally, we found that the use of a complementarity map input improved the CNN's predictions of MFE from $R^2 = 0.6$ to $R^2 = 0.74$ compared with a one-hot sequence input (FIG. 16). Indeed, the saliency maps generated from a CNN trained on a complementarity map input contained primarily diagonal features that showed a statistically significant degree of agreement with the MFE structures from which NUPACK based its MFE calculations (FIGS. 5B, C, 16). Hence without prior knowledge of the algorithm or parameters NUPACK uses to calculate MFE, our CNN was able to learn similar abstractions as NUPACK, which we then used to intuitively visualize underlying relevant RNA secondary structures utilizing our complementarity map input representation. We named this approach for interpreting RNA deep learning models Visualizing Secondary Structure Saliency Maps or VIS4Map.

Figures 4A, 4B:
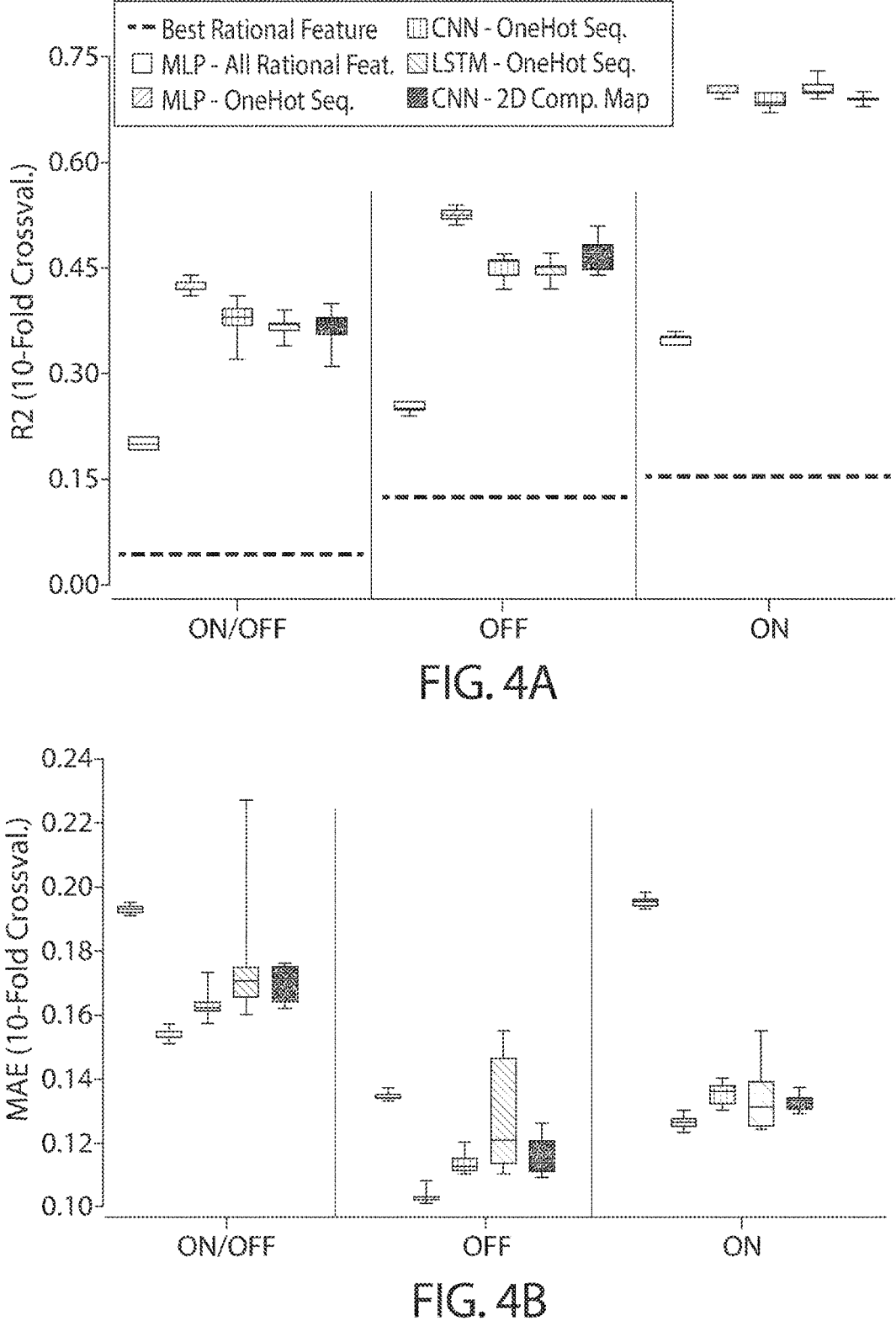
Figures 4C, 4D:
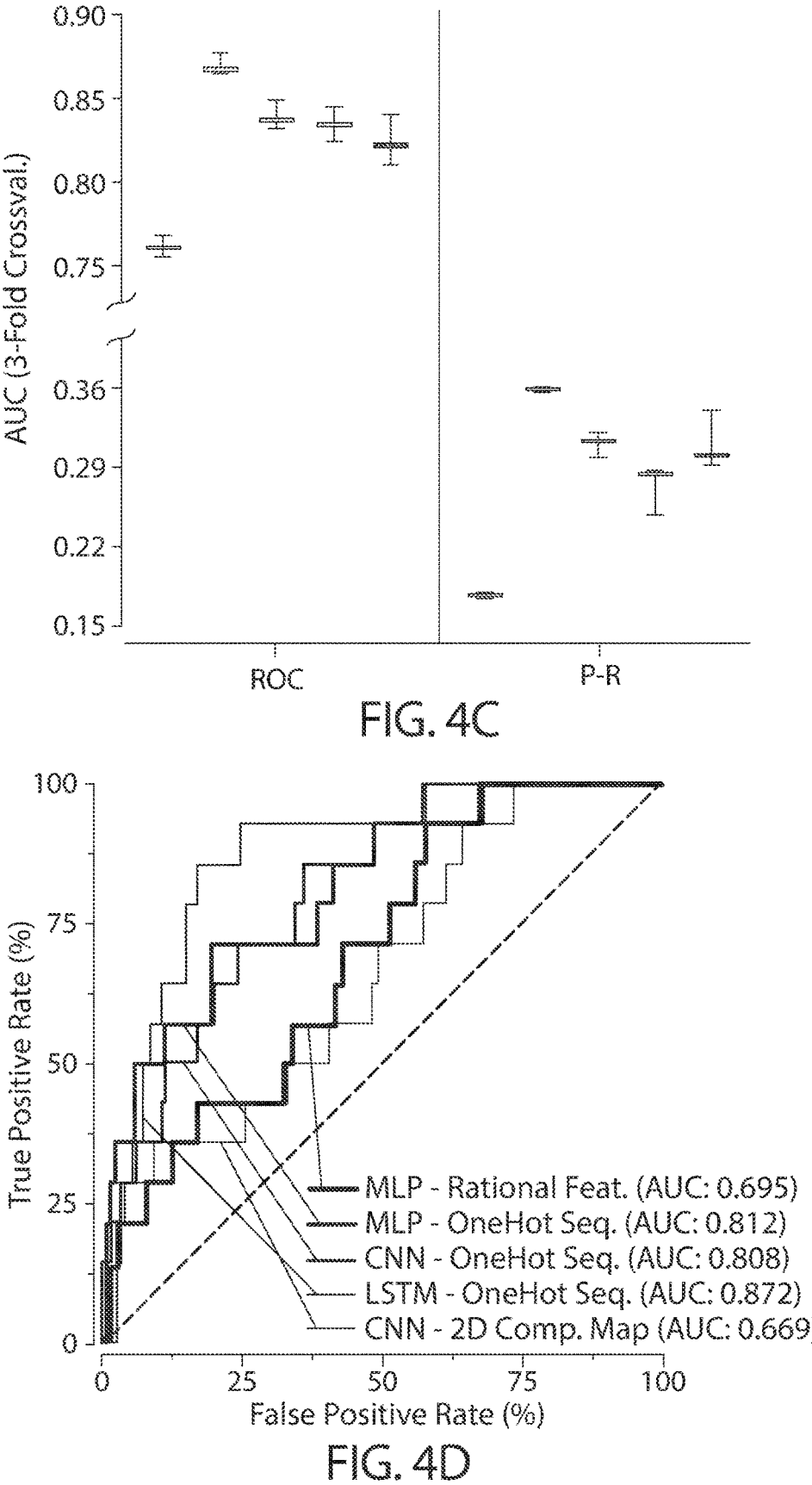
Figure 5D:
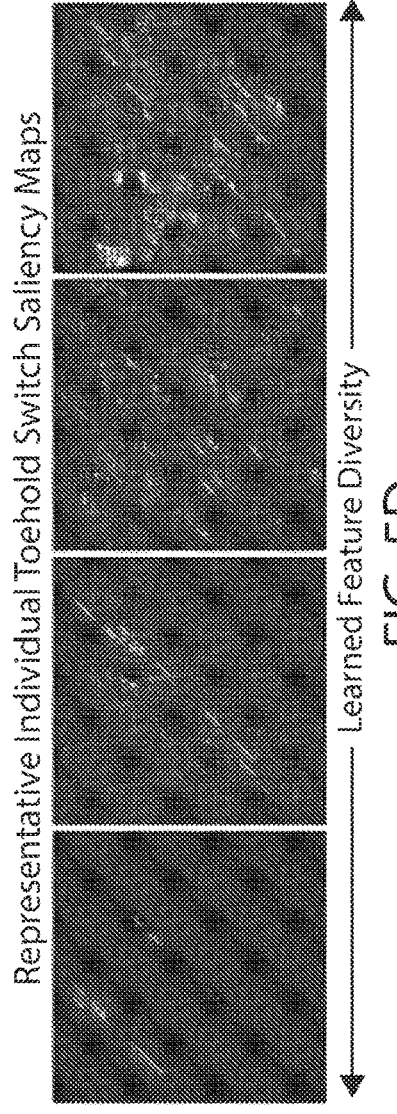
Figure 5E:
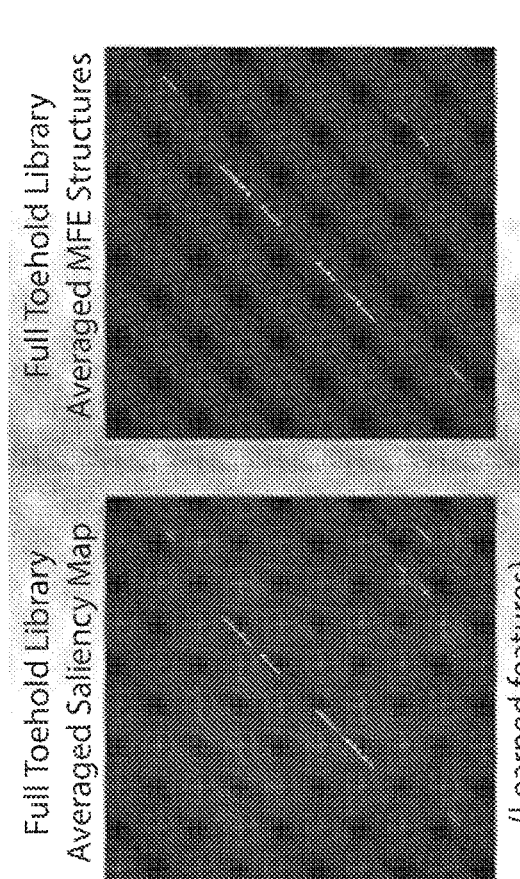
Figure 5F:
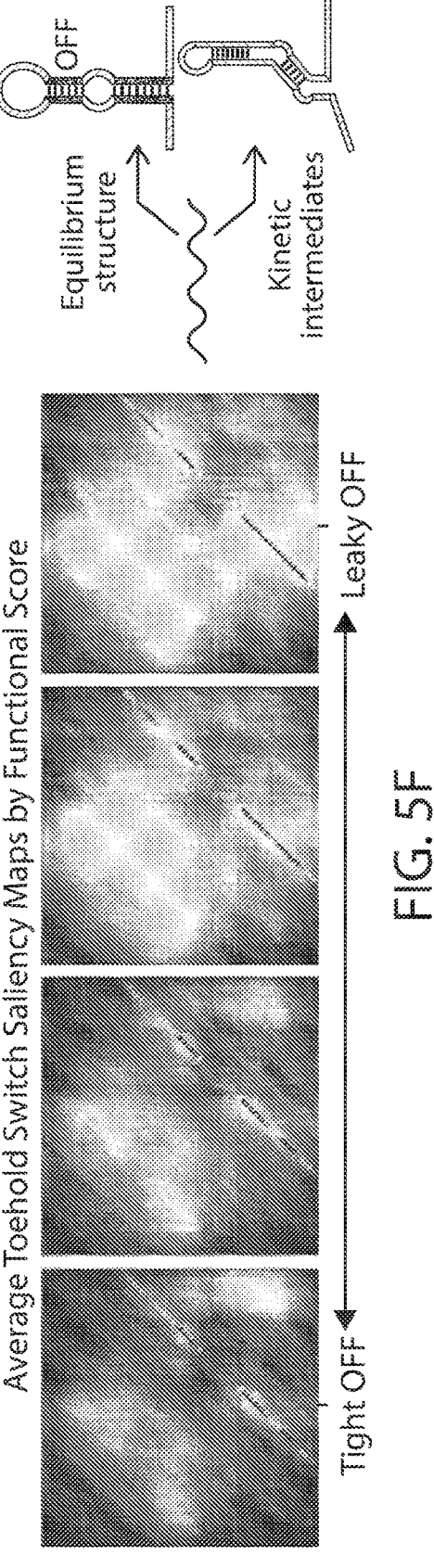

Encouraged by our CNN's ability to elucidate RNA secondary structure features directly from training data, we applied VIS4Map to our entire toehold switch dataset. When trained on a complementarity map representation of the switch OFF conformation (FIG. 5D) both in regression mode and classification mode, VIS4Map significantly outperformed an MLP trained on rational thermodynamic features; however, VIS4Map did not significantly outperform our MLP trained on one-hot inputs, similar to the case of our other higher capacity models (FIGS. 4A,B,C,D). Encouragingly, nonetheless, we found that saliency maps produced by this CNN model displayed clear diagonal secondary structure features (FIG. 5D). These structures appear to span from hybridization between the toehold and the ascending stem, to hybridization between the descending stem and the downstream linker. We confirmed the biological relevance of these features by averaging saliency maps and found that the shared structures corresponded to the designed on-target structure of the switch hairpin (FIG. 5E). We further analyzed learned features outside of the designed MFE structure by sorting saliency maps using the toehold switch OFF signal (FIGS. 5F and 17). We found that for leakier (high OFF) switches, the CNN identified a high degree of salient off-target secondary structures that could compete with the main hairpin stem and thereby exposed the RBS, whereas for tight (low OFF) switches the CNN identified fewer competing off-target secondary structures. In the context of general riboregulator behavior, these findings support the hypothesis that leaky expression from an RBS repressed by secondary structures can be caused by the misfolding of the repressive structure into less stable kinetic intermediate conformations (29, 32) (FIG. 5F, right).

The fact that VIS4Map was able to identify both equilibrium and kinetically stable RNA secondary structures indicates a remarkable ability to uncover biologically relevant information, which in this case supports currently postulated hypotheses on prokaryotic translation initiation. Importantly, the identified secondary structure features could not have been visualized using the one-hot sequence representation commonly associated with saliency maps (10, 17, 18, 20). These findings compound to the advantage of using sequence-only deep learning approaches for analyzing RNA synthetic biology tools. Outside of toehold switches and other synthetic RNA systems, we anticipate VIS4Map will be broadly useful for the discovery of previously unknown equilibrium or kinetically stable structures contributing to RNA biology, that are not predicted by current mechanistic RNA structure models.

Discussion

Here we presented a high-throughput DNA synthesis, sequencing, and deep learning pipeline for the design and analysis of a synthetic system in RNA biology. Having produced a toehold switch dataset ~100-fold larger than dynamic and kinetic features. Moreover, the validation of our deep learning models on an external previously characterized dataset, as well as the holdout prediction of every individual viral genome in our dataset, further demonstrated the robust biological generalization of our models.

As with most work in RNA synthetic biology, all previous attempts to improve toehold switch functionality have relied on the guidance of mechanistic thermodynamic modeling and low-throughput datasets (2-8, 15, 16). Too frequently, rational design rules fail to give meaningful predictions of function for RNA-based synthetic systems. The results presented here suggest that the biological processes underlying RNA biology may be more complex than current state-of-the-art analyses take into account and that high-throughput DNA synthesis, sequencing, and deep learning pipelines can be more effective for modeling said complexity. Combining improved predictions with enhanced understanding, our novel VIS4Map method further allowed us to visualize the equilibrium and kinetic secondary structure features that our deep learning models identified as important to the leakage of the switch OFF state. While secondary structures identified by NUPACK, Kinfold, and other rational mechanistic models are limited by predefined abstractions, which may cause significant information loss, our approach explored sequence space in an unrestricted manner and analyzed all possible RNA secondary structures. VIS4Map could prove useful for identifying complex secondary structure information that might otherwise be ignored by simplified physical energetic models of RNA folding.

The dataset reported here also represents an extensive repository of characterized toehold switches, which could be used to accelerate the development of future cell-free diagnostics (3, 4, 15, 16). These switches tile the entire genomes of 23 pathogenic viruses of high clinical importance, as well as tiling hundreds of human transcripts, including many that are differentially expressed in cancerous phenotypes (42, 43). The total cost of our flow-seq pipeline equates to ~$0.08 per measurement, suggesting that the benefits of high-throughput design and assaying of RNA synthetic biology tools could be made widely accessible. We hope that this work will encourage the use of high-throughput data collection for the training of deep learning systems, paired with more interpretable neural network architectures unrestricted by thermodynamic or kinetic secondary structure models for improved prediction and insight generation in RNA synthetic biology.

TABLE 1

| | Quality control thresholds. | | | | | | |
| | Quality Control Conditions | | | | Library Size | | |
| | OFF Count Threshold | ON Count Threshold | Upper Stdev. Cutoff | Lower Stdev. Cutoff | ON Variants | OFF Variants | ON/OFF Variants |
|---|---|---|---|---|---|---|---|
| QC1 | >=5 | >=5 | None | None | 126,620 | 180,552 | 110,931 |
| QC2 | >=10 | >=10 | None | None | 109,067 | 163,967 | 91,534 |
| QC3 | >=20 | >=40 | None | >0 | 77,040 | 90,264 | 43,044 |
| QC4 | >=60 | >=60 | 0.4> | >0.04 | 39,283 | 67,507 | 19,983 |
| QC5 | >=300 | >=300 | 0.4> | >0.04 | 6,187 | 12,551 | 1,137 | previously published as a model system for investigating synthetic RNA response elements (2-6, 15, 16), we demonstrated the benefits of using deep learning methods that directly analyze sequence rather than relying on calculations from mechanistic thermodynamic and kinetic models. This approach resulted in tenfold improvement in functional prediction $R^2$ over an ensemble of commonly used thermo- The conditions for inclusion in our five quality control groups (QC1-5) are shown above, including standard deviation cutoffs and library count thresholds. QC2 was ultimately chosen as the final condition for inclusion in our dataset, and all data used or shown in this manuscript is for QC2 unless otherwise stated. The size of each dataset is shown in the three rightmost columns.

TABLE 2

| Toehold switch sequences validated in cell-free format. |
| --- |

| | Corresponding Riboregulator SEQ ID NO # | Trigger Sequence | On | Off |
| --- | --- | --- | --- | --- |
| Low 1 | 52454 | CCGACACCTGTTTCATGGAACAATAAAAGA (SEQ ID NO: 244004) | 0.0153 | 0.0085 |
| Low 2 | 65651 | TGCTGTCTGTGAAACAGATAAATGGAAATA (SEQ ID NO: 244005) | 0.0176 | 0.0100 |
| Low 3 | 67027 | TCCCTTTCCCAGAAATAAACTTTTTTACCC (SEQ ID NO: 244006) | 0.0181 | 0.0136 |
| Low 4 | 235901 | TCACTGAGTCATTGCCATCTGCAGAATCAG (SEQ ID NO: 244007) | 0.0048 | 0.0134 |
| Low 5 | 81973 | TCCAAGACCCAAAGTTCTGGGAACTGGTGG (SEQ ID NO: 244008) | 0.0192 | 0.0156 |
| Low 6 | 45174 | TGGCAATTGTAGATATAACTTCTGGTAAAT (SEQ ID NO: 244009) | 0.0153 | 0.0183 |
| Low 7 | 74706 | ATCCAAATATAATGATGACCTATATGCCCT (SEQ ID NO: 244010) | 0.0158 | 0.0102 |
| Low 8 | 66097 | CCAATATGAGATCTGTAATGCTAACAGTTT (SEQ ID NO: 244011) | 0.0076 | 0.0146 |
| High 1 | 19367 | GTCATATAAAGGAAGAAGATAGGAGAAGAA (SEQ ID NO: 244012) | 0.9860 | 0.0031 |
| High 2 | 236638 | AGTTCACAAGAGATGGTTCATGGTGTTCCA (SEQ ID NO: 244013) | 0.9937 | 0.0132 |
| High 3 | 111698 | AAAGGTTAGCTTATGTTACATATCAAGATA (SEQ ID NO: 244014) | 0.9740 | 0.0016 |
| High 4 | 62866 | AATCACTGAAAATTGGAGTTAGGTATTGAC (SEQ ID NO: 244015) | 0.9747 | 0.0007 |
| High 5 | 40182 | GGTATGTTAAGTATGAGGCCTTATCCGTAC (SEQ ID NO: 244016) | 0.9895 | 0.0115 |
| High 6 | 9602 | TCAAGTTAGAGAAGGAAGTGGCTGAGACCC (SEQ ID NO: 244017) | 0.9856 | 0.0122 |
| High 7 | 43841 | TAAATCTATGAGAGATCAACGAAAAGGAAG (SEQ ID NO: 244018) | 0.9942 | 0.0150 |
| High 8 | 164989 | AAAGAAGAAATCATGCAAGAAAACAAAGGG (SEQ ID NO: 244019) | 0.9744 | 0.0007 |

Sequences of the individually cloned toehold switches for cell-free validation using PURExpress were selected from the QC3 threshold. Their trigger sequences and flow-seq assay performances are shown (see FIGS. 1F,9 for cell-free assay performance). All highly-functional switches have ON/OFF of 0.97 or greater, while all poorly-functional switches have ON/OFF of 0.04 or less.

TABLE 3

| K-mer search results. | | | | |
| --- | --- | --- | --- | --- |
| Motif | Counts in Foreground | Counts in Background | P-value | E-value |
| ON Triggers Low versus High Signal | | | | |
| UCUYU CU* | 349 | 0 | 7.10E-122 | 8.30E-117 |

TABLE 3-continued

| K-mer search results. | | | | |
| --- | --- | --- | --- | --- |
| Motif | Counts in Foreground | Counts in Background | P-value | E-value |
| GAUGG | 260 | 19 | 6.80E-63 | 7.90E-58 |
| AAAAA | 391 | 128 | 1.90E-42 | 2.10E-37 |
| CUCYU C* | 142 | 4 | 1.30E-39 | 1.40E-34 |
| UAUUA AC | 123 | 0 | 1.70E-39 | 1.90E-34 |
| UCUCA C* | 26 | 2 | 4.10E-37 | 4.50E-32 |
| GAGUC GU | 100 | 0 | 5.80E-32 | 6.30E-27 |

TABLE 3-continued

K-mer search results.

| Motif | Counts in Foreground | Counts in Background | P-value | E-value |
|---|---|---|---|---|
| GUUUU AUC | 100 | 2 | 8.50E-29 | 9.10E-24 |
| | | High versus Low Signal | | |
| ANSA | 785 | 427 | 6.00E-62 | 1.00E-56 |
| AWUB | 644 | 359 | 9.50E-38 | 7.80E-33 |
| UAYR | 355 | 163 | 3.90E-23 | 1.70E-18 |
| GVRA | 270 | 128 | 8.20E-16 | 2.50E-11 |
| ACK | 344 | 224 | 1.60E-09 | 3.80E-05 |
| AUAA | 104 | 47 | 8.30E-07 | 1.40E-02 |
| | OFF Triggers Low versus High Signal | | | |
| CNG | 762 | 503 | 8.40E-34 | 1.50E-28 |
| GRS | 510 | 342 | 1.90E-14 | 1.80E-09 |
| CCUH | 218 | 132 | 2.60E-07 | 1.60E-02 |
| | | High versus Low Signal | | |
| AWWWU | 591 | 346 | 2.10E-28 | 3.60E-23 |
| WUAW | 472 | 333 | 1.40E-10 | 1.60E-05 |
| AAAAR A | 67 | 22 | 5.60E-07 | 4.30E-02 |

K-mer motifs searched with DREME using the trigger RNA sequences of the highest and lowest performing 1000 switches sorted by either ON or OFF signal. For this search, QC3 dataset was selected. * Denotes potential anti-SD pyrimidine-rich sequences.

TABLE 4

Rational feature sub-sequences.

| Rational Feature Sub-sequence Name | Sequence Region | Brief Description |
|---|---|---|
| SwitchOFF | 30-108 | Toehold switch off conformation |
| SwitchOFF-GFP | 30-144 | Off conformation with added GFP sequence |
| SwitchOFF-NoTo | 62-144 | Off conformation with toehold removed |
| SwitchON | 0-108 | Toehold switch on conformation |
| SwitchON-GFP | 0-144 | On conformation with added GFP sequence |
| Trigger | 0-29 | Trigger sequence alone |
| ToeholdOFF | 30-62 | Toehold region of switch including link1 |
| ToeholdON | 0-62 | Toehold region only hybridized to trigger |
| Stem | 62-108 | Stem only of toehold switch |
| AscendingStem | 62-100 | Ascending arm of the switch stem |
| DescendingStem | 80-108 | Descending arm of the switch stem |
| StemTop | 74-97 | Top half of the stem from start codon up |
| RBS-Linker | 80-134 | Region from RBS loop2 to linker |
| RBS-GFP | 80-144 | RBS-Linker with added GFP sequence |

| [-3, -1] | [0, 29] | [30, 49] | [50, 79] | [80, 90] | [91, 96] | [97, 99] | [100, 108] | [109, 134] | [135, 144] |
|---|---|---|---|---|---|---|---|---|---|
| GGG | trigger | loop1 | switch | loop2 | stem1 | AUG | stem2 | linker | post-linker |

The sub-sequences from which the thirty rational features used as MLP input were calculated using ViennaRNA are shown here in the upper panel. In the lower panel, we show the full un-truncated toehold switch sequence framework from which the sub-sequences in the top table were selected.

TABLE 5

List of SEQ ID NOs: 1-244,000 denoting viral or transcription factor specificity

| Virus/Source Gene | SEQ ID NOs: 1-159175 |
|---|---|
| astrovirus | SEQ ID NO: 1-1298 |
| cardiovirus | SEQ ID NO: 1299-2885 |
| chikungunya | SEQ ID NO: 2886-5245 |
| cosavirus | SEQ ID NO: 5246-6682 |
| coxsackie | SEQ ID NO: 6683-8156 |
| dengue | SEQ ID NO: 8157-10298 |
| ebola | SEQ ID NO: 10299-14080 |
| hantavirus | SEQ ID NO: 14081-14798 |
| human immunodeficiency | SEQ ID NO: 14799-16864 |
| human parvo | SEQ ID NO: 16865-17978 |
| human rhino | SEQ ID NO: 17979-19403 |
| influenza: h1n1 | SEQ ID NO: 19404-19603 |
| influenza: h3n2 | SEQ ID NO: 19604-20044 |
| lassa | SEQ ID NO: 20045-20719 |
| leishmania | SEQ ID NO: 20720-21752 |
| marburg | SEQ ID NO: 21753-25569 |
| papilloma | SEQ ID NO: 25570-27118 |
| poliovirus | SEQ ID NO: 27119-28601 |
| rabies | SEQ ID NO: 28602-30976 |
| random_sequences | SEQ ID NO: 30977-41790 |
| smallpox | SEQ ID NO: 41791-78900 |
| west nile | SEQ ID NO: 78901-81100 |
| yellow fever | SEQ ID NO: 81101-83267 |
| zika | SEQ ID NO: 83268-85423 |
| human_AC009336.2 | SEQ ID NO: 85424-85465 |
| human_AC012531.2 | SEQ ID NO: 85466-85501 |
| human_AC097634.4 | SEQ ID NO: 85502-85702 |
| human_ACTB | SEQ ID NO: 85703-85812 |
| human_ACTL6A | SEQ ID NO: 85813-85926 |
| human_ACTN4 | SEQ ID NO: 85927-86197 |
| human_AEBP1 | SEQ ID NO: 86198-86542 |
| human_AEBP2 | SEQ ID NO: 86543-86695 |
| human_AGO1 | SEQ ID NO: 86696-86950 |
| human_AGO2 | SEQ ID NO: 86951-87206 |
| human_AHR | SEQ ID NO: 87207-87458 |
| human_AIRE | SEQ ID NO: 87459-87619 |

TABLE 5-continued

List of SEQ ID NOs: 1-244,000 denoting viral
or transcription factor specificity

| Virus/Source Gene | |
|---|---|
| human_AKNA | SEQ ID NO: 87620-87887 |
| human_AL121581.1 | SEQ ID NO: 87888-88134 |
| human_ALX1 | SEQ ID NO: 88135-88230 |
| human_ALX4 | SEQ ID NO: 88231-88351 |
| human_ANHX | SEQ ID NO: 88352-88463 |
| human_AR | SEQ ID NO: 88464-88737 |
| human_ARHGAP35 | SEQ ID NO: 88738-89185 |
| human_ARID3A | SEQ ID NO: 89186-89361 |
| human_ARID3B | SEQ ID NO: 89362-89527 |
| human_ARID3C | SEQ ID NO: 89528-89648 |
| human_ARID4A | SEQ ID NO: 89649-90002 |
| human_ARID4B | SEQ ID NO: 90003-90393 |
| human_ARID5A | SEQ ID NO: 90394-90569 |
| human_ARID5B | SEQ ID NO: 90570-90923 |
| human_ARNT | SEQ ID NO: 90924-91157 |
| human_ARNT2 | SEQ ID NO: 91158-91370 |
| human_ARNTL | SEQ ID NO: 91371-91556 |
| human_ARNTL2 | SEQ ID NO: 91557-91730 |
| human_ARRB1 | SEQ ID NO: 91731-91851 |
| human_ARX | SEQ ID NO: 91852-92017 |
| human_ASCL1 | SEQ ID NO: 92018-92086 |
| human_ASCL2 | SEQ ID NO: 92087-92142 |
| human_ASCL3 | SEQ ID NO: 92143-92194 |
| human_ASCL4 | SEQ ID NO: 92195-92244 |
| human_ASCL5 | SEQ ID NO: 92245-92304 |
| human_ASH2L | SEQ ID NO: 92305-92490 |
| human_ATF1 | SEQ ID NO: 92491-92569 |
| human_ATF2 | SEQ ID NO: 92570-92718 |
| human_ATF3 | SEQ ID NO: 92719-92770 |
| human_ATF4 | SEQ ID NO: 92771-92873 |
| human_ATF5 | SEQ ID NO: 92874-92955 |
| human_ATF6 | SEQ ID NO: 92956-93154 |
| human_ATF6B | SEQ ID NO: 93155-93363 |
| human_ATMIN | SEQ ID NO: 93364-93608 |
| human_ATOH1 | SEQ ID NO: 93609-93712 |
| human_ATOH8 | SEQ ID NO: 93713-93806 |
| human_ATXN3 | SEQ ID NO: 93807-93912 |
| human_BACH1 | SEQ ID NO: 93913-94131 |
| human_BACH2 | SEQ ID NO: 94132-94381 |
| human_BARHL1 | SEQ ID NO: 94382-94477 |
| human_BARHL2 | SEQ ID NO: 94478-94591 |
| human_BARX1 | SEQ ID NO: 94592-94665 |
| human_BARX2 | SEQ ID NO: 94666-94747 |
| human_BASP1 | SEQ ID NO: 94748-94813 |
| human_BATF | SEQ ID NO: 94814-94848 |
| human_BATF2 | SEQ ID NO: 94849-94928 |
| human_BATF3 | SEQ ID NO: 94929-94964 |
| human_BAZ2A | SEQ ID NO: 94965-95533 |
| human_BCL11A | SEQ ID NO: 95534-95771 |
| human_BCL11B | SEQ ID NO: 95772-96037 |
| human_BCL6 | SEQ ID NO: 96038-96247 |
| human_BCL6B | SEQ ID NO: 96248-96389 |
| human_BCOR | SEQ ID NO: 96390-96903 |
| human_BHLHA15 | SEQ ID NO: 96904-96958 |
| human_BHLHE40 | SEQ ID NO: 96959-97079 |
| human_BHLHE41 | SEQ ID NO: 97080-97221 |
| human_BORCS8-MEF2B | SEQ ID NO: 97222-97328 |
| human_BRCA1 | SEQ ID NO: 97329-97542 |
| human_BRD7 | SEQ ID NO: 97543-97735 |
| human_BRF2 | SEQ ID NO: 97736-97859 |
| human_CALCOCO1 | SEQ ID NO: 97860-98064 |
| human_CARF | SEQ ID NO: 98065-98279 |
| human_CARM1 | SEQ ID NO: 98280-98459 |
| human_CBX4 | SEQ ID NO: 98460-98625 |
| human_CC2D1A | SEQ ID NO: 98626-98908 |
| human_CC2D1B | SEQ ID NO: 98909-99163 |
| human_CCAR1 | SEQ ID NO: 99164-99506 |
| human_CCNT1 | SEQ ID NO: 99507-99722 |
| human_CDC5L | SEQ ID NO: 99723-99960 |
| human_CDK12 | SEQ ID NO: 99961-100405 |
| human_CDK13 | SEQ ID NO: 100406-100856 |
| human_CDK5RAP2 | SEQ ID NO: 100857-101422 |
| human_CDK9 | SEQ ID NO: 101423-101531 |
| human_CDX1 | SEQ ID NO: 101532-101608 |
| human_CDX2 | SEQ ID NO: 101609-101700 |

TABLE 5-continued

List of SEQ ID NOs: 1-244,000 denoting viral
or transcription factor specificity

| Virus/Source Gene | |
|---|---|
| human_CDX4 | SEQ ID NO: 101701-101783 |
| human_CEBPA | SEQ ID NO: 101784-101888 |
| human_CEBPB | SEQ ID NO: 101889-101989 |
| human_CEBPD | SEQ ID NO: 101990-102068 |
| human_CEBPE | SEQ ID NO: 102069-102150 |
| human_CEBPG | SEQ ID NO: 102151-102193 |
| human_CEBPZ | SEQ ID NO: 102194-102507 |
| human_CGGBP1 | SEQ ID NO: 102508-102555 |
| human_CHD2 | SEQ ID NO: 102556-102703 |
| human_CHD4 | SEQ ID NO: 102704-103283 |
| human_CHD7 | SEQ ID NO: 103284-104180 |
| human_CIART | SEQ ID NO: 104181-104293 |
| human_CIITA | SEQ ID NO: 104294-104455 |
| human_CITED1 | SEQ ID NO: 104456-104511 |
| human_CLOCK | SEQ ID NO: 104512-104763 |
| human_CNBP | SEQ ID NO: 104764-104814 |
| human_CREB1 | SEQ ID NO: 104815-104910 |
| human_CREB3 | SEQ ID NO: 104911-105019 |
| human_CREB3L1 | SEQ ID NO: 105020-105173 |
| human_CREB3L2 | SEQ ID NO: 105174-105327 |
| human_CREB3L3 | SEQ ID NO: 105328-105463 |
| human_CREB3L4 | SEQ ID NO: 105464-105579 |
| human_CREBBP | SEQ ID NO: 105580-106309 |
| human_CREBRF | SEQ ID NO: 106310-106499 |
| human_CREM | SEQ ID NO: 106500-106587 |
| human_CRX | SEQ ID NO: 106588-106675 |
| human_CRY1 | SEQ ID NO: 106676-106849 |
| human_CRY2 | SEQ ID NO: 106850-107006 |
| human_CT476828.9 | SEQ ID NO: 107007-107131 |
| human_CTCF | SEQ ID NO: 107132-107347 |
| human_CTCFL | SEQ ID NO: 107348-107544 |
| human_CUX1 | SEQ ID NO: 107545-107993 |
| human_CUX2 | SEQ ID NO: 107994-108437 |
| human_CXXC1 | SEQ ID NO: 108438-108633 |
| human_DACH1 | SEQ ID NO: 108634-108843 |
| human_DBP | SEQ ID NO: 108844-108938 |
| human_DDIT3 | SEQ ID NO: 108939-108987 |
| human_DDN | SEQ ID NO: 108988-109198 |
| human_DEAF1 | SEQ ID NO: 109199-109365 |
| human_DHX36 | SEQ ID NO: 109366-109657 |
| human_DHX9 | SEQ ID NO: 109658-110036 |
| human_DLX1 | SEQ ID NO: 110037-110110 |
| human_DLX2 | SEQ ID NO: 110111-110206 |
| human_DLX4 | SEQ ID NO: 110207-110276 |
| human_DLX5 | SEQ ID NO: 110277-110361 |
| human_DMBX1 | SEQ ID NO: 110362-110472 |
| human_DMRT1 | SEQ ID NO: 110473-110582 |
| human_DMRT2 | SEQ ID NO: 110583-110748 |
| human_DNMT3A | SEQ ID NO: 110749-111019 |
| human_DPF2 | SEQ ID NO: 111020-111079 |
| human_DR1 | SEQ ID NO: 111080-111130 |
| human_DRAP1 | SEQ ID NO: 111131-111189 |
| human_DUX4 | SEQ ID NO: 111190-111314 |
| human_E2F1 | SEQ ID NO: 111315-111443 |
| human_E2F2 | SEQ ID NO: 111444-111572 |
| human_E2F3 | SEQ ID NO: 111573-111709 |
| human_E2F4 | SEQ ID NO: 111710-111831 |
| human_E2F6 | SEQ ID NO: 111832-111904 |
| human_E2F7 | SEQ ID NO: 111905-112175 |
| human_E2F8 | SEQ ID NO: 112176-112433 |
| human_E4F1 | SEQ ID NO: 112434-112666 |
| human_EAF2 | SEQ ID NO: 112667-112742 |
| human_EBF2 | SEQ ID NO: 112743-112912 |
| human_EBF3 | SEQ ID NO: 112913-113075 |
| human_EBF4 | SEQ ID NO: 113076-113252 |
| human_EED | SEQ ID NO: 113253-113390 |
| human_EGR1 | SEQ ID NO: 113391-113551 |
| human_EGR2 | SEQ ID NO: 113552-113692 |
| human_EGR3 | SEQ ID NO: 113693-113806 |
| human_EGR4 | SEQ ID NO: 113807-113981 |
| human_EHF | SEQ ID NO: 113982-114069 |
| human_EHMT2 | SEQ ID NO: 114070-114437 |
| human_ELF1 | SEQ ID NO: 114438-114621 |
| human_ELF3 | SEQ ID NO: 114622-114730 |
| human_ELF4 | SEQ ID NO: 114731-114927 |

TABLE 5-continued

List of SEQ ID NOs: 1-244,000 denoting viral
or transcription factor specificity

| Virus/Source Gene | |
| --- | --- |
| human_ELF5 | SEQ ID NO: 114928-115004 |
| human_ELK1 | SEQ ID NO: 115005-115130 |
| human_ELK3 | SEQ ID NO: 115131-115250 |
| human_ELK4 | SEQ ID NO: 115251-115369 |
| human_ELL3 | SEQ ID NO: 115370-115486 |
| human_ELMSAN1 | SEQ ID NO: 115487-115797 |
| human_EN1 | SEQ ID NO: 115798-115912 |
| human_ENO1 | SEQ ID NO: 115913-116040 |
| human_EOMES | SEQ ID NO: 116041-116249 |
| human_EP300 | SEQ ID NO: 116250-116971 |
| human_ERBB4 | SEQ ID NO: 116972-117361 |
| human_ERG | SEQ ID NO: 117362-117503 |
| human_ESR1 | SEQ ID NO: 117504-117679 |
| human_ESR2 | SEQ ID NO: 117680-117809 |
| human_ESRRA | SEQ ID NO: 117810-117934 |
| human_ESRRB | SEQ ID NO: 117935-118084 |
| human_ESRRG | SEQ ID NO: 118085-118223 |
| human_ESX1 | SEQ ID NO: 118224-118343 |
| human_ETS1 | SEQ ID NO: 118344-118473 |
| human_ETS2 | SEQ ID NO: 118474-118612 |
| human_ETV1 | SEQ ID NO: 118613-118748 |
| human_ETV2 | SEQ ID NO: 118749-118848 |
| human_ETV3 | SEQ ID NO: 118849-118999 |
| human_ETV4 | SEQ ID NO: 119000-119142 |
| human_ETV5 | SEQ ID NO: 119143-119293 |
| human_ETV6 | SEQ ID NO: 119294-119426 |
| human_ETV7 | SEQ ID NO: 119427-119526 |
| human_EZH2 | SEQ ID NO: 119527-119749 |
| human_FERD3L | SEQ ID NO: 119750-119797 |
| human_FEZF1 | SEQ ID NO: 119798-119937 |
| human_FEZF2 | SEQ ID NO: 119938-120073 |
| human_FIGLA | SEQ ID NO: 120074-120137 |
| human_FLI1 | SEQ ID NO: 120138-120270 |
| human_FOS | SEQ ID NO: 120271-120382 |
| human_FOSB | SEQ ID NO: 120383-120481 |
| human_FOSL1 | SEQ ID NO: 120482-120560 |
| human_FOSL2 | SEQ ID NO: 120561-120656 |
| human_FOXA1 | SEQ ID NO: 120657-120795 |
| human_FOXA2 | SEQ ID NO: 120796-120930 |
| human_FOXA3 | SEQ ID NO: 120931-121033 |
| human_FOXC1 | SEQ ID NO: 121034-121197 |
| human_FOXC2 | SEQ ID NO: 121198-121345 |
| human_FOXD1 | SEQ ID NO: 121346-121482 |
| human_FOXD3 | SEQ ID NO: 121483-121623 |
| human_FOXF1 | SEQ ID NO: 121624-121735 |
| human_FOXF2 | SEQ ID NO: 121736-121866 |
| human_FOXH1 | SEQ ID NO: 121867-121973 |
| human_FOXI1 | SEQ ID NO: 121974-122084 |
| human_FOXJ1 | SEQ ID NO: 122085-122208 |
| human_FOXJ2 | SEQ ID NO: 122209-122378 |
| human_FOXK1 | SEQ ID NO: 122379-122596 |
| human_FOXK2 | SEQ ID NO: 122597-122792 |
| human_FOXL2 | SEQ ID NO: 122793-122903 |
| human_FOXM1 | SEQ ID NO: 122904-123141 |
| human_FOXN4 | SEQ ID NO: 123142-123294 |
| human_FOXO3 | SEQ ID NO: 123295-123494 |
| human_FOXP2 | SEQ ID NO: 123495-123714 |
| human_FOXP3 | SEQ ID NO: 123715-123841 |
| human_FOXQ1 | SEQ ID NO: 123842-123960 |
| human_FOXS1 | SEQ ID NO: 123961-124057 |
| human_FUBP3 | SEQ ID NO: 124058-124226 |
| human_GABPA | SEQ ID NO: 124227-124360 |
| human_GABPB1 | SEQ ID NO: 124361-124476 |
| human_GABPB2 | SEQ ID NO: 124477-124608 |
| human_GADD45A | SEQ ID NO: 124609-124655 |
| human_GATA1 | SEQ ID NO: 124656-124777 |
| human_GATA2 | SEQ ID NO: 124778-124919 |
| human_GATA3 | SEQ ID NO: 124920-125050 |
| human_GATA4 | SEQ ID NO: 125051-125180 |
| human_GATA5 | SEQ ID NO: 125181-125297 |
| human_GATA6 | SEQ ID NO: 125298-125473 |
| human_GATAD2B | SEQ ID NO: 125474-125649 |
| human_GBX2 | SEQ ID NO: 125650-125751 |
| human_GCFC2 | SEQ ID NO: 125752-125983 |
| human_GCM1 | SEQ ID NO: 125984-126112 |

TABLE 5-continued

List of SEQ ID NOs: 1-244,000 denoting viral
or transcription factor specificity

| Virus/Source Gene | |
| --- | --- |
| human_GFI1 | SEQ ID NO: 126113-126236 |
| human_GLI1 | SEQ ID NO: 126237-126566 |
| human_GLI2 | SEQ ID NO: 126567-127040 |
| human_GLI3 | SEQ ID NO: 127041-127512 |
| human_GLIS1 | SEQ ID NO: 127513-127696 |
| human_GLIS2 | SEQ ID NO: 127697-127851 |
| human_GLMP | SEQ ID NO: 127852-127971 |
| human_GMEB1 | SEQ ID NO: 127972-128141 |
| human_GMEB2 | SEQ ID NO: 128142-128298 |
| human_GRHL1 | SEQ ID NO: 128299-128481 |
| human_GRHL2 | SEQ ID NO: 128482-128666 |
| human_GSC | SEQ ID NO: 128667-128741 |
| human_GSX1 | SEQ ID NO: 128742-128818 |
| human_GTF2B | SEQ ID NO: 128819-128911 |
| human_GTF3C1 | SEQ ID NO: 128912-129542 |
| human_GZF1 | SEQ ID NO: 129543-129753 |
| human_H2AFY | SEQ ID NO: 129754-129862 |
| human_H2AFY2 | SEQ ID NO: 129863-129971 |
| human_H2AFZ | SEQ ID NO: 129972-130007 |
| human_H3F3A | SEQ ID NO: 130008-130046 |
| human_H3F3B | SEQ ID NO: 130047-130085 |
| human_HAND1 | SEQ ID NO: 130086-130147 |
| human_HAND2 | SEQ ID NO: 130148-130210 |
| human_HDAC1 | SEQ ID NO: 130211-130352 |
| human_HDAC2 | SEQ ID NO: 130353-130487 |
| human_HDAC4 | SEQ ID NO: 130488-130810 |
| human_HDAC5 | SEQ ID NO: 130811-131145 |
| human_HDAC6 | SEQ ID NO: 131146-131507 |
| human_HELT | SEQ ID NO: 131508-131577 |
| human_HES1 | SEQ ID NO: 131578-131659 |
| human_HES2 | SEQ ID NO: 131660-131709 |
| human_HES3 | SEQ ID NO: 131710-131763 |
| human_HES4 | SEQ ID NO: 131764-131827 |
| human_HES5 | SEQ ID NO: 131828-131875 |
| human_HES6 | SEQ ID NO: 131876-131940 |
| human_HES7 | SEQ ID NO: 131941-132005 |
| human_HESX1 | SEQ ID NO: 132006-132058 |
| human_HEY1 | SEQ ID NO: 132059-132148 |
| human_HEY2 | SEQ ID NO: 132149-132247 |
| human_HEYL | SEQ ID NO: 132248-132343 |
| human_HHEX | SEQ ID NO: 132344-132422 |
| human_HIC2 | SEQ ID NO: 132423-132604 |
| human_HIF1A | SEQ ID NO: 132605-132857 |
| human_HINFP | SEQ ID NO: 132858-133010 |
| human_HIVEP1 | SEQ ID NO: 133011-133823 |
| human_HLF | SEQ ID NO: 133824-133909 |
| human_HLTF | SEQ ID NO: 133910-134210 |
| human_HMGA1 | SEQ ID NO: 134211-134237 |
| human_HMGA2 | SEQ ID NO: 134238-134267 |
| human_HMGB1 | SEQ ID NO: 134268-134329 |
| human_HMGB2 | SEQ ID NO: 134330-134390 |
| human_HMX1 | SEQ ID NO: 134391-134492 |
| human_HMX3 | SEQ ID NO: 134493-134597 |
| human_HNF1A | SEQ ID NO: 134598-134678 |
| human_HNF1B | SEQ ID NO: 134679-134843 |
| human_HNF4A | SEQ ID NO: 134844-134976 |
| human_HNF4G | SEQ ID NO: 134977-135096 |
| human_HNRNPC | SEQ ID NO: 135097-135186 |
| human_HNRNPK | SEQ ID NO: 135187-135323 |
| human_HNRNPL | SEQ ID NO: 135324-135498 |
| human_HNRNPU | SEQ ID NO: 135499-135743 |
| human_HOXA10 | SEQ ID NO: 135744-135864 |
| human_HOXA2 | SEQ ID NO: 135865-135975 |
| human_HOXA3 | SEQ ID NO: 135976-136106 |
| human_HOXA4 | SEQ ID NO: 136107-136200 |
| human_HOXA5 | SEQ ID NO: 136201-136279 |
| human_HOXA6 | SEQ ID NO: 136280-136347 |
| human_HOXA7 | SEQ ID NO: 136348-136414 |
| human_HOXA9 | SEQ ID NO: 136415-136493 |
| human_HOXB1 | SEQ ID NO: 136494-136581 |
| human_HOXB2 | SEQ ID NO: 136582-136686 |
| human_HOXB3 | SEQ ID NO: 136687-136813 |
| human_HOXB4 | SEQ ID NO: 136814-136886 |
| human_HOXB5 | SEQ ID NO: 136887-136965 |
| human_HOXB6 | SEQ ID NO: 136966-137030 |

TABLE 5-continued

List of SEQ ID NOs: 1-244,000 denoting viral
or transcription factor specificity Virus/Source Gene

| | |
|---|---|
| human_HOXB7 | SEQ ID NO: 137031-137093 |
| human_HOXB9 | SEQ ID NO: 137094-137166 |
| human_HOXC10 | SEQ ID NO: 137167-137266 |
| human_HOXC11 | SEQ ID NO: 137267-137355 |
| human_HOXC4 | SEQ ID NO: 137356-137432 |
| human_HOXC5 | SEQ ID NO: 137433-137496 |
| human_HOXC6 | SEQ ID NO: 137497-137564 |
| human_HOXD10 | SEQ ID NO: 137565-137664 |
| human_HOXD13 | SEQ ID NO: 137665-137765 |
| human_HOXD3 | SEQ ID NO: 137766-137892 |
| human_HOXD4 | SEQ ID NO: 137893-137966 |
| human_HOXD8 | SEQ ID NO: 137967-138051 |
| human_HOXD9 | SEQ ID NO: 138052-138154 |
| human_HR | SEQ ID NO: 138155-138492 |
| human_HSF1 | SEQ ID NO: 138493-138649 |
| human_HSF2 | SEQ ID NO: 138650-138808 |
| human_HSF4 | SEQ ID NO: 138809-138944 |
| human_HSF5 | SEQ ID NO: 138945-139121 |
| human_HSFX1 | SEQ ID NO: 139122-139246 |
| human_HSFX2 | SEQ ID NO: 139247-139371 |
| human_HSFX3 | SEQ ID NO: 139372-139469 |
| human_HSFX4 | SEQ ID NO: 139470-139567 |
| human_HSFY1 | SEQ ID NO: 139568-139626 |
| human_HSFY2 | SEQ ID NO: 139627-139744 |
| human_IER2 | SEQ ID NO: 139745-139809 |
| human_IFI16 | SEQ ID NO: 139810-140042 |
| human_IKZF1 | SEQ ID NO: 140043-140196 |
| human_IKZF2 | SEQ ID NO: 140197-140209 |
| human_IKZF3 | SEQ ID NO: 140210-140286 |
| human_IKZF4 | SEQ ID NO: 140287-140459 |
| human_IKZF5 | SEQ ID NO: 140460-140583 |
| human_INSM1 | SEQ ID NO: 140584-140734 |
| human_IRF1 | SEQ ID NO: 140735-140829 |
| human_IRF2 | SEQ ID NO: 140830-140932 |
| human_IRF2BP1 | SEQ ID NO: 140933-141105 |
| human_IRF2BP2 | SEQ ID NO: 141106-141279 |
| human_IRF2BPL | SEQ ID NO: 141280-141516 |
| human_IRF3 | SEQ ID NO: 141517-141642 |
| human_IRF4 | SEQ ID NO: 141643-141775 |
| human_IRF5 | SEQ ID NO: 141776-141922 |
| human_IRF6 | SEQ ID NO: 141923-142060 |
| human_IRF7 | SEQ ID NO: 142061-142213 |
| human_IRF8 | SEQ ID NO: 142214-142339 |
| human_IRF9 | SEQ ID NO: 142340-142400 |
| human_ISL1 | SEQ ID NO: 142401-142503 |
| human_JARID2 | SEQ ID NO: 142504-142875 |
| human_JDP2 | SEQ ID NO: 142876-142925 |
| human_JMJD1C | SEQ ID NO: 142926-143685 |
| human_JUN | SEQ ID NO: 143686-143782 |
| human_JUNB | SEQ ID NO: 143783-143884 |
| human_JUND | SEQ ID NO: 143885-143986 |
| human_KAT2B | SEQ ID NO: 143987-144233 |
| human_KAT7 | SEQ ID NO: 144234-144414 |
| human_KCNIP3 | SEQ ID NO: 144415-144489 |
| human_KDM1A | SEQ ID NO: 144490-144750 |
| human_KDM2B | SEQ ID NO: 144751-145149 |
| human_KDM3A | SEQ ID NO: 145150-145543 |
| human_KDM3B | SEQ ID NO: 145544-146069 |
| human_KDM5A | SEQ ID NO: 146070-146574 |
| human_KDM6A | SEQ ID NO: 146575-146992 |
| human_KDM6B | SEQ ID NO: 146993-147494 |
| human_KLF1 | SEQ ID NO: 147495-147600 |
| human_KLF10 | SEQ ID NO: 147601-147742 |
| human_KLF11 | SEQ ID NO: 147743-147893 |
| human_KLF12 | SEQ ID NO: 147894-148011 |
| human_KLF13 | SEQ ID NO: 148012-148095 |
| human_KLF15 | SEQ ID NO: 148096-148218 |
| human_KLF16 | SEQ ID NO: 148219-148291 |
| human_KLF17 | SEQ ID NO: 148292-148406 |
| human_KLF3 | SEQ ID NO: 148407-148507 |
| human_KLF4 | SEQ ID NO: 148508-148649 |
| human_KLF5 | SEQ ID NO: 148650-148784 |
| human_KLF6 | SEQ ID NO: 148785-148866 |
| human_KLF7 | SEQ ID NO: 148867-148954 |
| human_KLF8 | SEQ ID NO: 148955-149029 |

TABLE 5-continued

List of SEQ ID NOs: 1-244,000 denoting viral
or transcription factor specificity Virus/Source Gene

| | |
|---|---|
| human_KMT2A | SEQ ID NO: 149030-150218 |
| human_KMT2D | SEQ ID NO: 150219-151877 |
| human_LDB1 | SEQ ID NO: 151878-151998 |
| human_LEF1 | SEQ ID NO: 151999-152116 |
| human_LHX2 | SEQ ID NO: 152117-152236 |
| human_LHX3 | SEQ ID NO: 152237-152354 |
| human_LITAF | SEQ ID NO: 152355-152400 |
| human_LMO2 | SEQ ID NO: 152401-152466 |
| human_LMO4 | SEQ ID NO: 152467-152513 |
| human_LMX1A | SEQ ID NO: 152514-152625 |
| human_LMX1B | SEQ ID NO: 152626-152745 |
| human_LONP1 | SEQ ID NO: 152746-153031 |
| human_LRRFIP1 | SEQ ID NO: 153032-153264 |
| human_LYL1 | SEQ ID NO: 153265-153346 |
| human_MACC1 | SEQ ID NO: 153347-153599 |
| human_MAF | SEQ ID NO: 153600-153718 |
| human_MAF1 | SEQ ID NO: 153719-153793 |
| human_MAFA | SEQ ID NO: 153794-153897 |
| human_MAFB | SEQ ID NO: 153898-153992 |
| human_MAFF | SEQ ID NO: 153993-154039 |
| human_MAFG | SEQ ID NO: 154040-154085 |
| human_MAFK | SEQ ID NO: 154086-154130 |
| human_MAX | SEQ ID NO: 154131-154157 |
| human_MAZ | SEQ ID NO: 154158-154303 |
| human_MBD2 | SEQ ID NO: 154304-154424 |
| human_MBD3 | SEQ ID NO: 154425-154500 |
| human_MED1 | SEQ ID NO: 154501-154972 |
| human_MED2 | SEQ ID NO: 154973-155623 |
| human_MED8 | SEQ ID NO: 155624-155711 |
| human_MEF2A | SEQ ID NO: 155712-155858 |
| human_MEF2B | SEQ ID NO: 155859-155968 |
| human_MEF2C | SEQ ID NO: 155969-156111 |
| human_MEF2D | SEQ ID NO: 156112-156265 |
| human_MEIS1 | SEQ ID NO: 156266-156380 |
| human_MEIS2 | SEQ ID NO: 156381-156468 |
| human_MEN1 | SEQ ID NO: 156469-156650 |
| human_MEOX1 | SEQ ID NO: 156651-156724 |
| human_MEOX2 | SEQ ID NO: 156725-156813 |
| human_MESP1 | SEQ ID NO: 156814-156891 |
| human_MESP2 | SEQ ID NO: 156892-157008 |
| human_MITF | SEQ ID NO: 157009-157162 |
| human_MIXL1 | SEQ ID NO: 157163-157229 |
| human_MLX | SEQ ID NO: 157230-157316 |
| human_MLXIP | SEQ ID NO: 157317-157590 |
| human_MLXIPL | SEQ ID NO: 157591-157760 |
| human_MMP12 | SEQ ID NO: 157761-157899 |
| human_MNT | SEQ ID NO: 157900-158071 |
| human_MRTFA | SEQ ID NO: 158072-158359 |
| human_MSC | SEQ ID NO: 158360-158419 |
| human_MSGN1 | SEQ ID NO: 158420-158475 |
| human_MSX1 | SEQ ID NO: 158476-158564 |
| human_MSX2 | SEQ ID NO: 158565-158642 |
| human_MTA1 | SEQ ID NO: 158643-158854 |
| human_MTA2 | SEQ ID NO: 158855-159052 |
| human_MTERF3 | SEQ ID NO: 159053-159175 |
| | SEQ ID NOs: 159176-244000 |
| | |
| human_MTF1 | SEQ ID NO: 159176-159399 |
| human_MTF2 | SEQ ID NO: 159400-159575 |
| human_MTOR | SEQ ID NO: 159576-160338 |
| human_MUC1 | SEQ ID NO: 160339-160418 |
| human_MXD1 | SEQ ID NO: 160419-160482 |
| human_MXD3 | SEQ ID NO: 160483-160542 |
| human_MXI1 | SEQ ID NO: 160543-160608 |
| human_MYB | SEQ ID NO: 160609-160834 |
| human_MYBBP1A | SEQ ID NO: 160835-161231 |
| human_MYBL1 | SEQ ID NO: 161232-161454 |
| human_MYBL2 | SEQ ID NO: 161455-161662 |
| human_MYC | SEQ ID NO: 161663-161792 |
| human_MYCN | SEQ ID NO: 161793-161929 |
| human_MYEF2 | SEQ ID NO: 161930-161965 |
| human_MYF5 | SEQ ID NO: 161966-162039 |
| human_MYF6 | SEQ ID NO: 162040-162109 |
| human_MYOCD | SEQ ID NO: 162110-162388 |
| human_MYOD1 | SEQ ID NO: 162389-162482 |

TABLE 5-continued

List of SEQ ID NOs: 1-244,000 denoting viral
or transcription factor specificity Virus/Source Gene

| | |
|---|---|
| human_MYOG | SEQ ID NO: 162483-162547 |
| human_MYPOP | SEQ ID NO: 162548-162665 |
| human_MYT1 | SEQ ID NO: 162666-162999 |
| human_MYT1L | SEQ ID NO: 163000-163352 |
| human_MZF1 | SEQ ID NO: 163353-163570 |
| human_NACC2 | SEQ ID NO: 163571-163744 |
| human_NANOG | SEQ ID NO: 163745-163833 |
| human_NCOA2 | SEQ ID NO: 163834-164270 |
| human_NCOR1 | SEQ ID NO: 164271-165000 |
| human_NCOR2 | SEQ ID NO: 165001-165752 |
| human_NDN | SEQ ID NO: 165753-165846 |
| human_NEUROD1 | SEQ ID NO: 165847-165951 |
| human_NEUROD2 | SEQ ID NO: 165952-166063 |
| human_NEUROD6 | SEQ ID NO: 166064-166162 |
| human_NEUROG1 | SEQ ID NO: 166163-166231 |
| human_NEUROG2 | SEQ ID NO: 166232-166310 |
| human_NEUROG3 | SEQ ID NO: 166311-166372 |
| human_NFAT5 | SEQ ID NO: 166373-166829 |
| human_NFATC1 | SEQ ID NO: 166830-167074 |
| human_NFATC2 | SEQ ID NO: 167075-167348 |
| human_NFATC3 | SEQ ID NO: 167349-167668 |
| human_NFATC4 | SEQ ID NO: 167669-167936 |
| human_NFE2 | SEQ ID NO: 167937-168046 |
| human_NFE2L1 | SEQ ID NO: 168047-168266 |
| human_NFE2L2 | SEQ ID NO: 168267-168445 |
| human_NFE2L3 | SEQ ID NO: 168446-168651 |
| human_NFIA | SEQ ID NO: 168652-168799 |
| human_NFIB | SEQ ID NO: 168800-168923 |
| human_NFIC | SEQ ID NO: 168924-169049 |
| human_NFIL3 | SEQ ID NO: 169050-169185 |
| human_NFKB1 | SEQ ID NO: 169186-169474 |
| human_NFKB2 | SEQ ID NO: 169475-169742 |
| human_NFX1 | SEQ ID NO: 169743-169990 |
| human_NFXL1 | SEQ ID NO: 169991-170261 |
| human_NFYA | SEQ ID NO: 170262-170354 |
| human_NFYB | SEQ ID NO: 170355-170414 |
| human_NFYC | SEQ ID NO: 170415-170549 |
| human_NHLH1 | SEQ ID NO: 170550-170587 |
| human_NHLH2 | SEQ ID NO: 170588-170625 |
| human_NKRF | SEQ ID NO: 170626-170830 |
| human_NKX2-1 | SEQ ID NO: 170831-170948 |
| human_NKX2-2 | SEQ ID NO: 170949-171028 |
| human_NKX2-5 | SEQ ID NO: 171029-171123 |
| human_NKX2-6 | SEQ ID NO: 171124-171211 |
| human_NKX2-8 | SEQ ID NO: 171212-171281 |
| human_NKX3-1 | SEQ ID NO: 171282-171349 |
| human_NKX3-2 | SEQ ID NO: 171350-171447 |
| human_NKX6-1 | SEQ ID NO: 171448-171555 |
| human_NKX6-2 | SEQ ID NO: 171556-171636 |
| human_NLRC5 | SEQ ID NO: 171637-172194 |
| human_NME1 | SEQ ID NO: 172195-172245 |
| human_NONO | SEQ ID NO: 172246-172384 |
| human_NOTCH1 | SEQ ID NO: 172385-173148 |
| human_NPAS2 | SEQ ID NO: 173149-173393 |
| human_NPAS4 | SEQ ID NO: 173394-173631 |
| human_NPM1 | SEQ ID NO: 173632-173717 |
| human_NR1D1 | SEQ ID NO: 173718-173899 |
| human_NR1D2 | SEQ ID NO: 173900-174071 |
| human_NR1H2 | SEQ ID NO: 174072-174207 |
| human_NR1H3 | SEQ ID NO: 174208-174321 |
| human_NR1H4 | SEQ ID NO: 174322-174463 |
| human_NR1I2 | SEQ ID NO: 174464-174603 |
| human_NR1I3 | SEQ ID NO: 174604-174706 |
| human_NR2C1 | SEQ ID NO: 174707-174885 |
| human_NR2C2 | SEQ ID NO: 174886-175067 |
| human_NR2E3 | SEQ ID NO: 175068-175188 |
| human_NR2F1 | SEQ ID NO: 175189-175313 |
| human_NR2F6 | SEQ ID NO: 175314-175432 |
| human_NR3C1 | SEQ ID NO: 175433-175663 |
| human_NR4A1 | SEQ ID NO: 175664-175840 |
| human_NR4A2 | SEQ ID NO: 175841-176017 |
| human_NR4A3 | SEQ ID NO: 176018-176206 |
| human_NR5A1 | SEQ ID NO: 176207-176342 |
| human_NR5A2 | SEQ ID NO: 176343-176488 |
| human_NR6A1 | SEQ ID NO: 176489-176630 |

TABLE 5-continued

List of SEQ ID NOs: 1-244,000 denoting viral
or transcription factor specificity Virus/Source Gene

| | |
|---|---|
| human_NRF1 | SEQ ID NO: 176631-176779 |
| human_NRIP1 | SEQ ID NO: 176780-177124 |
| human_NRL | SEQ ID NO: 177125-177193 |
| human_NSD1 | SEQ ID NO: 177194-177919 |
| human_ONECUT2 | SEQ ID NO: 177920-178068 |
| human_ONECUT3 | SEQ ID NO: 178069-178214 |
| human_OSR1 | SEQ ID NO: 178215-178292 |
| human_OSR2 | SEQ ID NO: 178293-178383 |
| human_OTX1 | SEQ ID NO: 178384-178487 |
| human_OTX2 | SEQ ID NO: 178488-178574 |
| human_OVOL1 | SEQ ID NO: 178575-178652 |
| human_PARP1 | SEQ ID NO: 178653-178954 |
| human_PATZ1 | SEQ ID NO: 178955-179158 |
| human_PAX1 | SEQ ID NO: 179159-179316 |
| human_PAX2 | SEQ ID NO: 179317-179432 |
| human_PAX4 | SEQ ID NO: 179433-179533 |
| human_PAX5 | SEQ ID NO: 179534-179648 |
| human_PAX6 | SEQ ID NO: 179649-179772 |
| human_PAX8 | SEQ ID NO: 179773-179866 |
| human_PAX9 | SEQ ID NO: 179867-179966 |
| human_PAXBP1 | SEQ ID NO: 179967-180208 |
| human_PBX1 | SEQ ID NO: 180209-180335 |
| human_PBX2 | SEQ ID NO: 180336-180462 |
| human_PBX3 | SEQ ID NO: 180463-180590 |
| human_PCGF3 | SEQ ID NO: 180591-180660 |
| human_PCGF5 | SEQ ID NO: 180661-180735 |
| human_PCGF6 | SEQ ID NO: 180736-180815 |
| human_PDX1 | SEQ ID NO: 180816-180898 |
| human_PER1 | SEQ ID NO: 180899-181283 |
| human_PER2 | SEQ ID NO: 181284-181657 |
| human_PER3 | SEQ ID NO: 181658-182018 |
| human_PGR | SEQ ID NO: 182019-182265 |
| human_PHB | SEQ ID NO: 182266-182344 |
| human_PHOX2A | SEQ ID NO: 182345-182427 |
| human_PHOX2B | SEQ ID NO: 182428-182519 |
| human_PIH1D1 | SEQ ID NO: 182520-182604 |
| human_PITX1 | SEQ ID NO: 182605-182696 |
| human_PITX2 | SEQ ID NO: 182697-182791 |
| human_PITX3 | SEQ ID NO: 182792-182879 |
| human_PKNOX2 | SEQ ID NO: 182880-183018 |
| human_PLAG1 | SEQ ID NO: 183019-183166 |
| human_PLAGL1 | SEQ ID NO: 183167-183303 |
| human_POLRMT | SEQ ID NO: 183304-183670 |
| human_POU1F1 | SEQ ID NO: 183671-183763 |
| human_POU2AF1 | SEQ ID NO: 183764-183838 |
| human_POU2F1 | SEQ ID NO: 183839-184062 |
| human_POU2F2 | SEQ ID NO: 184063-184204 |
| human_POU2F3 | SEQ ID NO: 184205-184333 |
| human_POU3F2 | SEQ ID NO: 184334-184464 |
| human_POU3F4 | SEQ ID NO: 184465-184570 |
| human_POU4F1 | SEQ ID NO: 184571-184694 |
| human_POU4F2 | SEQ ID NO: 184695-184815 |
| human_POU4F3 | SEQ ID NO: 184816-184914 |
| human_POU5F1 | SEQ ID NO: 184915-185020 |
| human_POU6F1 | SEQ ID NO: 185021-185201 |
| human_PPARA | SEQ ID NO: 185202-185339 |
| human_PPARD | SEQ ID NO: 185340-185445 |
| human_PPARG | SEQ ID NO: 185446-185594 |
| human_PRDM1 | SEQ ID NO: 185595-185829 |
| human_PRDM11 | SEQ ID NO: 185830-185970 |
| human_PRDM12 | SEQ ID NO: 185971-186078 |
| human_PRDM13 | SEQ ID NO: 186079-186288 |
| human_PRDM14 | SEQ ID NO: 186289-186457 |
| human_PRDM15 | SEQ ID NO: 186458-186907 |
| human_PRDM2 | SEQ ID NO: 186908-187420 |
| human_PRDM4 | SEQ ID NO: 187421-187658 |
| human_PRDM5 | SEQ ID NO: 187659-187845 |
| human_PRDM6 | SEQ ID NO: 187846-188021 |
| human_PRDM7 | SEQ ID NO: 188022-188166 |
| human_PRDM9 | SEQ ID NO: 188167-188432 |
| human_PRDX5 | SEQ ID NO: 188433-188494 |
| human_PRKN | SEQ ID NO: 188495-188574 |
| human_PRMT5 | SEQ ID NO: 188575-188745 |
| human_PROP1 | SEQ ID NO: 188746-188811 |
| human_PROX1 | SEQ ID NO: 188812-189030 |

TABLE 5-continued

List of SEQ ID NOs: 1-244,000 denoting viral
or transcription factor specificity Virus/Source Gene

| | |
|---|---|
| human_PRRX1 | SEQ ID NO: 189031-189101 |
| human_PSPC1 | SEQ ID NO: 189102-189256 |
| human_PTF1A | SEQ ID NO: 189257-189352 |
| human_PURA | SEQ ID NO: 189353-189446 |
| human_PURB | SEQ ID NO: 189447-189537 |
| human_PURG | SEQ ID NO: 189538-189631 |
| human_RAI1 | SEQ ID NO: 189632-190201 |
| human_RARA | SEQ ID NO: 190202-190337 |
| human_RARB | SEQ ID NO: 190338-190469 |
| human_RARG | SEQ ID NO: 190470-190600 |
| human_RAX | SEQ ID NO: 190601-190629 |
| human_RAX2 | SEQ ID NO: 190630-190682 |
| human_RB1 | SEQ ID NO: 190683-190958 |
| human_RBBP4 | SEQ ID NO: 190959-191083 |
| human_RBBP5 | SEQ ID NO: 191084-191242 |
| human_RBL1 | SEQ ID NO: 191243-191544 |
| human_RBL2 | SEQ ID NO: 191545-191884 |
| human_RBMX | SEQ ID NO: 191885-191999 |
| human_RBPJ | SEQ ID NO: 192000-192147 |
| human_RBPJL | SEQ ID NO: 192148-192300 |
| human_RCOR1 | SEQ ID NO: 192301-192443 |
| human_RCOR2 | SEQ ID NO: 192444-192598 |
| human_RCOR3 | SEQ ID NO: 192599-192744 |
| human_REL | SEQ ID NO: 192745-192928 |
| human_RELA | SEQ ID NO: 192929-193090 |
| human_RELB | SEQ ID NO: 193091-193262 |
| human_REST | SEQ ID NO: 193263-193589 |
| human_RFX1 | SEQ ID NO: 193590-193881 |
| human_RFX2 | SEQ ID NO: 193882-194096 |
| human_RFX3 | SEQ ID NO: 194097-194218 |
| human_RFX4 | SEQ ID NO: 194219-194408 |
| human_RFX5 | SEQ ID NO: 194409-194591 |
| human_RFX6 | SEQ ID NO: 194592-194867 |
| human_RFX7 | SEQ ID NO: 194868-195274 |
| human_RFX8 | SEQ ID NO: 195275-195414 |
| human_RNF10 | SEQ ID NO: 195415-195655 |
| human_RORA | SEQ ID NO: 195656-195820 |
| human_RORB | SEQ ID NO: 195821-195956 |
| human_RORC | SEQ ID NO: 195957-196109 |
| human_RPS3 | SEQ ID NO: 196110-196185 |
| human_RPTOR | SEQ ID NO: 196186-196583 |
| human_RREB1 | SEQ ID NO: 196584-197024 |
| human_RRN3 | SEQ ID NO: 197025-197217 |
| human_RUNX1 | SEQ ID NO: 197218-197359 |
| human_RUNX2 | SEQ ID NO: 197360-197513 |
| human_RUNX3 | SEQ ID NO: 197514-197640 |
| human_RUVBL2 | SEQ ID NO: 197641-197777 |
| human_RXRA | SEQ ID NO: 197778-197913 |
| human_RXRB | SEQ ID NO: 197914-198071 |
| human_SAFB | SEQ ID NO: 198072-198343 |
| human_SALL1 | SEQ ID NO: 198344-198738 |
| human_SALL2 | SEQ ID NO: 198739-199038 |
| human_SARS | SEQ ID NO: 199039-199190 |
| human_SATB1 | SEQ ID NO: 199191-199417 |
| human_SATB2 | SEQ ID NO: 199418-199635 |
| human_SCRT1 | SEQ ID NO: 199636-199737 |
| human_SCRT2 | SEQ ID NO: 199738-199827 |
| human_SCX | SEQ ID NO: 199828-199885 |
| human_SETX | SEQ ID NO: 199886-200686 |
| human_SFPQ | SEQ ID NO: 200687-200896 |
| human_SIN3A | SEQ ID NO: 200897-201276 |
| human_SIRT1 | SEQ ID NO: 201277-201498 |
| human_SIX1 | SEQ ID NO: 201499-201581 |
| human_SIX2 | SEQ ID NO: 201582-201666 |
| human_SIX3 | SEQ ID NO: 201667-201763 |
| human_SIX4 | SEQ ID NO: 201764-201995 |
| human_SIX5 | SEQ ID NO: 201996-202215 |
| human_SIX6 | SEQ ID NO: 202216-202287 |
| human_SKIL | SEQ ID NO: 202288-202490 |
| human_SMAD1 | SEQ ID NO: 202491-202627 |
| human_SMAD2 | SEQ ID NO: 202628-202765 |
| human_SMAD3 | SEQ ID NO: 202766-202890 |
| human_SMAD4 | SEQ ID NO: 202891-203053 |
| human_SMAD5 | SEQ ID NO: 203054-203190 |
| human_SMAD6 | SEQ ID NO: 203191-203337 |

TABLE 5-continued

List of SEQ ID NOs: 1-244,000 denoting viral
or transcription factor specificity Virus/Source Gene

| | |
|---|---|
| human_SMAD7 | SEQ ID NO: 203338-203463 |
| human_SMARCA2 | SEQ ID NO: 203464-203938 |
| human_SMARCA4 | SEQ ID NO: 203939-204430 |
| human_SMARCB1 | SEQ ID NO: 204431-204541 |
| human_SMARCC1 | SEQ ID NO: 204542-204870 |
| human_SMARCC2 | SEQ ID NO: 204871-205232 |
| human_SMARCD2 | SEQ ID NO: 205233-205375 |
| human_SMARCE1 | SEQ ID NO: 205376-205482 |
| human_SMYD3 | SEQ ID NO: 205483-205608 |
| human_SNAI1 | SEQ ID NO: 205609-205685 |
| human_SNAI2 | SEQ ID NO: 205686-205763 |
| human_SNAI3 | SEQ ID NO: 205764-205848 |
| human_SNCA | SEQ ID NO: 205849-205879 |
| human_SOX1 | SEQ ID NO: 205880-205994 |
| human_SOX10 | SEQ ID NO: 205995-206132 |
| human_SOX11 | SEQ ID NO: 206133-206262 |
| human_SOX12 | SEQ ID NO: 206263-206354 |
| human_SOX13 | SEQ ID NO: 206355-206538 |
| human_SOX17 | SEQ ID NO: 206539-206660 |
| human_SOX18 | SEQ ID NO: 206661-206773 |
| human_SOX2 | SEQ ID NO: 206774-206866 |
| human_SOX21 | SEQ ID NO: 206867-206947 |
| human_SOX3 | SEQ ID NO: 206948-207079 |
| human_SOX4 | SEQ ID NO: 207080-207219 |
| human_SOX6 | SEQ ID NO: 207220-207459 |
| human_SOX7 | SEQ ID NO: 207460-207573 |
| human_SOX8 | SEQ ID NO: 207574-207705 |
| human_SOX9 | SEQ ID NO: 207706-207856 |
| human_SP1 | SEQ ID NO: 207857-208089 |
| human_SP2 | SEQ ID NO: 208090-208271 |
| human_SP3 | SEQ ID NO: 208272-208503 |
| human_SP5 | SEQ ID NO: 208504-208620 |
| human_SP7 | SEQ ID NO: 208621-208747 |
| human_SPI1 | SEQ ID NO: 208748-208826 |
| human_SPIB | SEQ ID NO: 208827-208877 |
| human_SPIC | SEQ ID NO: 208878-208949 |
| human_SREBF1 | SEQ ID NO: 208950-209291 |
| human_SREBF2 | SEQ ID NO: 209292-209631 |
| human_SRF | SEQ ID NO: 209632-209781 |
| human_SSBP2 | SEQ ID NO: 209782-209887 |
| human_SSBP3 | SEQ ID NO: 209888-209995 |
| human_SSBP4 | SEQ ID NO: 209996-210108 |
| human_ST18 | SEQ ID NO: 210109-210420 |
| human_STAT1 | SEQ ID NO: 210421-210631 |
| human_STAT3 | SEQ ID NO: 210632-210860 |
| human_STAT5B | SEQ ID NO: 210861-211094 |
| human_STAT6 | SEQ ID NO: 211095-211346 |
| human_STOX1 | SEQ ID NO: 211347-211641 |
| human_SUV39H1 | SEQ ID NO: 211642-211766 |
| human_SUV39H2 | SEQ ID NO: 211767-211887 |
| human_SUZ12 | SEQ ID NO: 211888-212107 |
| human_TAF1 | SEQ ID NO: 212108-212673 |
| human_TAF1B | SEQ ID NO: 212674-212847 |
| human_TAF1C | SEQ ID NO: 212848-213077 |
| human_TAF2 | SEQ ID NO: 213078-213435 |
| human_TAF5 | SEQ ID NO: 213436-213673 |
| human_TAF7 | SEQ ID NO: 213674-213776 |
| human_TAF7L | SEQ ID NO: 213777-213864 |
| human_TAF9 | SEQ ID NO: 213865-213941 |
| human_TAF9B | SEQ ID NO: 213942-214014 |
| human_TAL1 | SEQ ID NO: 214015-214111 |
| human_TAL2 | SEQ ID NO: 214112-214141 |
| human_TBL1X | SEQ ID NO: 214142-214312 |
| human_TBL1XR1 | SEQ ID NO: 214313-214464 |
| human_TBP | SEQ ID NO: 214465-214564 |
| human_TBPL1 | SEQ ID NO: 214565-214618 |
| human_TBPL2 | SEQ ID NO: 214619-214728 |
| human_TBR1 | SEQ ID NO: 214729-214930 |
| human_TBX15 | SEQ ID NO: 214931-215108 |
| human_TBX18 | SEQ ID NO: 215109-215288 |
| human_TBX19 | SEQ ID NO: 215289-215420 |
| human_TBX2 | SEQ ID NO: 215421-215631 |
| human_TBX20 | SEQ ID NO: 215632-215763 |
| human_TBX21 | SEQ ID NO: 215764-215921 |
| human_TBX22 | SEQ ID NO: 215922-216075 |

TABLE 5-continued

List of SEQ ID NOs: 1-244,000 denoting viral
or transcription factor specificity

| Virus/Source Gene | |
|---|---|
| human_TBX3 | SEQ ID NO: 216076-216296 |
| human_TBX5 | SEQ ID NO: 216297-216449 |
| human_TBX6 | SEQ ID NO: 216450-216578 |
| human_TBXT | SEQ ID NO: 216579-216706 |
| human_TCF12 | SEQ ID NO: 216707-216908 |
| human_TCF15 | SEQ ID NO: 216909-216966 |
| human_TCF20 | SEQ ID NO: 216967-217545 |
| human_TCF21 | SEQ ID NO: 217546-217597 |
| human_TCF3 | SEQ ID NO: 217598-217791 |
| human_TCF4 | SEQ ID NO: 217792-217990 |
| human_TCF7 | SEQ ID NO: 217991-218103 |
| human_TCF7L1 | SEQ ID NO: 218104-218277 |
| human_TCF7L2 | SEQ ID NO: 218278-218413 |
| human_TCFL5 | SEQ ID NO: 218414-218561 |
| human_TEAD1 | SEQ ID NO: 218562-218666 |
| human_TEAD2 | SEQ ID NO: 218667-218798 |
| human_TEAD3 | SEQ ID NO: 218799-218926 |
| human_TEAD4 | SEQ ID NO: 218927-219015 |
| human_TEF | SEQ ID NO: 219016-219104 |
| human_TFAM | SEQ ID NO: 219105-219166 |
| human_TFAP2A | SEQ ID NO: 219167-219294 |
| human_TFAP2B | SEQ ID NO: 219295-219430 |
| human_TFAP2C | SEQ ID NO: 219431-219563 |
| human_TFAP2D | SEQ ID NO: 219564-219696 |
| human_TFAP2E | SEQ ID NO: 219697-219826 |
| human_TFAP4 | SEQ ID NO: 219827-219925 |
| human_TFCP2 | SEQ ID NO: 219926-220073 |
| human_TFCP2L1 | SEQ ID NO: 220074-220215 |
| human_TFDP1 | SEQ ID NO: 220216-220336 |
| human_TFDP2 | SEQ ID NO: 220337-220449 |
| human_TFE3 | SEQ ID NO: 220450-220619 |
| human_TFEB | SEQ ID NO: 220620-220760 |
| human_TFEC | SEQ ID NO: 220761-220862 |
| human_TGIF1 | SEQ ID NO: 220863-220980 |
| human_THAP1 | SEQ ID NO: 220981-221042 |
| human_THAP11 | SEQ ID NO: 221043-221134 |
| human_THRA | SEQ ID NO: 221135-221279 |
| human_THRAP3 | SEQ ID NO: 221280-221563 |
| human_THRB | SEQ ID NO: 221564-221704 |
| human_TIPARP | SEQ ID NO: 221705-221899 |
| human_TLX1 | SEQ ID NO: 221900-221996 |
| human_TNF | SEQ ID NO: 221997-222064 |
| human_TOP1 | SEQ ID NO: 222065-222291 |
| human_TOX2 | SEQ ID NO: 222292-222441 |
| human_TOX3 | SEQ ID NO: 222442-222612 |
| human_TP53 | SEQ ID NO: 222613-222728 |
| human_TP63 | SEQ ID NO: 222729-222930 |
| human_TP73 | SEQ ID NO: 222931-223078 |
| human_TRERF1 | SEQ ID NO: 223079-223415 |
| human_TRIM24 | SEQ ID NO: 223416-223728 |
| human_TRPS1 | SEQ ID NO: 223729-224110 |
| human_TWIST1 | SEQ ID NO: 224111-224168 |
| human_TXK | SEQ ID NO: 224169-224324 |
| human_UBTF | SEQ ID NO: 224325-224551 |
| human_UHRF1 | SEQ ID NO: 224552-224787 |
| human_USP3 | SEQ ID NO: 224788-224941 |
| human_UTY | SEQ ID NO: 224942-225263 |
| human_VAX1 | SEQ ID NO: 225264-225361 |
| human_VAX2 | SEQ ID NO: 225362-225446 |
| human_VDR | SEQ ID NO: 225447-225572 |
| human_VEZF1 | SEQ ID NO: 225573-225726 |
| human_WBP2 | SEQ ID NO: 225727-225802 |
| human_WNT1 | SEQ ID NO: 225803-225911 |
| human_WNT11 | SEQ ID NO: 225912-226015 |
| human_WNT5A | SEQ ID NO: 226016-226127 |
| human_WT1 | SEQ ID NO: 226128-226215 |
| human_XBP1 | SEQ ID NO: 226216-226291 |
| human_XRCC5 | SEQ ID NO: 226292-226508 |
| human_XRCC6 | SEQ ID NO: 226509-226689 |
| human_XRN2 | SEQ ID NO: 226690-226972 |
| human_YAP1 | SEQ ID NO: 226973-227121 |
| human_YBX1 | SEQ ID NO: 227122-227216 |
| human_YBX3 | SEQ ID NO: 227217-227325 |
| human_YY1 | SEQ ID NO: 227326-227447 |
| human_YY2 | SEQ ID NO: 227448-227556 |

TABLE 5-continued

List of SEQ ID NOs: 1-244,000 denoting viral
or transcription factor specificity

| Virus/Source Gene | |
|---|---|
| human_ZBED1 | SEQ ID NO: 227557-227762 |
| human_ZBTB14 | SEQ ID NO: 227763-227895 |
| human_ZBTB16 | SEQ ID NO: 227896-228095 |
| human_ZBTB17 | SEQ ID NO: 228096-228336 |
| human_ZBTB2 | SEQ ID NO: 228337-228488 |
| human_ZBTB20 | SEQ ID NO: 228489-228686 |
| human_ZBTB24 | SEQ ID NO: 228687-228893 |
| human_ZBTB4 | SEQ ID NO: 228894-229195 |
| human_ZBTB48 | SEQ ID NO: 229196-229399 |
| human_ZBTB5 | SEQ ID NO: 229400-229600 |
| human_ZBTB7A | SEQ ID NO: 229601-229773 |
| human_ZBTB7B | SEQ ID NO: 229774-229933 |
| human_ZC3H4 | SEQ ID NO: 229934-230322 |
| human_ZC3H6 | SEQ ID NO: 230323-230677 |
| human_ZC3H8 | SEQ ID NO: 230678-230762 |
| human_ZEB1 | SEQ ID NO: 230763-231097 |
| human_ZFHX2 | SEQ ID NO: 231098-231866 |
| human_ZFHX3 | SEQ ID NO: 231867-232975 |
| human_ZFHX4 | SEQ ID NO: 232976-234058 |
| human_ZFP42 | SEQ ID NO: 234059-234149 |
| human_ZFPM1 | SEQ ID NO: 234150-234449 |
| human_ZGPAT | SEQ ID NO: 234450-234606 |
| human_ZHX3 | SEQ ID NO: 234607-234891 |
| human_ZIC1 | SEQ ID NO: 234892-235023 |
| human_ZIC2 | SEQ ID NO: 235024-235180 |
| human_ZIC3 | SEQ ID NO: 235181-235318 |
| human_ZIC4 | SEQ ID NO: 235319-235427 |
| human_ZIC5 | SEQ ID NO: 235428-235624 |
| human_ZKSCAN3 | SEQ ID NO: 235625-235783 |
| human_ZNF131 | SEQ ID NO: 235784-235958 |
| human_ZNF143 | SEQ ID NO: 235959-236138 |
| human_ZNF148 | SEQ ID NO: 236139-236374 |
| human_ZNF174 | SEQ ID NO: 236375-236494 |
| human_ZNF175 | SEQ ID NO: 236495-236705 |
| human_ZNF202 | SEQ ID NO: 236706-236897 |
| human_ZNF205 | SEQ ID NO: 236898-237061 |
| human_ZNF217 | SEQ ID NO: 237062-237373 |
| human_ZNF219 | SEQ ID NO: 237374-237587 |
| human_ZNF239 | SEQ ID NO: 237588-237722 |
| human_ZNF277 | SEQ ID NO: 237723-237855 |
| human_ZNF281 | SEQ ID NO: 237856-238121 |
| human_ZNF322 | SEQ ID NO: 238122-238239 |
| human_ZNF335 | SEQ ID NO: 238240-238639 |
| human_ZNF350 | SEQ ID NO: 238640-238796 |
| human_ZNF395 | SEQ ID NO: 238797-238948 |
| human_ZNF431 | SEQ ID NO: 238949-239119 |
| human_ZNF497 | SEQ ID NO: 239120-239266 |
| human_ZNF501 | SEQ ID NO: 239267-239345 |
| human_ZNF513 | SEQ ID NO: 239346-239505 |
| human_ZNF516 | SEQ ID NO: 239506-239852 |
| human_ZNF536 | SEQ ID NO: 239853-240240 |
| human_ZNF541 | SEQ ID NO: 240241-240642 |
| human_ZNF564 | SEQ ID NO: 240643-240806 |
| human_ZNF568 | SEQ ID NO: 240807-240997 |
| human_ZNF589 | SEQ ID NO: 240998-241104 |
| human_ZNF605 | SEQ ID NO: 241105-241303 |
| human_ZNF613 | SEQ ID NO: 241304-241486 |
| human_ZNF639 | SEQ ID NO: 241487-241629 |
| human_ZNF649 | SEQ ID NO: 241630-241778 |
| human_ZNF658 | SEQ ID NO: 241779-241961 |
| human_ZNF668 | SEQ ID NO: 241962-242151 |
| human_ZNF691 | SEQ ID NO: 242152-242243 |
| human_ZNF692 | SEQ ID NO: 242244-242397 |
| human_ZNF704 | SEQ ID NO: 242398-242518 |
| human_ZNF709 | SEQ ID NO: 242519-242708 |
| human_ZNF711 | SEQ ID NO: 242709-242934 |
| human_ZNF740 | SEQ ID NO: 242935-242990 |
| human_ZNF746 | SEQ ID NO: 242991-243181 |
| human_ZNF750 | SEQ ID NO: 243182-243396 |
| human_ZNF821 | SEQ ID NO: 243397-243517 |
| human_ZNF835 | SEQ ID NO: 243518-243676 |
| human_ZNF93 | SEQ ID NO: 243677-243860 |
| human_ZSCAN21 | SEQ ID NO: 243861-244000 |

REFERENCES

1. F. J. Isaacs, D. J. Dwyer, J. J. Collins, RNA synthetic biology. *Nature biotechnology* 24, 545 (2006).
2. A. A. Green, P. A. Silver, J. J. Collins, P. Yin, Toehold switches: de-novo-designed regulators of gene expression. *Cell* 159, 925-939 (2014).
3. K. Pardee et al., Rapid, low-cost detection of Zika virus using programmable biomolecular components. *Cell* 165, 1255-1266 (2016).
4. M. K. Takahashi et al., A low-cost paper-based synthetic biology platform for analyzing gut microbiota and host biomarkers. *Nature communications* 9, 3347 (2018).
5. A. A. Green et al., Complex cellular logic computation using ribocomputing devices. *Nature* 548, 117 (2017).
6. S.-J. Kim, M. Leong, M. B. Amrofell, Y. J. Lee, T. S. Moon, Modulating responses of toehold switches by an inhibitory hairpin. *ACS synthetic biology* 8, 601-605 (2019).
7. M. Krishnamurthy et al., Tunable riboregulator switches for post-transcriptional control of gene expression. *ACS synthetic biology* 4, 1326-1334 (2015).
8. J. Kim et al., De-Novo-Designed Translational Repressors for Multi-Input Cellular Logic. *bioRxiv,* 501783 (2018).
9. A. C.-Y. To et al., A comprehensive web tool for toehold switch design. *Bioinformatics* 34, 2862-2864 (2018).
10. H. K. Kim et al., Deep learning improves prediction of CRISPR-Cpf1 guide RNA activity. *Nature biotechnology* 36, 239 (2018).
11. S. Webb, Deep learning for biology. *Nature* 554, (2018).
12. C. Angermueller, T. Pärnamaa, L. Parts, O. Stegle, Deep learning for computational biology. *Molecular systems biology* 12, (2016).
13. M. Wainberg, D. Merico, A. Delong, B. J. Frey, Deep learning in biomedicine. *Nature biotechnology* 36, 829 (2018).
14. D. M. Camacho, K. M. Collins, R. K. Powers, J. C. Costello, J. J. Collins, Next-generation machine learning for biological networks. *Cell* 173, 1581-1592 (2018).
15. K. Pardee et al., Paper-based synthetic gene networks. *Cell* 159, 940-954 (2014).
16. D. Ma, L. Shen, K. Wu, C. W. Diehnelt, A. A. Green, Low-cost detection of norovirus using paper-based cell-free systems and synbody-based viral enrichment. *Synthetic Biology* 3, ysy018 (2018).
17. G. Chuai et al., DeepCRISPR: optimized CRISPR guide RNA design by deep learning. *Genome biology* 19, 80 (2018).
18. J. Luo, W. Chen, L. Xue, B. Tang, Prediction of activity and specificity of CRISPR-Cpf1 using convolutional deep learning neural networks. *BMC bioinformatics* 20, 332 (2019).
19. S. Zhang, H. Hu, T. Jiang, L. Zhang, J. Zeng, TITER: predicting translation initiation sites by deep learning. *Bioinformatics* 33, i234-i242 (2017).
20. J. Zuallaert, M. Kim, Y. Saeys, W. De Neve, in 2017 *IEEE International Conference on Bioinformatics and Biomedicine (BIBM).* (IEEE, 2017), pp. 1233-1237.
21. E. C. Alley, G. Khimulya, S. Biswas, M. AlQuraishi, G. M. Church, Unified rational protein engineering with sequence-only deep representation learning. *bioRxiv,* 589333 (2019).
22. D. B. Goodman, G. M. Church, S. Kosuri, Causes and effects of N-terminal codon bias in bacterial genes. *Science* 342, 475-479 (2013).
23. J. N. Zadeh, B. R. Wolfe, N. A. Pierce, Nucleic acid sequence design via efficient ensemble defect optimization. *Journal of computational chemistry* 32, 439-452 (2011).
24. R. M. Dirks, M. Lin, E. Winfree, N. A. Pierce, Paradigms for computational nucleic acid design. *Nucleic acids research* 32, 1392-1403 (2004).
25. R. Lorenz et al., ViennaRNA Package 2.0. *Algorithms for molecular biology* 6, 26 (2011).
26. H. M. Salis, E. A. Mirsky, C. A. Voigt, Automated design of synthetic ribosome binding sites to control protein expression. *Nature biotechnology* 27, 946 (2009).
27. A. Espah Borujeni et al., Precise quantification of translation inhibition by mRNA structures that overlap with the ribosomal footprint in N-terminal coding sequences. *Nucleic acids research* 45, 5437-5448 (2017).
28. A. Espah Borujeni, A. S. Channarasappa, H. M. Salis, Translation rate is controlled by coupled trade-offs between site accessibility, selective RNA unfolding and sliding at upstream standby sites. *Nucleic acids research* 42, 2646-2659 (2013).
29. A. Espah Borujeni, H. M. Salis, Translation initiation is controlled by RNA folding kinetics via a ribosome drafting mechanism. *Journal of the American Chemical Society* 138, 7016-7023 (2016).
30. B. Reeve, T. Hargest, C. Gilbert, T. Ellis, Predicting translation initiation rates for designing synthetic biology. *Frontiers in bioengineering and biotechnology* 2, 1 (2014).
31. M. M. Meyer, The role of mRNA structure in bacterial translational regulation. *Wiley Interdisciplinary Reviews: RNA* 8, e1370 (2017).
32. S. Badelt, S. Hammer, C. Flamm, I. L. Hofacker, in *Methods in enzymology.* (Elsevier, 2015), vol. 553, pp. 193-213.
33. B. Sauerwine, M. Widom, Kinetic Monte Carlo method applied to nucleic acid hairpin folding. *Physical Review E* 84, 061912 (2011).
34. V. I. Jurtz et al., An introduction to deep learning on biological sequence data: examples and solutions. *Bioinformatics* 33, 3685-3690 (2017).
35. X.-Q. Liu, B.-X. Li, G.-R. Zeng, Q.-Y. Liu, D.-M. Ai, Prediction of Long Non-Coding RNAs Based on Deep Learning. *Genes* 10, 273 (2019).
36. J. Baek, B. Lee, S. Kwon, S. Yoon, Lncrnanet: long non-coding ma identification using deep learning. *Bioinformatics* 34, 3889-3897 (2018).
37. G. Aoki, Y. Sakakibara, Convolutional neural networks for classification of alignments of non-coding RNA sequences. *Bioinformatics* 34, i237-i244 (2018).
38. A. Fiannaca, M. La Rosa, L. La Paglia, R. Rizzo, A. Urso, nRC: non-coding RNA Classifier based on structural features. *BioData mining* 10, 27 (2017).
39. N. Frosst, G. Hinton, Distilling a neural network into a soft decision tree. *arXiv preprint arXiv:*1711.09784, (2017).
40. P. K. Koo, S. R. Eddy, Representation Learning of Genomic Sequence Motifs with Convolutional Neural Networks. *BioRxiv,* 362756 (2018).
41. K. Simonyan, A. Vedaldi, A. Zisserman, Deep inside convolutional networks: Visualising image classification models and saliency maps. *arXiv preprint arXiv:* 1312.6034, (2013).
42. A. Dhawan, J. G. Scott, A. L. Harris, F. M. Buffa, Pan-cancer characterisation of microRNA across cancer hallmarks reveals microRNA-mediated downregulation of tumour suppressors. *Nature communications* 9, 5228 (2018).

43. Y. Xin-wei et al., STAT3 overexpression promotes metastasis in intrahepatic cholangiocarcinoma and correlates negatively with surgical outcome. *Oncotarget* 8, 7710 (2017).

SI-1. A. A. Green, P. A. Silver, J. J. Collins, P. Yin, Toehold switches: de-novo-designed regulators of gene expression. *Cell* 159, 925-939 (2014).

SI-2. K. Pardee et al., Rapid, low-cost detection of Zika virus using programmable biomolecular components. *Cell* 165, 1255-1266 (2016).

SI-3. K. Pardee et al., Paper-based synthetic gene networks. *Cell* 159, 940-954 (2014).

SI-4. S. E. Hunt et al., Ensembl variation resources. *Database* 2018, (2018).

SI-5. P. Oberacker et al., Bio-On-Magnetic-Beads (BOMB): Open platform for high-throughput nucleic acid extraction and manipulation. *PLoS biology* 17, e3000107 (2019).

SI-6. A. Espah Borujeni, H. M. Salis, Translation initiation is controlled by RNA folding kinetics via a ribosome drafting mechanism. *Journal of the American Chemical Society* 138, 7016-7023 (2016).

SI-7. T. L. Bailey, DREME: motif discovery in transcription factor ChIP-seq data. *Bioinformatics* 27, 1653-1659 (2011).

ASPECTS AND EMBODIMENTS OF THIS DISCLOSURE

Clause 1. A toehold riboregulator having (a) a nucleic acid sequence comprising any one of SEQ ID NOs: 1-244,000, or (b) nucleotides 21-103 of any one of SEQ ID NOs: 1-244,000, or (c) nucleotides 21-100 of any one of SEQ ID NOs: 1-244,000, or (d) RNA versions of (a), (b) or (c).

Clause 2. The toehold riboregulator of clause 1 covalently attached, at its 3' end, to a nucleic acid encoding a reporter protein or reporter RNA.

Clause 3. The toehold riboregulator of clause 1 or 2, wherein the riboregulator is specific for astrovirus, cardiovirus, chikungunya virus, cosavirus, coxsackie virus, dengue virus, ebola virus, hantavirus, human immunodeficiency virus, human parvo virus, human rhino virus, influenza virus: h1n1, influenza virus: h3n2, lassa virus, leishmanial virus, Marburg virus, papilloma virus, poliovirus, rabies virus, smallpox virus, west nile virus, yellow fever virus, or zika virus.

Clause 4. The toehold riboregulator of clause 1 or 2, wherein the riboregulator is specific for a human mRNA selected from AC097634.4, ACTB, ACTL6A, ACTN4, AEBP1, AEBP2, AGO1, AGO2, AHR, AIRE, AKNA, AL121581.1, ALX1, ALX4, ANHX, AR, ARHGAP35, ARID3A, ARID3B, ARID3C, ARID4A, ARID4B, ARID5A, ARID5B, ARNT, ARNT2, ARNTL, ARNTL2, ARRB1, ARX, ASCL1, ASCL2, ASCL3, ASCL4, ASCL5, ASH2L, ATF1, ATF2, ATF3, ATF4, ATF5, ATF6, ATF6B, ATMIN, ATOH1, ATOH8, ATXN3, BACH1, BACH2, BARHL1, BARHL2, BARX1, BARX2, BASP1, BATF, BATF2, BATF3, BAZ2A, BCL11A, BCL11B, BCL6, BCL6B, BCOR, BHLHA15, BHLHE40, BHLHE41, BORCS8-MEF2B, BRCA1, BRD7, BRF2, CALCOCO1, CARF, CARM1, CBX4, CC2D1A, CC2D1B, CCAR1, CCNT1, CDC5L, CDK12, CDK13, CDK5RAP2, CDK9, CDX1, CDX2, CDX4, CEBPA, CEBPB, CEBPD, CEBPE, CEBPG, CEBPZ, CGGBP1, CHD2, CHD4, CHD7, CIART, CIITA, CITED1, CLOCK, CNBP, CREB1, CREB3, CREB3L1, CREB3L2, CREB3L3, CREB3L4, CREBBP, CREBRF, CREM, CRX, CRY1, CRY2, CT476828.9, CTCF, CTCFL, CUX1, CUX2, CXXC1, DACH1, DBP, DDIT3, DDN, DEAF1, DHX36, DHX9, DLX1, DLX2, DLX4, DLX5, DMBX1, DMRT1, DMRT2, DNMT3A, DPF2, DR1, DRAP1, DUX4, E2F1, E2F2, E2F3, E2F4, E2F6, E2F7, E2F8, E4F1, EAF2, EBF2, EBF3, EBF4, EED, EGR1, EGR2, EGR3, EGR4, EHF, EHMT2, ELF1, ELF3, ELF4, ELF5, ELK1, ELK3, ELK4, ELL3, ELMSAN1, EN1, ENO1, EOMES, EP300, ERBB4, ERG, ESR1, ESR2, ESRRA, ESRRB, ESRRG, ESX1, ETS1, ETS2, ETV1, ETV2, ETV3, ETV4, ETV5, ETV6, ETV7, EZH2, FERD3L, FEZF1, FEZF2, FIGLA, FLI1, FOS, FOSB, FOSL1, FOSL2, FOXA1, FOXA2, FOXA3, FOXC1, FOXC2, FOXD1, FOXD3, FOXF1, FOXF2, FOXH1, FOXI1, FOXJ1, FOXJ2, FOXK1, FOXK2, FOXL2, FOXM1, FOXN4, FOXO3, FOXP2, FOXP3, FOXQ1, FOXS1, FUBP3, GABPA, GABPB1, GABPB2, GADD45A, GATA1, GATA2, GATA3, GATA4, GATA5, GATA6, GATAD2B, GBX2, GCFC2, GCM1, GFI1, GLI1, GLI2, GLI3, GLIS1, GLIS2, GLMP, GMEB1, GMEB2, GRHL1, GRHL2, GSC, GSX1, GTF2B, GTF3C1, GZF1, H2AFY, H2AFY2, H2AFZ, H3F3A, H3F3B, HAND1, HAND2, HDAC1, HDAC2, HDAC4, HDAC5, HDAC6, HELT, HES1, HES2, HES3, HES4, HES5, HES6, HES7, HESX1, HEY1, HEY2, HEYL, HHEX, HIC2, HIF1A, HINFP, HIVEP1, HLF, HLTF, HMGA1, HMGA2, HMGB1, HMGB2, HMX1, HMX3, HNF1A, HNF1B, HNF4A, HNF4G, HNRNPC, HNRNPK, HNRNPL, HNRNPU, HOXA10, HOXA2, HOXA3, HOXA4, HOXA5, HOXA6, HOXA7, HOXA9, HOXB1, HOXB2, HOXB3, HOXB4, HOXB5, HOXB6, HOXB7, HOXB9, HOXC10, HOXC11, HOXC4, HOXC5, HOXC6, HOXD10, HOXD13, HOXD3, HOXD4, HOXD8, HOXD9, HR, HSF1, HSF2, HSF4, HSF5, HSFX1, HSFX2, HSFX3, HSFX4, HSFY1, HSFY2, IER2, IFI16, IKZF1, IKZF2, IKZF3, IKZF4, IKZF5, INSM1, IRF1, IRF2, IRF2BP1, IRF2BP2, IRF2BPL, IRF3, IRF4, IRF5, IRF6, IRF7, IRF8, IRF9, ISL1, JARID2, JDP2, JMJD1C, JUN, JUNB, JUND, KAT2B, KAT7, KCNIP3, KDM1A, KDM2B, KDM3A, KDM3B, KDM5A, KDM6A, KDM6B, KLF1, KLF10, KLF11, KLF12, KLF13, KLF15, KLF16, KLF17, KLF3, KLF4, KLF5, KLF6, KLF7, KLF8, KMT2A, KMT2D, LDB1, LEF1, LHX2, LHX3, LITAF, LMO2, LMO4, LMX1A, LMX1B, LONP1, LRRFIP1, LYL1, MACC1, MAF, MAF1, MAFA, MAFB, MAFF, MAFG, MAFK, MAX, MAZ, MBD2, MBD3, MED1, MED12, MED8, MEF2A, MEF2B, MEF2C, MEF2D, MEIS1, MEIS2, MEN1, MEOX1, MEOX2, MESP1, MESP2, MITF, MIXL1, MLX, MLXIP, MLXIPL, MMP12, MNT, MRTFA, MSC, MSGN1, MSX1, MSX2, MTA1, MTA2, MTERF3, MTF1, MTF2, MTOR, MUC1, MXD1, MXD3, MXI1, MYB, MYBBP1A, MYBL1, MYBL2, MYC, MYCN, MYEF2, MYF5, MYF6, MYOCD, MYOD1, MYOG, MYPOP, MYT1, MYT1L, MZF1, NACC2, NANOG, NCOA2, NCOR1, NCOR2, NDN, NEUROD1, NEUROD2, NEUROD6, NEUROG1, NEUROG2, NEUROG3, NFAT5, NFATC1, NFATC2, NFATC3, NFATC4, NFE2, NFE2L1, NFE2L2, NFE2L3, NFIA, NFIB, NFIC, NFIL3, NFKB1, NFKB2, NFX1, NFXL1, NFYA, NFYB, NFYC, NHLH1, NHLH2, NKRF, NKX2-1, NKX2-2, NKX2-5, NKX2-6, NKX2-8, NKX3-1, NKX3-2, NKX6-1, NKX6-2, NLRC5, NME1, NONO, NOTCH1, NPAS2, NPAS4, NPM1, NR1D1, NR1D2, NR1H2, NR1H3, NR1H4, NR1I2, NR1I3, NR2C1, NR2C2, NR2E3, NR2F1, NR2F6, NR3C1, NR4A1, NR4A2, NR4A3, NR5A1, NR5A2, NR6A1, NRF1, NRIP1, NRL, NSD1, ONECUT2, ONECUT3, OSR1, OSR2, OTX1, OTX2, OVOL1, PARP1, PATZ1, PAX1, PAX2, PAX4, PAX5, PAX6, PAX8, PAX9, PAXBP1, PBX1, PBX2, PBX3, PCGF3, PCGF5, PCGF6, PDX1, PER1, PER2, PER3, PGR, PHB, PHOX2A, PHOX2B, PIH1D1, PITX1, PITX2, PITX3, PKNOX2, PLAG1, PLAGL1, POLRMT, POU1F1, POU2AF1, POU2F1, POU2F2, POU2F3, POU3F2, POU3F4, POU4F1, POU4F2, POU4F3, POU5F1, POU6F1, PPARA, PPARD, PPARG, PRDM1, PRDM11, PRDM12, PRDM13, PRDM14, PRDM15, PRDM2, PRDM4, PRDM5, PRDM6, PRDM7, PRDM9, PRDX5, PRKN, PRMT5, PROP1, PROX1, PRRX1, PSPC1, PTF1A, PURA, PURB, PURG, RAI1, RARA, RARB, RARG, RAX, RAX2, RB1, RBBP4, RBBP5, RBL1, RBL2, RBMX, RBPJ, RBPJL, RCOR1, RCOR2, RCOR3, REL, RELA, RELB, REST, RFX1, RFX2, RFX3, RFX4, RFX5, RFX6, RFX7, RFX8, RNF10, RORA, RORB, RORC, RPS3, RPTOR, RREB1, RRN3, RUNX1, RUNX2, RUNX3, RUVBL2, RXRA, RXRB, SAFB, SALL1, SALL2, SARS, SATB1, SATB2, SCRT1, SCRT2, SCX, SETX, SFPQ, SIN3A, SIRT1, SIX1, SIX2, SIX3, SIX4, SIX5, SIX6, SKIL, SMAD1, SMAD2, SMAD3, SMAD4, SMAD5, SMAD6, SMAD7, SMARCA2, SMARCA4, SMARCB1, SMARCC1, SMARCC2, SMARCD2, SMARCE1, SMYD3, SNAI1, SNAI2, SNAI3, SNCA, SOX1, SOX10, SOX11, SOX12, SOX13, SOX17, SOX18, SOX2, SOX21, SOX3, SOX4, SOX6, SOX7, SOX8, SOX9, SP1, SP2, SP3, SP5, SP7, SPI1, SPIB, SPIC, SREBF1, SREBF2, SRF, SSBP2, SSBP3, SSBP4, ST18, STAT1, STAT3, STAT5B, STAT6, STOX1, SUV39H1, SUV39H2, SUZ12, TAF1, TAF1B, TAF1C, TAF2, TAF5, TAF7, TAF7L, TAF9, TAF9B, TAL1, TAL2, TBL1X, TBL1XR1, TBP, TBPL1, TBPL2, TBR1, TBX15, TBX18, TBX19, TBX2, TBX20, TBX21, TBX22, TBX3, TBX5, TBX6, TBXT, TCF12, TCF15, TCF20, TCF21, TCF3, TCF4, TCF7, TCF7L1, TCF7L2, TCFL5, TEAD1, TEAD2, TEAD3, TEAD4, TEF, TFAM, TFAP2A, TFAP2B, TFAP2C, TFAP2D, TFAP2E, TFAP4, TFCP2, TFCP2L1, TFDP1, TFDP2, TFE3, TFEB, TFEC, TGIF1, THAP1, THAP11, THRA, THRAP3, THRB, TIPARP, TLX1, TNF, TOP1, TOX2, TOX3, TP53, TP63, TP73, TRERF1, TRIM24, TRPS1, TWIST1, TXK, UBTF, UHRF1, USP3, UTY, VAX1, VAX2, VDR, VEZF1, WBP2, WNT1, WNT11, WNT5A, WT1, XBP1, XRCC5, XRCC6, XRN2, YAP1, YBX1, YBX3, YY1, YY2, ZBED1, ZBTB14, ZBTB16, ZBTB17, ZBTB2, ZBTB20, ZBTB24, ZBTB4, ZBTB48, ZBTB5, ZBTB7A, ZBTB7B, ZC3H4, ZC3H6, ZC3H8, ZEB1, ZFHX2, ZFHX3, ZFHX4, ZFP42, ZFPM1, ZGPAT, ZHX3, ZIC1, ZIC2, ZIC3, ZIC4, ZIC5, ZKSCAN3, ZNF131, ZNF143, ZNF148, ZNF174, ZNF175, ZNF202, ZNF205, ZNF217, ZNF219, ZNF239, ZNF277, ZNF281, ZNF322, ZNF335, ZNF350, ZNF395, ZNF431, ZNF497, ZNF501, ZNF513, ZNF516, ZNF536, ZNF541, ZNF564, ZNF568, ZNF589, ZNF605, ZNF613, ZNF639, ZNF649, ZNF658, ZNF668, ZNF691, ZNF692, ZNF704, ZNF709, ZNF711, ZNF740, ZNF746, ZNF750, ZNF821, ZNF835, ZNF93, and ZSCAN21.

Clause 5. The toehold riboregulator of clause 1 or 2, wherein the riboregulator is specific for a human mRNA encoding STAT3.

Clause 6. A method comprising
contacting a sample with a toehold riboregulator of any one of clauses 2-5 under conditions sufficient to allow the toehold riboregulator to hybridize to its respective trigger nucleic acid, and detecting and optionally measuring expression of the reporter protein or reporter RNA.

Clause 7. The method of clause 6, wherein the sample is obtained from a human subject.

Clause 8. The method of clause 7, wherein the subject is suspected of having cancer.

Clause 9. The method of clause 7, wherein the subject is suspected of having an infection of a virus of clause 3.

Clause 10. A method of treating a subject, comprising administering an effective amount of an anti-viral agent to a subject having a viral infection, wherein the subject is identified as having a viral infection by detecting viral mRNA in a sample from the subject using a toehold riboregulator of clause 3.

Clause 11. A method of treating a subject, comprising administering an effective amount of an anti-cancer agent to a subject having a cancer, wherein the subject is identified as having a cancer by detecting increased mRNA expression of a human transcription factor in a sample from the subject using a toehold riboregulator of clause 4 or 5.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCE LISTING

The patent contains a lengthy sequence listing. A copy of the sequence listing is available in electronic form from the USPTO web site (https://seqdata.uspto.gov/docdetail?docId=US12624385B2). An electronic copy of the sequence listing will also be available from the USPTO upon request and payment of the fee set forth in 37 CFR 1.19(b)(3).

What is claimed is:

1. A toehold riboregulator having:
 (a) a nucleic acid sequence comprising any one of SEQ ID NOs: 43841, 9602, 62866, 19367, 164989, 111698, and 236638, or
 (b) nucleotides 21-103 of any one of SEQ ID NOs: 43841, 9602, 62866, 19367, 164989, 111698, and 236638, or
 (c) nucleotides 21-100 of any one of SEQ ID NOs: 43841, 9602, 62866, 19367, 164989, 111698, and 236638, or
 (d) RNA versions of (a), (b) or (c).

2. The toehold riboregulator of claim 1, comprising any one of SEQ ID NOs: 43841, 9602, 62866, and 19367, or RNA versions thereof.

3. The toehold riboregulator of claim 1, having;
 (a) a nucleic acid sequence comprising SEQ ID NO: 9602, or
 (b) nucleotides 21-103 of SEQ ID NO: 9602, or
 (c) nucleotides 21-100 of SEQ ID NO: 9602, or
 (d) RNA versions of (a), (b) or (c).

4. The toehold riboregulator of claim 1, having:
 (a) a nucleic acid sequence comprising SEQ ID NO: 19367, or
 (b) nucleotides 21-103 of SEQ ID NO: 19367, or
 (c) nucleotides 21-100 of SEQ ID NO: 19367, or
 (d) RNA versions of (a), (b) or (c).

5. The toehold riboregulator of claim 1, having:
 (a) a nucleic acid sequence comprising SEQ ID NO: 164989, or
 (b) nucleotides 21-103 of SEQ ID NO: 164989, or
 (c) nucleotides 21-100 of SEQ ID NO: 164989, or
 (d) RNA versions of (a), (b) or (c).

6. The toehold riboregulator of claim 1, having:
 (a) a nucleic acid sequence comprising SEQ ID NO: 111698, or
 (b) nucleotides 21-103 of SEQ ID NO: 111698, or
 (c) nucleotides 21-100 of SEQ ID NO: 111698, or
 (d) RNA versions of (a), (b) or (c).

7. The toehold riboregulator of claim 1, having:
 (a) a nucleic acid sequence comprising SEQ ID NO: 236638, or
 (b) nucleotides 21-103 of SEQ ID NO: 236638, or
 (c) nucleotides 21-100 of SEQ ID NO: 236638, or
 (d) RNA versions of (a), (b) or (c).

8. The toehold riboregulator of claim 1 covalently attached, at its 3' end, to a nucleic acid encoding a reporter protein or reporter RNA.

9. The toehold riboregulator of claim 1, wherein the toehold riboregulator is specific for dengue virus, human rhino virus, or smallpox virus.

10. The toehold riboregulator of claim 1, wherein the toehold riboregulator is specific for a human mRNA encoding a transcription factor selected from E2F3, NCOR1, or ZNF175.

11. A method comprising:
 contacting a sample with a toehold riboregulator of claim 1, covalently attached, at its 3' end, to a nucleic acid encoding a reporter protein or reporter RNA, under conditions sufficient to allow the toehold riboregulator to hybridize to its respective trigger nucleic acid, and detecting and optionally measuring expression of the reporter protein or reporter RNA,
 wherein the toehold riboregulator is an RNA.

12. The method of claim 11, wherein the sample is obtained from a human subject.

13. The method of claim 12, wherein the subject is suspected of having cancer.

14. The method of claim 12, wherein the subject is suspected of having a viral infection.

15. The method of claim 11, wherein the toehold riboregulator comprises an RNA version of any one of SEQ ID NOs: 43841, 9602, 62866, and 19367.

16. The method of claim 11, wherein the toehold riboregulator is a plurality of toehold riboregulators comprising RNA versions of SEQ ID NO: 43841 and SEQ ID NO: 62866.

17. The method of claim 11, wherein the subject is suspected of having a smallpox virus infection or having been exposed to smallpox virus.

18. The method of claim 11, wherein the subject is suspected of having dengue virus infection or having been exposed to dengue virus.

19. The method of claim 11, wherein the subject is suspected of having human rhino virus infection or having been exposed to human rhino virus.

20. The method of claim 11, wherein the sample has been treated to amplify RNA prior to contact with the toehold riboregulator.

21. The method of claim 20, wherein the sample has been treated to amplify RNA isothermally prior to contact with the toehold riboregulator.

22. A plurality of toehold riboregulators comprising a toehold riboregulator comprising SEQ ID NO: 43841 and a toehold riboregulator comprising SEQ ID NO: 62866, or RNA versions thereof.

23. A plurality of toehold riboregulators, each comprising:
   (a) a nucleic acid sequence comprising SEQ ID NO: 43841 or SEQ ID NO: 62866, or
   (b) nucleotides 21-103 of SEQ ID NO: 43841 or SEQ ID NO: 62866, or
   (c) nucleotides 21-100 of SEQ ID NO: 43841 or SEQ ID NO: 62866, or
   (d) RNA versions of (a), (b) or (c).

* * * * *